US012135326B2

(12) United States Patent
Huang et al.

(10) Patent No.: US 12,135,326 B2
(45) Date of Patent: Nov. 5, 2024

(54) DETECTION OF ANALYTES BY NANOPORE WITHOUT USING ELECTRODES

(71) Applicant: NANJING UNIVERSITY, Jiangsu (CN)

(72) Inventors: Shuo Huang, Nanjing (CN); Yuqin Wang, Nanjing (CN)

(73) Assignee: NANJING UNIVERSITY (CN)

( * ) Notice: Subject to any disclaimer, the term of this patent is extended or adjusted under 35 U.S.C. 154(b) by 633 days.

(21) Appl. No.: 17/599,987

(22) PCT Filed: May 29, 2020

(86) PCT No.: PCT/CN2020/093215
§ 371 (c)(1),
(2) Date: Sep. 29, 2021

(87) PCT Pub. No.: WO2020/239066
PCT Pub. Date: Dec. 3, 2020

(65) Prior Publication Data
US 2022/0146521 A1    May 12, 2022

(30) Foreign Application Priority Data

May 29, 2019 (WO) ................ PCT/CN2019/089050

(51) Int. Cl.
*G01N 33/58* (2006.01)
*G01N 1/40* (2006.01)
*G01N 21/64* (2006.01)

(52) U.S. Cl.
CPC ......... *G01N 33/582* (2013.01); *G01N 1/4005* (2013.01); *G01N 21/6428* (2013.01);
(Continued)

(58) Field of Classification Search
CPC .......... C12Q 2565/631; G01N 1/4005; G01N 2001/4016; G01N 2021/6439; G01N 21/6428; G01N 21/6458; G01N 33/48721; G01N 33/58; G01N 33/582; G01N 33/6845; G01N 33/84
See application file for complete search history.

(56) References Cited

U.S. PATENT DOCUMENTS

2012/0176601 A1* 7/2012 Voeroes ............. G01N 33/5076 356/51
2017/0058336 A1  3/2017 Ivankin et al.
2018/0364169 A1* 12/2018 Anderson ............ G01N 33/542

FOREIGN PATENT DOCUMENTS

CN        102590525 A1    7/2012

OTHER PUBLICATIONS

International Search Report and Written Opinion mailed Aug. 27, 2020 in Int'l Application No. PCT/CN2020/093215.
(Continued)

*Primary Examiner* — Jennifer Wecker
(74) *Attorney, Agent, or Firm* — Duane Morris LLP; Thomas J. Kowalski

(57) ABSTRACT

A system without electrodes for identifying analytes based on optical measurement of ion flux through nanopores that is driven by a chemical gradient, and a method for identifying an analyte by using such system. A nanopore array without electrodes for identifying different analytes in parallel, a method for identifying different analytes by using such array, and a method of manufacturing such array.

20 Claims, 19 Drawing Sheets

Specification includes a Sequence Listing.

(52) U.S. Cl.
CPC ............... *G01N 2001/4016* (2013.01); *G01N 2021/6439* (2013.01)

(56) References Cited

OTHER PUBLICATIONS

Brett N. Anderson, et al., Probing Solid-State Nanopores with Light for the Detection of Unlabeled Analytes, ACSNANO (2014) vol. 8, No. 11, p. 11836-11845.
Audrey Ivankin, et al., Label-Free Optical Detection of Biomolecular Translocation through Nanopore Arrays, ACSNANO (2014) vol. 8, No. 10, p. 10774-10781.
Japanese Office Action issued Jun. 4, 2024 in co-pending Japanese Application No. 2021-560360.

\* cited by examiner

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: ssDNA in assay shown in Figure 17

<400> SEQUENCE: 1
gatagtgagc caaatttaaa                                              20

<210> SEQ ID NO 2
<211> LENGTH: 78
<212> TYPE: DNA
<213> ORGANISM: Artificial Sequence
<220> FEATURE:
<223> OTHER INFORMATION: 78 nt ssDNA-a
```

```
<400> SEQUENCE: 2
ttggcatgtc agaatgttag aatgttagaa tgttagaatg ttagaatgtt agaatgtttc    60
agatctcact atcaaaaa                                                  78

<210> SEQ ID NO 3
<211> LENGTH: 78
<212> TYPE: DNA
<213> ORGANISM: Artificial Sequence
<220> FEATURE:
<223> OTHER INFORMATION: 78 nt ssDNA-b

<400> SEQUENCE: 3
tttttgatag tgagatctga acattctaa cattctaaca ttctaacatt ctaacattct    60
aacattctga catgccaa                                                  78
```

DETECTION OF ANALYTES BY NANOPORE WITHOUT USING ELECTRODES

FIELD

This invention relates to a method for identify an analyte using protein nanopore.

BACKGROUND

Natural cross-membrane transport is assisted by different membrane transport proteins[1]. The transported solutes such as small ions[2], water[3], sugar[4] or even genetic materials[5] etc. are critical for regulating different cell activities. Though the detailed transport mechanism varies [6], the fact that single molecule identities could be reported during channel translocation forms the fundamental basis of nanopore sequencing as a biomimicry approach[7, 8]. As reported, nanopore sensing has been carried out from a planar lipid membrane[9], a droplet interface bilayer (DIB) [10], a hydrogel interface bilayer[11], synthetic solid state membranes[12], a glass nanopipette[13] or a cell membrane [14]. However, the core setup, which was adapted from electrophysiology, has remained unchanged since its first appearance in 1996[9].

During electrophysiology, the Ag/AgCl electrodes pair serves to apply a transmembrane electrical potential, which drives a sustained electro-migration of Cl⁻ and charged analytes. It also serves to record the ionic current fluctuations for single molecule identification (FIG. 1a). Without the electrodes, though vibrant thermal diffusion of ions across a nanopore exists in both directions, the net flow of ions and the electric field within the whole electrolyte-containing space is strictly zero due to the rule of electric neutrality (FIG. 1b)[15].

Electrophysiology measurements, which provide a decent temporal (~10 μs) and amplitude resolution (<0.1 pA)[16], satisfy the need from single channel recording based applications but are disadvantageous in the throughput[17]. Though urgently needed in nanopore sequencing and drug screening, simultaneous readout from 1 million channels hasn't be achieved without a sacrifice in the cost or the size of the device[17, 18]. Such urgent need thus stimulated us to re-think a simplified strategy for high-throughput channel recordings which may be further acquired from biomimicry.

Bacterial phage T4 injects its genomic DNA through channel proteins when intact with host cells[19]. *Staphylococcus Aureus* α-hemolysin (α-HL) leads to hemolysis of target cells due to passive leakage of nutrients through inserted channels[20]. These spontaneous molecular transport as acquired from natural evolution reminded us that external electronics is not indispensable for molecular transport. The remaining challenge is how nanopore sensing signals could be acquired without electrical connections.

Recent developments in optical single channel recording (oSCR)[21-25] has demonstrated an alternative strategy, which optically monitors $Ca^{2+}$ fluxes through individual nanopores embedded in a droplet interface bilayer (DIB) (FIG. 1c)[21, 23]. Though oSCR is advantageous in high-throughput measurements, a pair of electrodes were still utilized to electrophoretically drive a sustained flow of $Ca^{2+}$ through nanopores[23]. Manual insertion of electrodes into aqueous droplets, which requires delicate micromanipulation skills and may lead to a high risk of bilayer rupture[23], has hampered its wide use in academic studies and industrial applications.

SUMMARY

The invention provides systems for identifying analytes based on optical measurement of ion flux through nanopores which is driven by a chemical gradient. The invention also provides methods of using such systems for identifying the analytes, including methods of identifying a small molecule or a DNA such as dsDNA or ssDNA.

In one aspect of the present invention, a system without electrodes for identifying an analyte is provided, the system comprising:
  (a) a first compartment having a first aqueous solution in it, wherein the first aqueous solution comprises a fluorescent reporter molecule capable of emitting fluorescence when bound to an ionic species;
  (b) a second compartment having a second aqueous solution in it, wherein the second aqueous solution comprises the ionic species which specifically bound to said fluorescence reporter molecule; and
  (c) a membrane separating the first compartment and second compartment;
  wherein the membrane between the first compartment and the second compartment has at least one inserted nanopore such that the first compartment and the second compartment are connected by the nanopore;
  wherein there is a chemical gradient of the ionic species between the first compartment and the second compartment which can drive the ionic species to diffuse from the second compartment to the first compartment through the nanopores.

In some embodiments, the membrane is a solid membrane.

In some embodiments, the membrane is a semipermeable membrane.

In some embodiments, the osmolarity of the second aqueous solution is higher than the osmolarity of the first aqueous solution or the osmolality of the second aqueous solution is higher than the osmolality of the first aqueous solution; or the osmolarity of the second aqueous solution is equal to the osmolarity of the first aqueous solution or the osmolality of the second aqueous solution is equal to the osmolality of the first aqueous solution; or the osmolarity of the second aqueous solution is lower than the osmolarity of the first aqueous solution or the osmolality of the second aqueous solution is lower than the osmolality of the first aqueous solution.

In some embodiments, the semipermeable membrane consists of amphipathic molecules; preferably, the amphipathic molecule is a lipid or a triblock copolymer.

In some embodiments, the semipermeable membrane is a bilayer consisting of amphipathic molecules.

In some embodiments, the amphipathic molecule is lipid.

In some embodiments, the lipid is one or more selected from the group consisting of fatty acyls, glycerolipids, glycerophospholipids, sphingolipids, sterol lipids, prenollipids, saccharolipids, polyketides, phospholipids, glycolipids and cholesterol.

In some embodiments, the lipid is one or more selected from the group consisting of monoolein; 1,2-dioleoyl-sn glycero-S-phosphocholine (DOPC); 1,2-diphytanoyl-sn-glycero-3-phosphatidylcholine (DPhPC); palmitoyl oleoyl phosphatidylcholine (POPC); 1-palmitoyl-2-oleoyl phosphatidylethanolamine (POPE); 1-palmitoyl-2-oleoyl-phosphatidylethanolamine; 1-palmitoyl-2-oleoylphosphatidylglycerol (POPE/POPG) mixtures; and mixtures thereof.

In some embodiments, the first compartment is provided by an aqueous droplet.

In some embodiments, the second compartment is provided by a hydrogel layer; preferably, the hydrogel layer comprises 0.1-20% (w/v) agarose; more preferably, the hydrogel layer comprises 2-5% (w/v) agarose.

In some embodiments, the nanopore is selected from the group consisting of protein nanopore, DNA nanopore or solid nanopore.

In some embodiments, the protein nanopore is one or more selected from the group consisting of α-HL, ClyA, Phi29 connector protein, aerolysine, MspA, OmpF, OmpG, FraC, HlyA, SheA, sp1 and variants thereof; and ion channel.

In some embodiments, the protein nanopore is ClyA-RR or α-HL.

In some embodiments, the ionic species is one or more selected from the group consisting of $Ag^+$, $Ag^{2+}$, $Al^{3+}$, $As^{3+}$, $Au^+$, $Ba^{2+}$, $Bi^{3+}$, $Ca^{2+}$, $Cd^{2+}$, $Ce^{3+}$, $Ce^{4+}$, $Cl^-$, $Co^{2+}$, $Cr^{3+}$, $Cu^+$, $Cu^{2+}$, $Dy^{3+}$, $Eu^{3+}$, $Fe^{2+}$, $Fe^{3+}$, $Ga^{3+}$, $H^+$, $Hg^+$, $Hg^{2+}$, $In^{3+}$, $K^+$, $La^{3+}$, $Mg^{2+}$, $Mn^{2+}$, $Mo^{3+}$, $Na^+$, $Ni^{2+}$, $OH^-$, $Pb^{2+}$, $Pd^{2+}$, $Pt^{2+}$, $Pt^{4+}$, $Ru^{3+}$, $Sb^{3+}$, $Sc^{3+}$, $Sn^{2+}$, $Sr^{2+}$, $Tb^{3+}$, $Tl^+$, and $Zn^{2+}$.

In some embodiments, the fluorescent reporter molecule is one or more selected from the group consisting of Fura-2, Indo-1, Fluo-2, Fluo-3, Fluo-4, Fluo-8, Calcium Green-1, DCFH, DHR, SNARF, Cal-520, calcium-specific aminopolycarboxylic acid, BAPTA, SBFI, Asante NaTRIUM Green-1, Asante NaTRIUM Green-2, Thallos Potassium Ion Channel Reagent, Asante Potassium Green-1, Asante Potassium Green-2, Asante Potassium Green-3, PBFI, Fluo-2 Mg, Fura-2 Mg, Indo-1 Mg, Asante Magnesium Green, SPQ, MQAE, TSQ, TFL-Zn and ZINQUIN.

In some embodiments, the second aqueous solution comprises calcium chloride and optionally a buffering agent.

In some embodiments, the concentration of calcium chloride in the second aqueous solution is 0.01-6.76 M.

In some embodiments, the first aqueous solution comprises a chelating agent and optionally a buffering agent, wherein the chelating agent is able to bind to said ionic species; preferably, the chelating agent is EDTA, BAPTA, EGTA, CyDTA, DTPA, EDDP, HIDA, IDA, NTA, NTPO, TTHA, CA, TA, GA, HEDTA, or DEG.

In some embodiments, the system further comprises a light source for illuminating and a light sensor for detecting the fluorescence; preferably, the light source is laser, LED, halogen light, xenon light; preferably, the light sensor is CCD, sCMOS sensor or photodiode; more preferably, the light sensor is EMCCD or Avalanche Photodiode (APD).

In some embodiments, the system further comprises a device for Total Internal Reflection Fluorescence (TIRF), wide field fluorescence microscopy or confocal microscopy.

In some embodiments, the first aqueous solution or the second aqueous solution comprises the analyte.

In some embodiments, the analyte is selected from the group consisting of small molecule, macromolecule and bio-macromolecule.

In some embodiments, the analyte is selected from the group consisting of a compound, a drug, a sugar, an ion, a neurotransmitter, an amino acid, a nucleotide, a polymer, a polypeptide, a polysaccharide and a polynucleotide; preferably, the polynucleotide is a DNA or a RNA; more preferably, the DNA is a dsDNA or a ssDNA; more preferably, the RNA is miRNA, siRNA or tRNA.

In another aspect of the present invention, a method of identifying an analyte is provided, the method comprising the steps of:

(a) providing any one of above systems, wherein the analyte is provided in the first compartment or in the second compartment;
(b) applying a light capable of exciting the fluorescent reporter molecule to a region in the first compartment proximal to the nanopores;
(c) measuring the fluorescence signal from the fluorescent reporter molecule to identify the analyte.

In another aspect of the present invention, a method of manufacturing a system without electrodes is provided, comprising:

providing a first compartment having a first aqueous solution in it, wherein the first aqueous solution comprises a fluorescent reporter molecule capable of emitting fluorescence when bound to an ionic species;
providing a second compartment having a second aqueous solution in it, wherein the second aqueous solution comprises the ionic species which specifically bound to said fluorescence reporter molecule;
bringing the first compartment and the second compartment together in a hydrophobic medium containing amphipathic molecules such that a semipermeable membrane with an inserted nanopore is formed between the first compartment and the second compartment;
wherein a protein nanopore is provided in the first aqueous solution or the second aqueous solution.

In some embodiments, the osmolarity of the second aqueous solution is higher than the osmolarity of the first aqueous solution or the osmolality of the second aqueous solution is higher than the osmolality of the first aqueous solution; or the osmolarity of the second aqueous solution is equal to the osmolarity of the first aqueous solution or the osmolality of the second aqueous solution is equal to the osmolality of the first aqueous solution; or the osmolarity of the second aqueous solution is lower than the osmolarity of the first aqueous solution or the osmolality of the second aqueous solution is lower than the osmolality of the first aqueous solution.

In some embodiments, the semipermeable membrane consists of amphipathic molecules; preferably, the amphipathic molecule is a lipid or a triblock copolymer.

In some embodiments, the semipermeable membrane is a bilayer consisting of amphipathic molecules.

In some embodiments, the amphipathic molecule is lipid.

In some embodiments, the lipid is one or more selected from the group consisting of fatty acyls, glycerolipids, glycerophospholipids, sphingolipids, sterol lipids, prenollipids, saccharolipids, polyketides, phospholipids, glycolipids and cholesterol.

In some embodiments, the lipid is one or more selected from the group consisting of monoolein; 1,2-dioleoyl-sn glycero-S-phosphocholine (DOPC); 1,2-diphytanoyl-sn-glycero-3-phosphatidylcholine (DPhPC); palmitoyl oleoyl phosphatidylcholine (POPC); 1-palmitoyl-2-oleoyl phosphatidylethanolamine (POPE); 1-palmitoyl-2-oleoyl-phosphatidylethanolamine; 1-palmitoyl-2-oleoylphosphatidylglycerol (POPE/POPG) mixtures; and mixtures thereof.

In some embodiments, the first compartment is provided by an aqueous droplet.

In some embodiments, the second compartment is provided by a hydrogel layer; preferably, the hydrogel layer comprises 0.1-20% (w/v) agarose; more preferably, the hydrogel layer comprises 2-5% (w/v) agarose.

In some embodiments, the nanopore is selected from the group consisting of protein nanopore, DNA nanopore or solid nanopore.

In some embodiments, the protein nanopore is one or more selected from the group consisting of α-HL, ClyA, Phi29 connector protein, aerolysine, MspA, OmpF, OmpG, FraC, HlyA, SheA, sp1 and variants thereof; and ion channel.

In some embodiments, the protein nanopore is ClyA-RR or α-HL.

In some embodiments, the ionic species is one or more selected from the group consisting of $Ag^+$, $Ag^{2+}$, $Al^{3+}$, $As^{3+}$, $Au^+$, $Ba^{2+}$, $Bi^{3+}$, $Ca^{2+}$, $Cd^{2+}$, $Ce^{3+}$, $Ce^{4+}$, $Cl^-$, $Co^{2+}$, $Cr^{3+}$, $Cu^+$, $Cu^{2+}$, $Dy^{3+}$, $Eu^{3+}$, $Fe^{2+}$, $Fe^{3+}$, $Ga^{3+}$, $H^+$, $Hg^+$, $Hg^{2+}$, $In^{3+}$, $K^+$, $La^{3+}$, $Mg^{2+}$, $Mn^{2+}$, $Mo^{3+}$, $Na^+$, $Ni^{2+}$, $OH^-$, $Pb^{2+}$, $Pd^{2+}$, $Pt^{2+}$, $Pt^{4+}$, $Ru^{3+}$, $Sb^{3+}$, $Sc^{3+}$, $Sn^{2+}$, $Sr^{2+}$, $Tb^{3+}$, $Tl^+$, and $Zn^{2+}$.

In some embodiments, the fluorescent reporter molecule is one or more selected from the group consisting of Fura-2, Indo-1, Fluo-2, Fluo-3, Fluo-4, Fluo-8, Calcium Green-1, DCFH, DHR, SNARF, Cal-520, calcium-specific aminopolycarboxylic acid, BAPTA, SBFI, Asante NaTRIUM Green-1, Asante NaTRIUM Green-2, Thallos Potassium Ion Channel Reagent, Asante Potassium Green-1, Asante Potassium Green-2, Asante Potassium Green-3, PBFI, Fluo-2 Mg, Fura-2 Mg, Indo-1 Mg, Asante Magnesium Green, SPQ, MQAE, TSQ, TFL-Zn and ZINQUIN.

In some embodiments, the second aqueous solution comprises calcium chloride and optionally a buffering agent.

In some embodiments, the concentration of calcium chloride in the second aqueous solution is 0.01-6.76 M.

In some embodiments, the first aqueous solution comprises a chelating agent and optionally a buffering agent, wherein the chelating agent is able to bind to said ionic species; preferably, the chelating agent is EDTA, BAPTA, EGTA, CyDTA, DTPA, EDDP, HIDA, IDA, NTA, NTPO, TTHA, CA, TA, GA, HEDTA, or DEG.

In some embodiments, an analyte is provided in the first aqueous solution or the second aqueous solution.

In some embodiments, the analyte is selected from the group consisting of small molecule, macromolecule and bio-macromolecule.

In some embodiments, the analyte is selected from the group consisting of a compound, a drug, a sugar, an ion, a neurotransmitter, an amino acid, a nucleotide, a polymer, a polypeptide, a polysaccharide and a polynucleotide; preferably, the polynucleotide is a DNA or a RNA; more preferably, the DNA is a dsDNA or a ssDNA; more preferably, the RNA is miRNA, siRNA or tRNA.

In another aspect of the present invention, a nanopore array without electrodes for identifying multiple analytes is provided, the nanopore array comprising multiple systems in parallel and each system comprising:
(a) a first compartment having a first aqueous solution in it, wherein the first aqueous solution comprises a fluorescent reporter molecule capable of emitting fluorescence when bound to an ionic species;
(b) a second compartment having a second aqueous solution in it, wherein the second aqueous solution comprises the ionic species which specifically bound to said fluorescence reporter molecule; and
(c) a membrane separating the first compartment and second compartment;
wherein in each system, the membrane between the first compartment and the second compartment has at least one inserted nanopore such that the first compartment and the second compartment are connected by the nanopore in each system;
wherein in each system, there is a chemical gradient of the ionic species between the first compartment and the second compartment which can drive the ionic species to diffuse from the second compartment to the first compartment through the nanopores;
wherein the multiple systems are arranged such that the measured fluorescence can be distinguished for each system.

In some embodiments, in each system, the membrane between the first compartment and the second compartment system is a solid membrane.

In some embodiments, in each system, the membrane between the first compartment and the second compartment is a semipermeable membrane.

In some embodiments, in each system, the osmolarity of the second aqueous solution is higher than the osmolarity of the first aqueous solution or the osmolality of the second aqueous solution is higher than the osmolality of the first aqueous solution; or the osmolarity of the second aqueous solution is equal to the osmolarity of the first aqueous solution or the osmolality of the second aqueous solution is equal to the osmolality of the first aqueous solution; or the osmolarity of the second aqueous solution is lower than the osmolarity of the first aqueous solution or the osmolality of the second aqueous solution is lower than the osmolality of the first aqueous solution.

In some embodiments, the semipermeable membrane consists of amphipathic molecules; preferably, the amphipathic molecule is a lipid or a triblock copolymer.

In some embodiments, the semipermeable membrane is a bilayer consisting of amphipathic molecules.

In some embodiments, the amphipathic molecule is lipid.

In some embodiments, the lipid is one or more selected from the group consisting of fatty acyls, glycerolipids, glycerophospholipids, sphingolipids, sterol lipids, prenollipids, saccharolipids, polyketides, phospholipids, glycolipids and cholesterol.

In some embodiments, the lipid is one or more selected from the group consisting of monoolein; 1,2-dioleoyl-sn glycero-S-phosphocholine (DOPC); 1,2-diphytanoyl-sn-glycero-3-phosphatidylcholine (DPhPC); palmitoyl oleoyl phosphatidylcholine (POPC); 1-palmitoyl-2-oleoyl phosphatidylethanolamine (POPE); 1-palmitoyl-2-oleoyl-phosphatidylethanolamine; 1-palmitoyl-2-oleoylphosphatidylglycerol (POPE/POPG) mixtures; and mixtures thereof.

In some embodiments, the first compartments of the multiple systems are separated from each other.

In some embodiments, the first compartment of each system is provided by an aqueous droplet.

In some embodiments, the second compartment of the multiple system is a single compartment.

In some embodiments, the second compartment of each system is provided by a hydrogel layer; preferably, the hydrogel layer comprises 0.1-20% (w/v) agarose; more preferably, a hydrogel layer comprises 2-5% (w/v) agarose.

In some embodiments, the second compartments of the multiple systems are provided by a single hydrogel layer.

In some embodiments, in each system, the nanopore is selected from the group consisting of protein nanopore, DNA nanopore or solid nanopore.

In some embodiments, the protein nanopore is one or more selected from the group consisting of α-HL, ClyA, Phi29 connector protein, aerolysine, MspA, OmpF, OmpG, FraC, HlyA, SheA, sp1 and variants thereof; and ion channel.

In some embodiments, in each system, the protein nanopore is ClyA-RR or α-HL.

In some embodiments, in each system, the ionic species is one or more selected from the group consisting of $Ag^+$, $Ag^{2+}$, $Al^{3+}$, $As^{3+}$, $Au^+$, $Ba^{2+}$, $Bi^{3+}$, $Ca^{2+}$, $Cd^{2+}$, $Ce^{3+}$, $Ce^{4+}$, $Cl^-$, $Co^{2+}$, $cr^{3+}$, $Cu^+$, $Cu^{2+}$, $Dy^{3+}$, $Eu^{3+}$, $Fe^{2+}$, $Fe^{3+}$, $Ga^{3+}$, $H^+$, $Hg^+$, $Hg^{2+}$, $In^{3+}$, $K^+$, $La^{3+}$, $Mg^{2+}$, $Mn^{2+}$, $Mo^{3+}$, $Na^+$, $Ni^{2+}$, $OH^-$, $Pb^{2+}$, $Pd^{2+}$, $Pt^{2+}$, $Pt^{4+}$, $Ru^{3+}$, $Sb^{3+}$, $Sc^{3+}$, $Sn^{2+}$, $Sr^{2+}$, $Tb^{3+}$, $Tl^+$, and $Zn^{2+}$.

In some embodiments, in each system, the fluorescent reporter molecule is one or more selected from the group consisting of Fura-2, Indo-1, Fluo-2, Fluo-3, Fluo-4, Fluo-8, Calcium Green-1, DCFH, DHR, SNARF, Cal-520, calcium-specific aminopolycarboxylic acid, BAPTA, SBFI, Asante NaTRIUM Green-1, Asante NaTRIUM Green-2, Thallos Potassium Ion Channel Reagent, Asante Potassium Green-1, Asante Potassium Green-2, Asante Potassium Green-3, PBFI, Fluo-2 Mg, Fura-2 Mg, Indo-1 Mg, Asante Magnesium Green, SPQ, MQAE, TSQ, TFL-Zn and ZINQUIN.

In some embodiments, in each system, the second aqueous solution comprises calcium chloride and optionally a buffering agent.

In some embodiments, in each system, the concentration of calcium chloride in the second aqueous solution is 0.01-6.76 M.

In some embodiments, in each system, the first aqueous solution comprises a chelating agent and optionally a buffering agent, wherein the chelating agent is able to bind to said ionic species; preferably, the chelating agent is EDTA, BAPTA, EGTA, CyDTA, DTPA, EDDP, HIDA, IDA, NTA, NTPO, TTHA, CA, TA, GA, HEDTA or DEG.

In some embodiments, the array further comprises a light source for illuminating and a light sensor for detecting the fluorescence; preferably, the light source is laser, LED, halogen light, xenon light; preferably, the light sensor is CCD, sCMOS sensor, or photodiode; more preferably, the light sensor is EMCCD or Avalanche Photodiode (APD).

In some embodiments, the array further comprises a device for Total Internal Reflection Fluorescence (TIRF), wide field fluorescence microscopy or confocal microscopy.

In some embodiments, in each system, the first aqueous solution or the second aqueous solution comprises the analyte.

In some embodiments, in each system, the analyte is selected from the group consisting of small molecule, macromolecule and bio-macromolecule.

In some embodiments, in each system, the analyte is selected from the group consisting of a compound, a drug, a sugar, an ion, a neurotransmitter, an amino acid, a nucleotide, a polymer, a polypeptide, a polysaccharide and a polynucleotide; preferably, the polynucleotide is a DNA or a RNA; more preferably, the DNA is a dsDNA or a ssDNA; more preferably, the RNAis miRNA, siRNA or tRNA.

In some embodiments, different analytes is physically separated into various systems.

In some embodiments, the density of the systems in the nanopore array is 10-1000 per $mm^2$.

In some embodiments, the total area provided by the multiple systems is 1-100 $mm^2$.

In some embodiments, the number of the multiple systems is 4-1,000,000; preferably, the number of the multiple systems is 10-1000.

In another aspect of the present invention, a multiplex method for identifying multiple analytes is provided, the method comprising:
(a) providing any one of above nanopore arrays, wherein two or more analytes are provided in various systems of the nanopore array;
(b) applying a light signal capable of exciting the fluorescent reporter molecules contained in each of the first compartments to a region in the multiple first compartment proximal to the nanopores;
(c) measuring multiple fluorescence signals from the fluorescent reporter molecules contained in each system to identify the multiple analytes.

In another aspect of the present invention, a method of manufacturing a nanopore array without electrodes is provided, the method comprising:
providing multiple aqueous droplets, wherein each of the aqueous droplets comprises a first aqueous solution which comprises a protein nanopore, an analyte and a fluorescent reporter molecule capable of emitting fluorescence when bound to an ionic species;
providing a hydrogel layer, wherein the hydrogel layer comprises the ionic species;
bringing the multiple aqueous droplets and the hydrogel layer together in a hydrophobic medium comprising amphipathic molecules such that a semipermeable membrane is formed between each of the aqueous droplets and the hydrogel layer.

In some embodiments, the osmolarity of the hydrogel is higher than the osmolarity of each aqueous dropletd or the osmolality of the hydrogel is higher than the osmolality of each aqueous droplet; or the osmolality of the hydrogel is equal to the osmolarity of each aqueous droplet or the osmolality of the hydrogel is equal to the osmolality of the each aqueous droplets; or the osmolality of the hydrogel is lower than the osmolarity of each aqueous droplet or the osmolality of the hydrogel is lower than the osmolality of each aqueous droplet.

In some embodiments, the semipermeable membrane consists of amphipathic molecules; preferably, the amphipathic molecule is a lipid or a triblock copolymer.

In some embodiments, the semipermeable membrane is a bilayer consisting of amphipathic molecules.

In some embodiments, the amphipathic molecule is lipid.

In some embodiments, the lipid is one or more selected from the group consisting of fatty acyls, glycerolipids, glycerophospholipids, sphingolipids, sterol lipids, prenollipids, saccharolipids, polyketides, phospholipids, glycolipids and cholesterol.

In some embodiments, the lipid is one or more selected from the group consisting of monoolein; 1,2-dioleoyl-sn glycero-S-phosphocholine (DOPC); 1,2-diphytanoyl-sn-glycero-3-phosphatidylcholine (DPhPC); palmitoyl oleoyl phosphatidylcholine (POPC); l-palmitoyl-2-oleoyl phosphatidylethanolamine (POPE); 1-palmitoyl-2-oleoyl-phosphatidylethanolamine; 1-palmitoyl-2-oleoylphosphatidylglycerol (POPE/POPG) mixtures; and mixtures thereof.

In some embodiments, the hydrogel layer comprises 0.1-20% (w/v) agarose; preferably, the hydrogel layer comprises 2-5% (w/v) agarose.

In some embodiments, in each system, the nanopore is selected from the group consisting of protein nanopore, DNA nanopore or solid nanopore.

In some embodiments, the protein nanopore in each aqueous droplet is one or more selected from the group consisting of α-HL, ClyA, Phi29 connector protein, aerolysine, MspA, OmpF, OmpG, FraC, HlyA, SheA, sp1 and variants thereof; and ion channel.

In some embodiments, the protein nanopore in each aqueous droplet is ClyA-RR or α-HL.

In some embodiments, the ionic species in the hydrogel layer is one or more selected from the group consisting of $Ag^+$, $Ag^{2+}$, $Al^{3+}$, $As^{3+}$, $Au^+$, $Ba^{2+}$, $Bi^{3+}$, $Ca^{2+}$, $Cd^{2+}$, $Ce^{3+}$, $Ce^{4+}$, $Cl^-$, $Co^{2+}$, $Cr^{3+}$, $Cu^+$, $Cu^{2+}$, $Dy^{3+}$, $Eu^{3+}$, $Fe^{2+}$, $Fe^{3+}$, $Ga^{3+}$, $H^+$, $Hg^+$, $Hg^{2+}$, $In^{3+}$, $K^+$, $La^{3+}$, $Mg^{2+}$, $Mn^{2+}$, $Mo^{3+}$, Na$^+$, Ni$^{2+}$, OH$^-$, Pb$^{2+}$, Pd$^{2+}$, Pt$^{2+}$, Pt$^{4+}$, Ru$^{3+}$, Sb$^{3+}$, Sc$^{3+}$, Sn$^{2+}$, Sr$^{2+}$, Tb$^{3+}$, Tl$^+$, and Zn$^{2+}$.

In some embodiments, the fluorescent reporter molecule in each aqueous droplet is one or more selected from the group consisting of Fura-2, Indo-1, Fluo-2, Fluo-3, Fluo-4, Fluo-8, Calcium Green-1, DCFH, DHR, SNARF, Cal-520, calcium-specific aminopolycarboxylic acid, BAPTA, SBFI, Asante NaTRIUM Green-1, Asante NaTRIUM Green-2, Thallos Potassium Ion Channel Reagent, Asante Potassium Green-1, Asante Potassium Green-2, Asante Potassium Green-3, PBFI, Fluo-2 Mg, Fura-2 Mg, Indo-1 Mg, Asante Magnesium Green, SPQ, MQAE, TSQ, TFL-Zn and ZINQUIN.

In some embodiments, the hydrogel layer comprises calcium chloride and optionally a buffering agent.

In some embodiments, the concentration of calcium chloride in the hydrogel layer is 0.01-6.76 M.

In some embodiments, each aqueous droplet comprises a chelating agent and optionally a buffering agent, wherein the chelating agent is able to bind to said ionic species; preferably, the chelating agent is EDTA, BAPTA, EGTA, CyDTA, DTPA, EDDP, HIDA, IDA, NTA, NTPO, TTHA, CA, TA, GA, HEDTA or DEG.

In some embodiments, the analyte in each aqueous droplet is selected from the group consisting of small molecule, macromolecule and bio-macromolecule.

In some embodiments, the analyte in each aqueous droplet is selected from the group consisting of a compound, a drug, a sugar, an ion, a neurotransmitter, an amino acid, a nucleotide, a polymer, a polypeptide, a polysaccharide and a polynucleotide; preferably, the polynucleotide is a DNA or a RNA; more preferably, the DNA is a dsDNA or a ssDNA; more preferably, the RNA is miRNA, siRNA or tRNA.

In some embodiments, different analytes is provided in various systems.

In some embodiments, the number of the aqueous droplets is 4-1,000,000; preferably, the number of the aqueous droplets is 10-1000.

In another aspect, the present invention provides use of above system for optical analyte analysis.

In another aspect, the present invention provides use of above nanopore array for optical analyte analysis.

In another aspect, the present invention provides a kit for forming a nanopore array is provided, the kit containing:
  filling hydrogel comprising agarose, a buffering agent and an ionic species which is able to specifically bind to a fluorescence reporter molecule to cause it emit fluorescence;
  aqueous solution comprising a chelating agent, said fluorescent reporter molecule capable of emitting fluorescence when bound to the ionic species, and a buffering agent; wherein the chelating agent is able to bind to said ionic species;
  hydrophobic medium containing amphipathic molecules;
  a solid support.

In some embodiments, the osmolarity of the filling hydrogel is higher than the osmolarity of the aqueous solution or the osmolality of the filling hydrogel is higher than the osmolality of the aqueous solution; or the osmolarity of the filling hydrogel is equal to the osmolarity of the aqueous solution or the osmolality of the filling hydrogel is equal to the osmolality of the aqueous solution; or the osmolarity of the filling hydrogel is lower than the osmolarity of the aqueous solution or the osmolality of the filling hydrogel is lower than the osmolality of the aqueous solution.

In some embodiments, the amphipathic molecule is lipid.

In some embodiments, the lipid is one or more selected from the group consisting of fatty acyls, glycerolipids, glycerophospholipids, sphingolipids, sterol lipids, prenollipids, saccharolipids, polyketides, phospholipids, glycolipids and cholesterol.

In some embodiments, the lipid is one or more selected from the group consisting of monoolein; 1,2-dioleoyl-sn glycero-S-phosphocholine (DOPC); 1,2-diphytanoyl-sn-glycero-3-phosphatidylcholine (DPhPC); palmitoyl oleoyl phosphatidylcholine (POPC); 1-palmitoyl-2-oleoyl phosphatidylethanolamine (POPE); 1-palmitoyl-2-oleoyl-phosphatidylethanolamine; 1-palmitoyl-2-oleoylphosphatidylglycerol (POPE/POPG) mixtures; and mixtures thereof.

In some embodiments, the aqueous solution also comprises a protein nanopore.

In some embodiments, the nanopore is selected from the group consisting of protein nanopore, DNA nanopore or solid nanopore.

In some embodiments, the protein nanopore is one or more selected from the group consisting of α-HL, ClyA, Phi29 connector protein, aerolysine, MspA, OmpF, OmpG, FraC, HlyA, SheA, sp1 and variants thereof; and ion channel.

In some embodiments, the protein nanopore is ClyA-RR or α-HL.

In some embodiments, the ionic species in the hydrogel layer is one or more selected from the group consisting of Ag$^+$, Ag$^{2+}$, Al$^{3+}$, As$^{3+}$, Au$^+$, Ba$^{2+}$, Bi$^{3+}$, Ca$^{2+}$, Cd$^{2+}$, Ce$^{3+}$, Ce$^{4+}$, Cl$^-$, Co$^{2+}$, Cr$^{3+}$, Cu$^+$, Cu$^{2+}$, Dy$^{3+}$, Eu$^{3+}$, Fe$^{2+}$, Fe$^{3+}$, Ga$^{3+}$, H$^+$, Hg$^+$, Hg$^{2+}$, In$^{3+}$, K$^+$, La$^{3+}$, Mg$^{2+}$, Mn$^{2+}$, Mo$^{3+}$, Na$^+$, Ni$^{2+}$, OH$^-$, Pb$^{2+}$, Pd$^{2+}$, Pt$^{2+}$, Pt$^{4+}$, Ru$^{3+}$, Sb$^{3+}$, Sc$^{3+}$, Sn$^{2+}$, Sr$^{2+}$, Tb$^{3+}$, Tl$^+$, and Zn$^{2+}$.

In some embodiments, the fluorescent reporter molecule in each aqueous droplet is one or more selected from the group consisting of Fura-2, Indo-1, Fluo-2, Fluo-3, Fluo-4, Fluo-8, Calcium Green-1, DCFH, DHR, SNARF, Cal-520, calcium-specific aminopolycarboxylic acid, BAPTA, SBFI, Asante NaTRIUM Green-1, Asante NaTRIUM Green-2, Thallos Potassium Ion Channel Reagent, Asante Potassium Green-1, Asante Potassium Green-2, Asante Potassium Green-3, PBFI, Fluo-2 Mg, Fura-2 Mg, Indo-1 Mg, Asante Magnesium Green, SPQ, MQAE, TSQ, TFL-Zn and ZINQUIN.

In some embodiments, the filling hydrogel comprises calcium chloride to provide Ca$^{2+}$ as the ionic species.

In some embodiments, the concentration of calcium chloride in the hydrogel layer is 0.01-6.76 M; preferably, the concentration of calcium chloride in the second aqueous solution is 0.15 M-6 M.

In some embodiments, the filling hydrogel comprises 2.5% agarose, 1.5 M CaCl$_2$, and 10 mM HEPES, pH 7.0.

In some embodiments, the aqueous solution also comprises KCl.

In some embodiments, the aqueous solution may comprise 1.5 M KCl, 400 μM EDTA, 40 μM Fluo-8, 10 mM HEPES, pH 7.0.

In some embodiments, the hydrophobic medium containing amphipathic molecules may be a lipid oil which comprises 5 mg dried film of DPHPC lipids dissolved in a 2 mL mixture of hexadecane and silicone oil with a 1:1 volume ratio.

In some embodiments, the kit also comprises a coating hydrogel. Preferably, the coating hydrogel may comprise 0.75% (w/v) agarose in water.

result of a. Parameters such as the center of the peak ($x_c$, $y_c$), the peak amplitude (A+$z_0$) and the full width of half maximum (FWHM) can be extracted from the fitting results (see Methods). c, The definition of signal and background according to FWHM. In brief, the total pixel values within the circle with a diameter of 2 FWHM are defined as the signal. The total pixel values within the outer ring, which is between the diameter of 3 FWHM and 4 FWHM, are defined as the background. The demonstrated image processing is automated using MATLAB.

Figure 1:
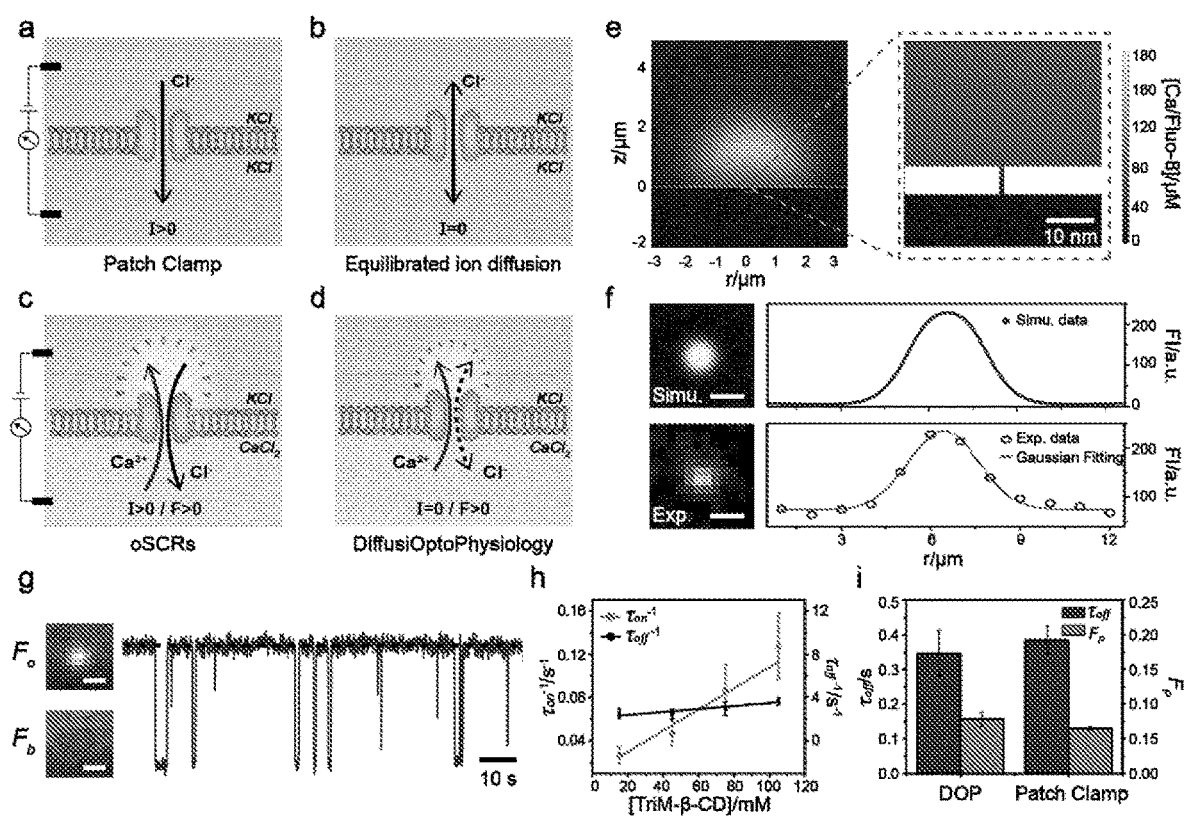
FIG. 1 shows DiffusiOptoPhysiology and its application in TriM-β-CD sensing. a-d, Schematics of ion transport through a nanopore in different measurement platforms. a, During electrophysiology recording, electrophoretic motion of Cl⁻ through a nanopore is observed when a transmembrane potential is applied via a pair of Ag/AgCl electrodes. b, Without electrodes, although thermal motion of ions across the nanopore exists in both directions, no net flow of ion transport should happen according to the rule of electroneutrality. c, During oSCRs, directional motion of $Ca^{2+}$, which is electrophoretically driven through a nanopore, establishes a steep $Ca^{2+}$ concentration gradient. Upon binding with Fluo-8 in cis, the Fluo-8/$Ca^{2+}$ complex around the pore vicinity emits strong fluorescence. d, During DiffusiOptoPhysiology, a mild $Ca^{2+}$ concentration gradient could be established around the pore vicinity due to thermal motion of ions. Upon binding with Fluo-8, a weaker fluorescence emission than c is expected. e, A cross-sectional view of the spatial distribution of the Fluo-8/$Ca^{2+}$ complex around the pore. Dash box: the zoomed-in view of the immediate vicinity area near the nanopore. f, Top left: corresponding image result from computer simulation. Top right: the simulated fluorescence intensity profile follows a Gaussian distribution. Bottom left: A representative frame acquired from DOP recording for a single WT α-HL nanopore. Bottom right: the corresponding fluorescence intensity profile follows a Gaussian distribution as well. Scale bar: 4 μm. g, Single molecule sensing of TriM-β-CD (75 mM) with an α-HL nanopore during electrode-free oSCR. Scale bar, 4 μm. h, Plot of the reciprocals of the mean inter-event intervals ($1/\tau_{on}$) and mean dwell time ($1/\tau_{off}$) versus TriM-β-CD concentration. The mean and standard deviation comes from three independent experiments for each condition (N=3). i, Statistics of $\tau_{off}$ and $F_p$ results acquired from DOP and electrophysiology recording at +20 mV, respectively. The DOP recording demonstrated above were performed with 1.5 M KCl, 400 μM EDTA, 40 μM Fluo-8, 10 mM HEPES, pH 7.0 in cis and 0.75 M $CaCl_2$, 10 mM HEPES, pH 7.0 in trans. The electrophysiology recordings were performed with 1.5 M KCl, 10 mM HEPES, pH 7.0 in both side of the membrane. TriM-β-CD was added in the cis side with a 75 mM final concentration.
Figure 6:
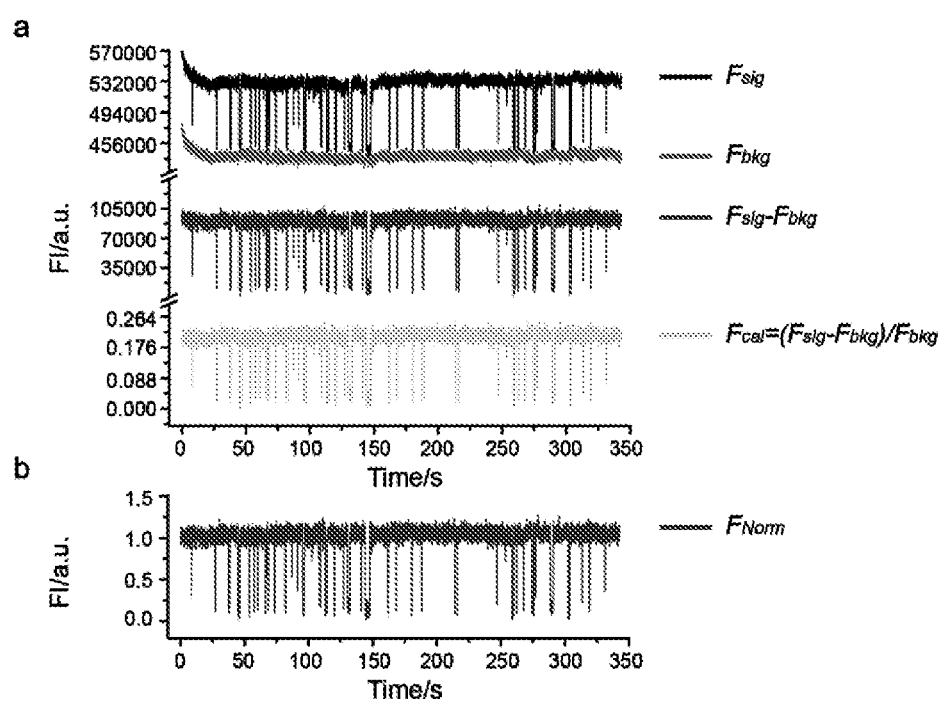

FIG. 6 shows demonstration of fluorescence trace normalization. Due to possible power fluctuations from the laser, drift of the focal plane or motion of the nanopore, low frequency fluctuations are sometimes observed in the raw fluorescence time trace. However, these fluctuations could be diminished by standard trace calibration. a, Calibration of the fluorescence intensities. A sample trace that corresponds to electrode-free oSCR based TriM-βCD sensing was used as a demonstration (FIG. 1). The raw fluorescence time trace (signal and background) was extracted separately using a custom LabVIEW program. See FIG. 10 for the definition of the signal and the background during electrode-free oSCR. Trace calibration is performed according to the formula $F_{cal}=(F_{sig}-F_{bkg})/F_{bkg}$. $F_{cal}$, $F_{sig}$ and $F_{bkg}$ stands for the calibrated fluorescence intensity, the raw fluorescence signal and the raw fluorescence background respectively. Low frequency fluctuations as observed in the raw fluorescence time trace was minimized after the normalization. b, The normalized fluorescence time trace. For quantitative analysis, the amplitude of the fluorescence that corresponds to the open pore state is further normalized to be 1.

Figure 7:
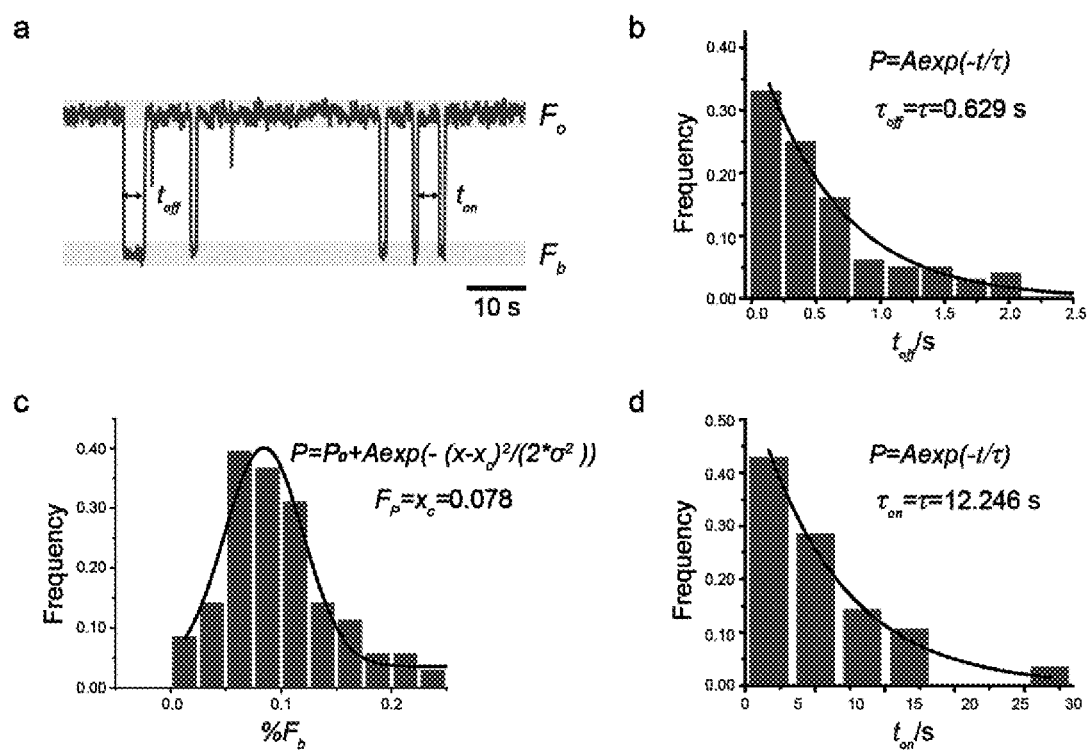

FIG. 7 shows statistics of translocation events. a, A representative fluorescence trace showing TriM-β-CD translocation through an α-HL pore. The event dwell time ($t_{off}$) and the inter-event interval ($t_{on}$) were defined as marked in the trace. b, Histogram of the dwell time ($t_{off}$). The black line is the single exponential fit for the histogram data. The time constant $T_{off}$ was derived from the fitting results. c, Histogram of the blockade level (% $F_b$). The peak value $x_c$ is defined as the mean percentage blockage value $F_p$. d, Histogram of the inter-event intervals ($t_{on}$). The black line is the single exponential fit for the histogram data. The time constant $\tau_{on}$ was derived from the fitting results.

Figure 8:
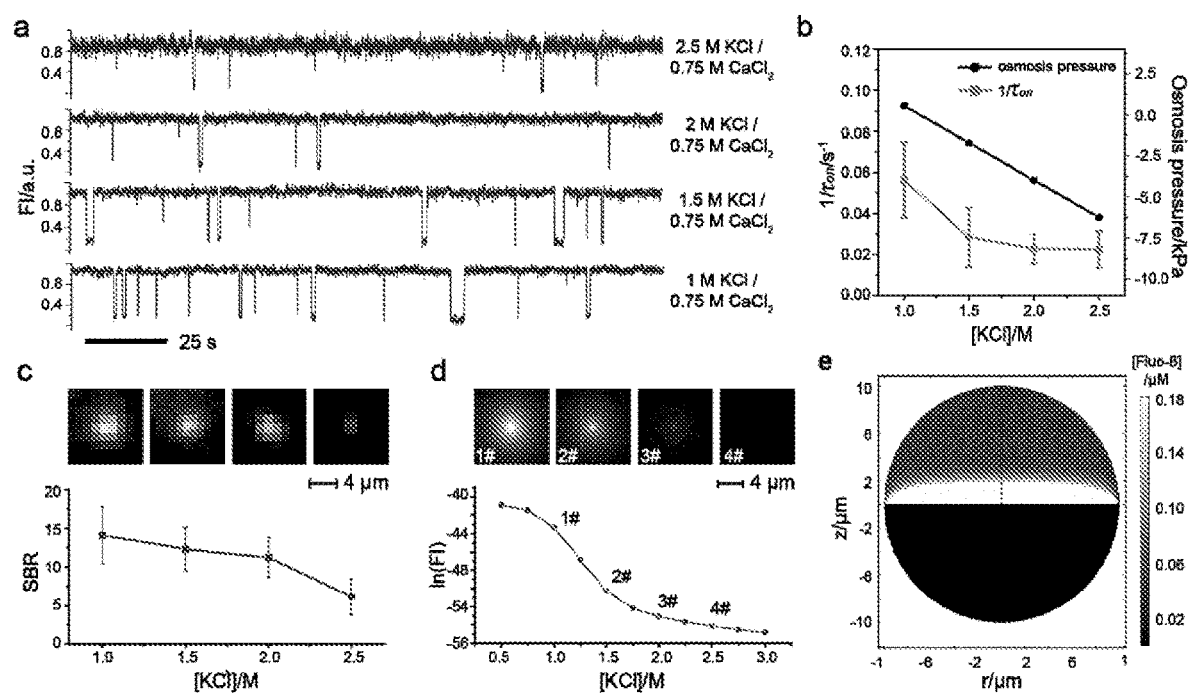

FIG. 8 shows enhanced sensing performance with adjusted osmosis during DOP recording. a, Fluorescence traces acquired from DOP recording with different electrolyte combinations. DOP recordings were performed with α-HL nanopores. TriM-β-CD were added in cis with a final concentration of 15 mM. The inter-event interval $\tau_{on}$ decreases when a larger osmosis gradient between cis and trans was established. b, Plot of the osmotic pressure and $1/\tau_{on}$ as a function of the KCl concentration in cis. The mean and standard deviation comes from three sets of independent experiments (N=3). c, The SBR analysis of fluorescent imaging results with different KCl concentrations in cis. The top panel shows representative images acquired from DOP recordings. The images from left to right were acquired by DOP recording with [KCl] in cis as 1.0, 1.5, 2.0 and 2.5 M, respectively. The value of SBR decreases when KCl concentration in cis increases. The mean and standard deviation comes from five independent experiments (N=5). Experiments in a-c were performed with 1 M-2.5 M KCl, 400 µM EDTA, 40 µM Fluo-8, 10 mM HEPES, pH 7.0 in cis and 0.75 M $CaCl_2$, 10 mM HEPES, pH 7.0 in trans. d, Plot of simulated fluorescence intensity as a function of the KCl concentration in cis. The top panel shows corresponding 2D profiles of fluorescence intensities from the simulation, which resembles the results acquired from electrode-free oSCR in c. The simulations were performed with 1 M-2.5 M KCl in cis and 0.75 M $CaCl_2$ in trans. e, A cross-sectional view of the spatial distribution of Fluo-8 in the simulation space. The boundary condition of the simulation was set as 1.0 M KCl in cis and 0.75 M $CaCl_2$ in trans. Sustained osmotic flow from cis to trans gives rise to an enriched distribution of Fluo-8 in the vicinity of the DIB.

Figure 9:
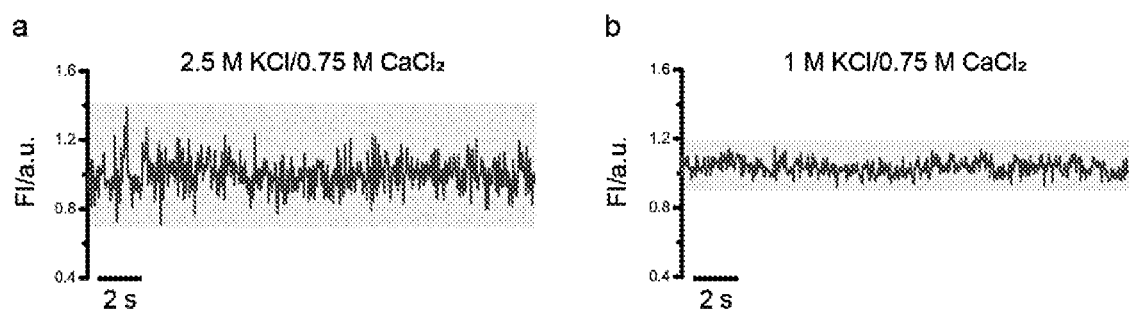

FIG. 9 shows baseline comparison during TriM-β-CD sensing. a, A representative fluorescence trace from DOP recording, acquired with 2.5 M KCl, 400 µM EDTA, 40 µM Fluo-8, 15 mM TriM-β-CD, 10 mM HEPES, pH=7.0 in cis and 0.75 M $CaCl_2$, 10 mM HEPES, pH=7.0 in trans. b, A representative fluorescence trace from DOP recording, acquired with 1 M KCl, 400 µM EDTA, 40 µM Fluo-8, 15 mM TriM-β-CD, 10 mM HEPES (pH=7.0) in cis and 0.75 M $CaCl_2$, 10 mM HEPES, pH=7.0 in trans. Both traces in a and b, were recorded with an α-HL nanopore. The reduction of thermal noises was observed when an osmotic flow from cis to trans exists, which is a consequence of enhanced fluorescence intensity from DOP recording.

Figure 10:
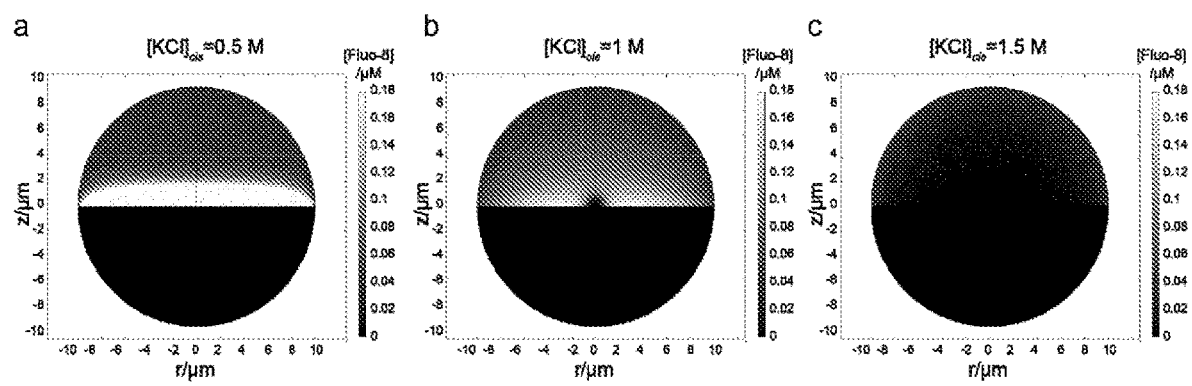

FIG. 10 shows FEM modeling of Fluo-8 distribution. The Fluo-8H placed in cis is a cell-impermeant molecule (AAT bioquest). Osmotic flow of water across the membrane results in the enrichment of Fluo-8 around the cis side of the DIB. This phenomenon should contribute to the enhanced SBR of nanopore fluorescence when the electrolyte osmolarity in cis was set lower than that in trans. The Fluo-8 concentration was simulated using FEM modelling (Methods). For all simulations, the concentration of KCl, EDTA and Fluo-8 on the cis boundary was set to be 0.5-1.5 M, 400 µM and 40 µM, respectively. The concentration of $CaCl_2$ on the trans boundary was kept constant at 0.75 M. These simulation parameters, which were set on the boundary of the simulation space, represent the steady state of the electrolyte buffer that is distant away from the nanopore. a, A cross-sectional view of the 3D distribution of Fluo-8 when the KCl concentration on the cis boundary is 0.5 M. Strong osmotic flow from cis to trans exists in this situation, which results in the enrichment of Fluo-8 near the membrane. b, A cross-sectional view of the 3D distribution of Fluo-8 when the KCl concentration on the cis boundary is 1 M. A decreased enrichment of Fluo-8 is observed. c, A cross-sectional view of the 3D distribution of Fluo-8 when the KCl concentration on the cis boundary is 1.5 M. Weak osmotic flow from trans to cis exists in this condition, which results in reduced Fluo-8 concentration near the membrane.

Figure 11:
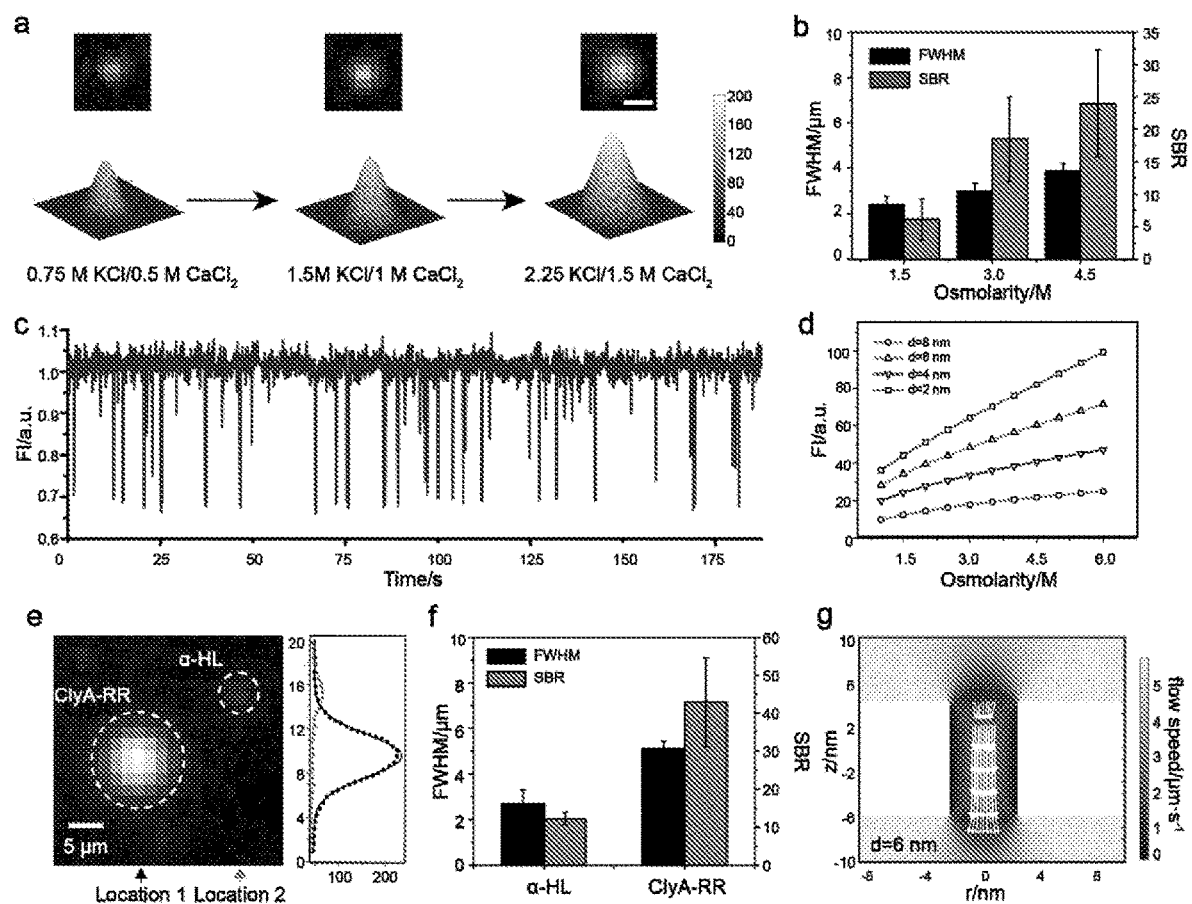

FIG. 11 shows enhanced SBR with increased $Ca^{2+}$ flux during DOP recording. a, Imaging results (Top panel) and the corresponding 2D-Gaussian fittings (Bottom panel) acquired from DOP recording. The $CaCl_2$ concentration in trans was increased when the KCl concentration in cis was adjusted accordingly so that the osmolarity concentration were kept isotonic. The fluorescence spot, which corresponds to $Ca^{2+}$ flux through a WT α-HL nanopore, becomes brighter with an increased $Ca^{2+}$ flux. Scale bar, 4 b, The FWHM and SBR of the fluorescence imaging signals with different electrolyte osmolarity concentrations (N=12). c, A representative fluorescence trace shows PEG1500 translocation signals through a WT α-HL nanopore, as acquired by DOP recording. PEG1500 was added in the agarose substrate reaching a final concentration of 20 mM. A combination of 2.25 M KCl buffer in cis and 1.5 M $CaCl_2$ buffer in trans were used during the DOP recording. d, Simulated total fluorescence intensity as a function of osmolality, shown for four different pore sizes with a diameter of 2 nm, 4 nm, 6 nm and 8 nm, respectively. The electrolyte concentration was kept isotonic to avoid the discussion of osmosis in this demonstration. e, Left: simultaneous DOP imaging of an α-HL and a ClyA-RR. Due to a larger channel conductance, ClyA-RR appears as a larger and brighter spot in comparison with WT α-HL in the same field of view. Right: The fluorescence intensity profile along vertical lines as marked by location 1 and 2, respectively. The fluorescence intensity profile is fitted with a Gaussian distribution. Scale bar, 5 f, The FWHM and SBR of the fluorescence imaging signals of WT α-HL and ClyA-RR (N=5). DOP recordings as demonstrated in e, f were carried out with 1.5 M KCl, 400 µM EDTA, 40 µM Fluo-8, 10 mM HEPES, pH 7.0 in cis and 1.5 M $CaCl_2$, 10 mM HEPES, pH 7.0 in trans. g, Simulated osmosis flow through a virtual cylindrical pore with 6 nm in diameter. A wider pore geometry gives rise to a larger osmosis flow.

Figure 12:
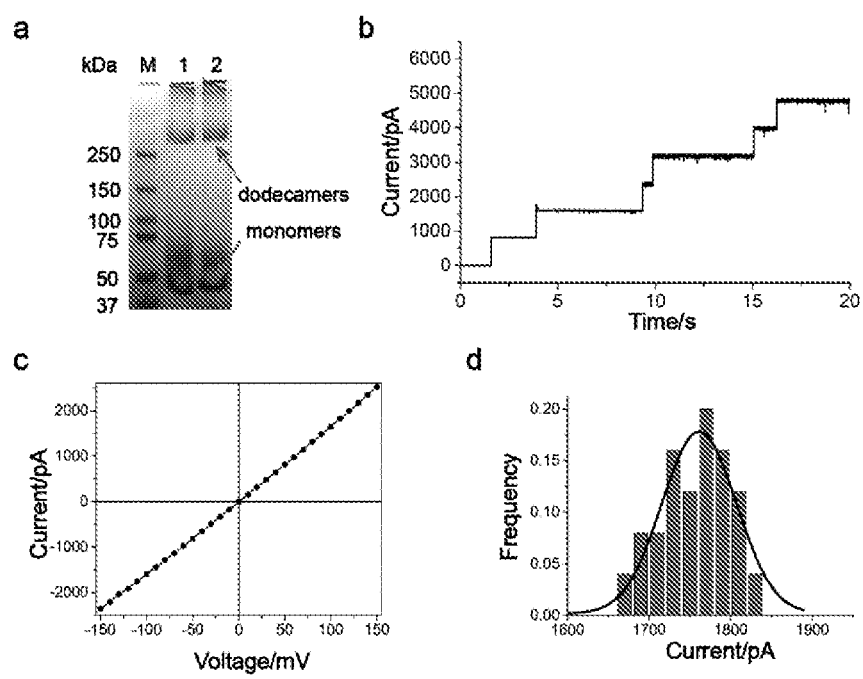

FIG. 12 shows the preparation and characterization of ClyA-RR. a, Dodecameric ClyA-RR characterized using blue native gel electrophoresis (4-15% polyacrylamide gradient gel). Lanes M: precision plus protein standards (Bio-Rad); Lane 1: ClyA-RR prepared using prokaryotic expression (Methods). Lane 2: ClyA-RR after the addition of DDM, reaching a final concentration of 0.25% (w/v). The gel showed that the monomers had been self-assembled before the addition of DDM, but we still use the production with DDM to stabilize dodecameric ClyA-RR. b, Continuous ClyA-RR membrane insertions observed during electrophysiology recording. The measurement was carried out with a +50 mV constant voltage. Dodecameric ClyA-RR nanopores were added in cis. c, A representative I-V curve of a ClyA-RR nanopore. d, The open pore current histogram of ClyA-RR with a +100 mV applied potential. The current was centered at 1761.428 pA. The statistics of open pore current was based on 20 independent sets of electrophysiology recording (N=20). All demonstrated measurements (b-d) were carried out with 1.5 M KCl, 10 mM HEPES, pH 7.0 in both sides of the membrane.

Figure 13:
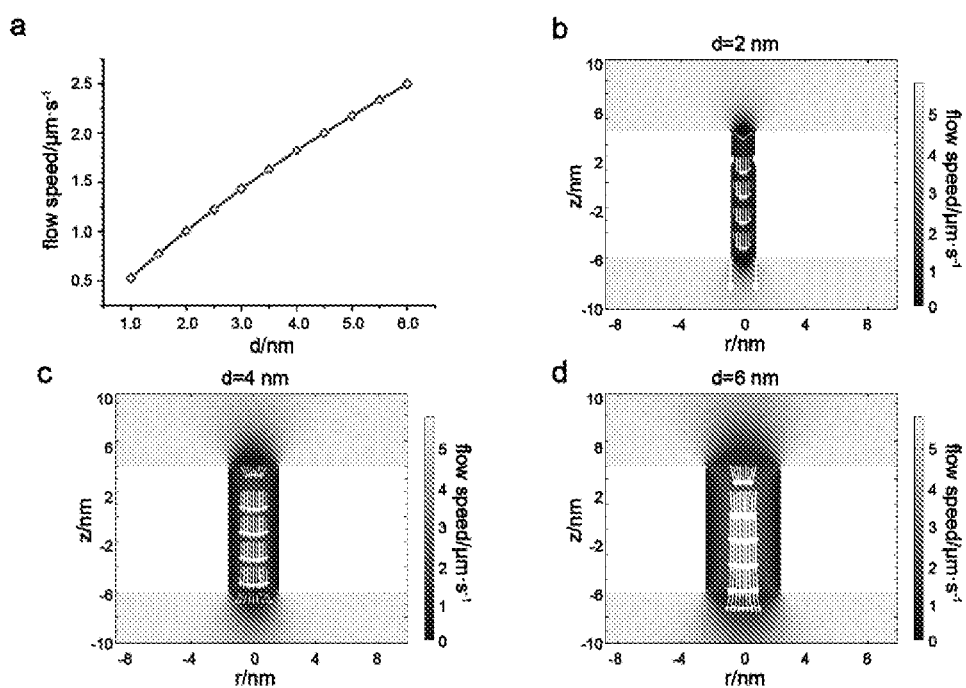

FIG. 13 shows FEM modeling of the osmotic flow in the pore. The simulations were performed with 1 M KCl, 400 μM EDTA, 40 μM Fluo-8 in cis and 1.5 M CaCl$_2$ in trans with varying pore sizes. a, Plot of the flow speed at the center of the pore versus the pore diameter. b-d, The cross-sectional view of the simulated osmotic flow within pores of different sizes. From the simulation, a larger pore diameter results in a significantly increased flow speed.

Figure 14:
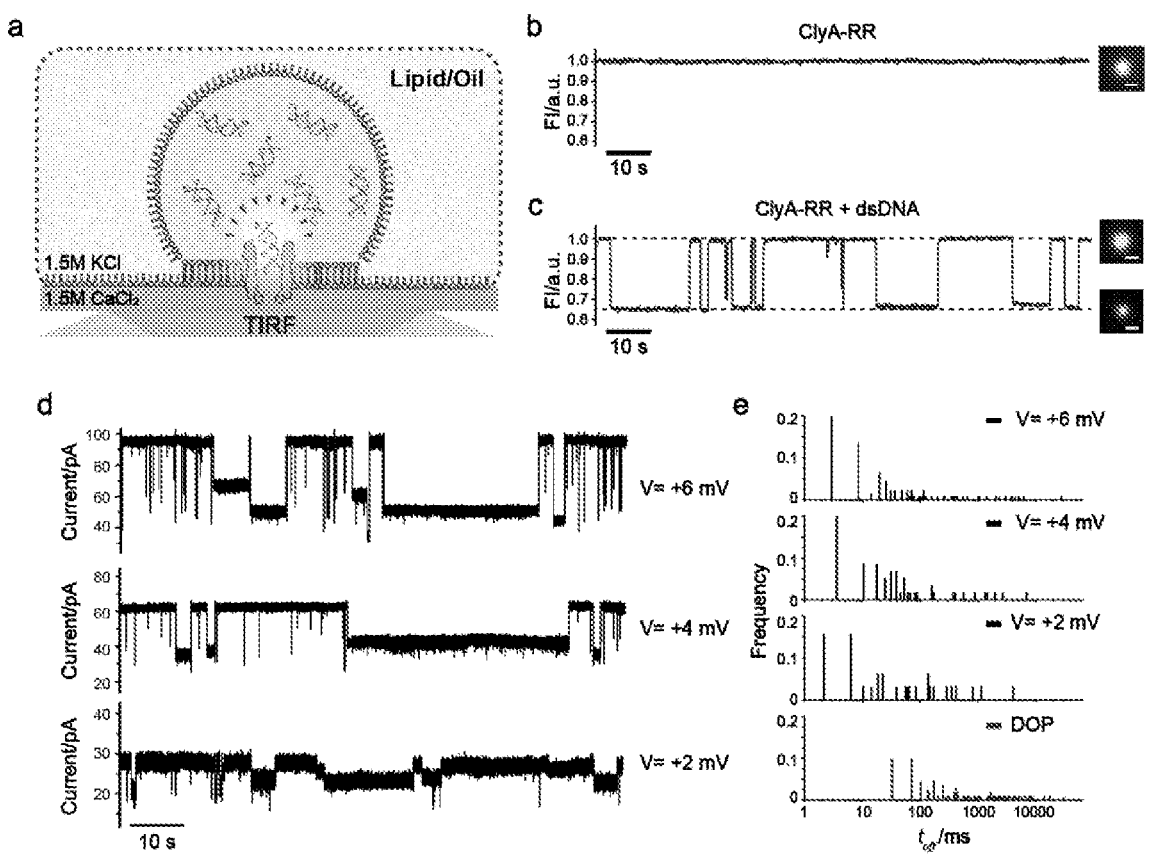

FIG. 14 shows dsDNA translocation through ClyA-RR nanopores. a, The schematic diagram of dsDNA translocation through ClyA-RR during DOP recording. b, DOP imaging of a ClyA-RR nanopore and the corresponding fluorescence trace. No dsDNA was added in the droplet. c, DOP imaging of ClyA-RR nanopore and the corresponding fluorescence trace when dsDNA was added in the droplet with a 2 μM final concentration. Successive deep and long residing fluorescence blockades were clearly observed. Scale bar: 5 μm. d, Electrophysiology recording of dsDNA translocations through a ClyA-RR nanopore at +6 mV, +4 mV and +2 mV, respectively. With voltages as low as +2 mV, current blockages which corresponds to events of dsDNA translocation were still observable. e, Histograms of dwell time for dsDNA translocation events. Due to a limited acquisition time (30 ms) of the EM-CCD, fast dsDNA translocations can't be fully resolved. The DOP recordings demonstrated above were performed with 1.5 M KCl, 400 μM EDTA, 40 μM Fluo-8, 10 mM HEPES, pH 7.0 in cis and 1.5 M CaCl$_2$, 10 mM HEPES, pH 7.0 in trans. The electrophysiology recordings were performed with 1.5 M KCl, 10 mM HEPES, pH 7.0 in cis and 1.5 M CaCl$_2$, 10 mM HEPES, pH 7.0 in trans. dsDNA was add in cis with a 2 μM final concentration. Data from DOP recordings (shown in olive color) were acquired with a frame rate of 30 ms. The electrophysiology trace (shown in black) were recorded with a sampling rate of 25 kHz and low-pass filtered at 1 kHz.

Figure 15:
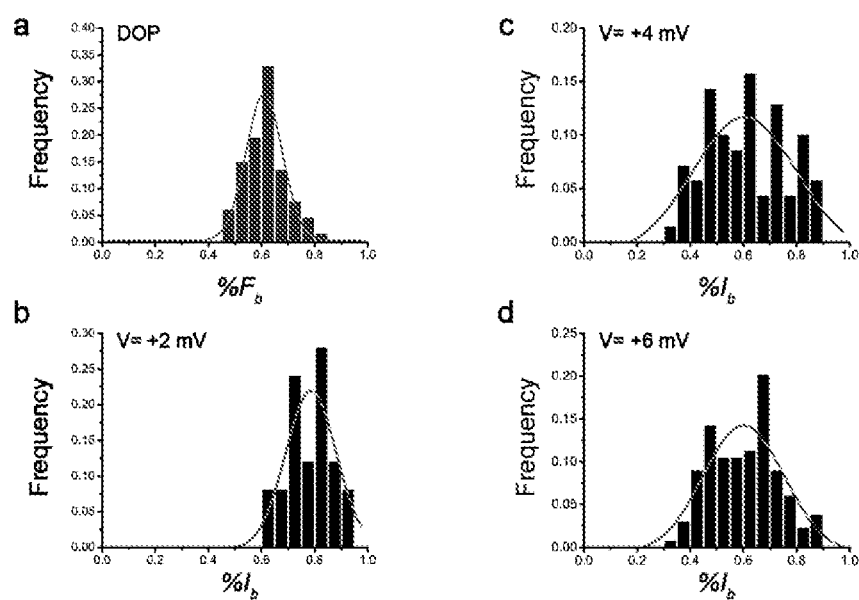

FIG. 15 shows statistics of dsDNA translocation through ClyA. a, Representative histogram of the blockade level (% $F_b$) when dsDNA translocate through a ClyA-RR pore. The $F_p$ value is 0.610±0.138 (center value±FWHM). b-d, Representative histogram of the blockade level (% $I_b$) when dsDNA translocate through a ClyA-RR pore at +2 mV (b), +4 mV (c) and +6 mV(d). The $I_p$ value is 0.786±0.224, 0.605±0.460 and 0.611±0.357, respectively. The optical and electrical blockade levels are essentially identical. Both the electrode-free oSCR and the electrophysiology recording were carried out with 1.5 M KCl, 10 mM HEPES, pH 7.0 in cis and 1.5 M CaCl$_2$, 10 mM HEPES, pH 7.0 in trans. 2 mM 78 bp dsDNA was added in cis.

Figure 16:
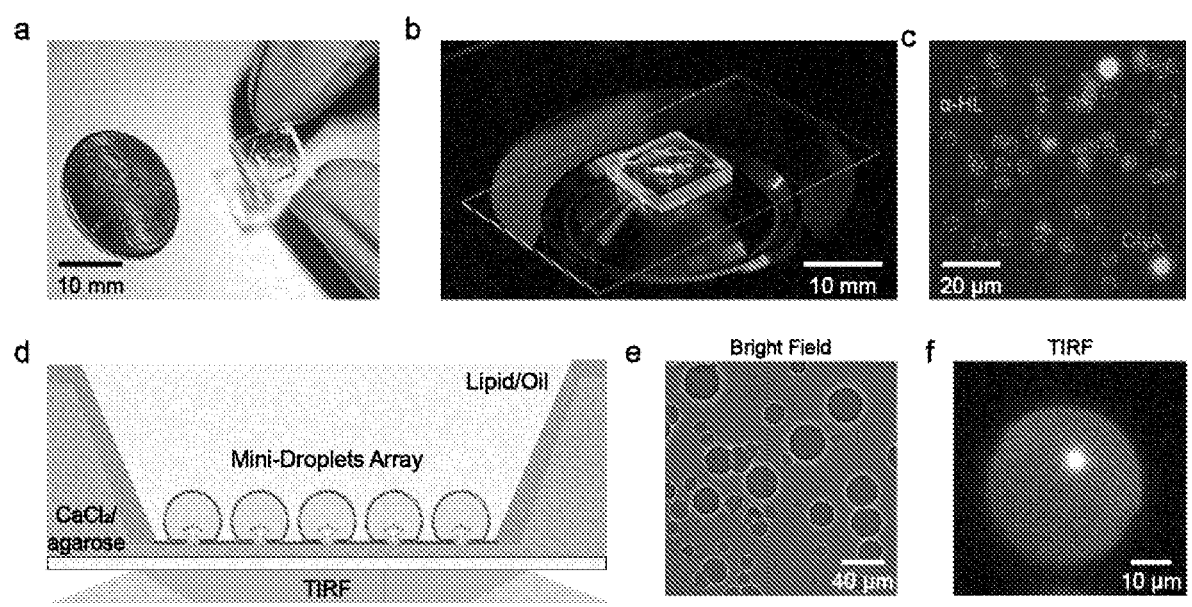

FIG. 16 shows multiplex DOP recording in a miniaturized chip. a, A finger-tip sized device for DOP recording. b, The chip setup during DOP recording. The DIB in the setup was excited using a 473 nm laser and imaged using total internal reflection fluorescence (TIRF) microscopy (Methods). c, Simultaneously imaging of WT α-HL and ClyA-RR nanopores in the same DIB. Two types of nanopores can be easily distinguished from the size and the intensity of the fluorescence spots (yellow dashed circles: WT α-HL, red dash circles: ClyA-RR). d, Schematics of a mini-DIB s array for multiplex electrode-free oSCRs. e, A bright-field image of the mini-DIB array. f, A frame of ClyA-RR nanopore inserted in a mini DIB. The diameter of the DIB is ~40 The DIB was established with 1.5 M KCl, 400 μM EDTA, 40 μM Fluo-8, 10 mM HEPES, pH 7.0 in cis and 1.5 M KCl, 10 mM HEPES, pH 7.0 in trans.

Figure 17:
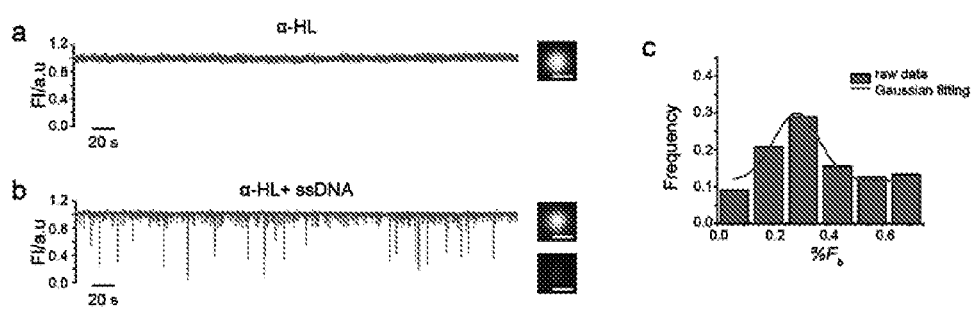

FIG. 17 shows electrode-free ssDNA sensing using α-HL nanopores. (a) A representative DOP acquisition result from an α-HL nanopore and the extracted fluorescence trace. No ssDNA was added in the droplet. (b) A representative DOP acquisition result from an α-HL nanopore and the extracted fluorescence trace when oligomeric ssDNA was added in the droplet with a 50 μM final concentration. Successive short residing fluorescence blockades were consistently and clearly observed. Scale bar in A, B: 5 μm. (c) Statistics of the blockade level (% $F_b$) from the resistive events. The mean value of % F is 0.289±0.175 (center value±FWHM). The demonstrated DOP recordings were performed with 3 M KCl, 400 μM EDTA, 40 μM Fluo-8, 10 mM HEPES, pH 7.0 in cis and 1.5 M CaCl$_2$, 10 mM HEPES, pH 7.0 in trans. DNA sequence used in this assay: 5'-GATAGTGAGC-CAAATTTAAA-3'.

Figure 18:
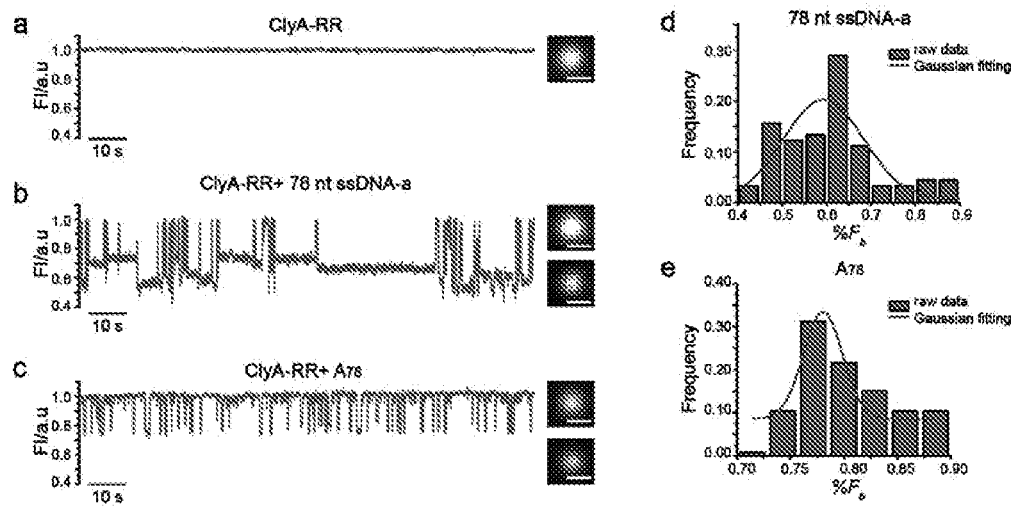

FIG. 18 shows electrode-free ssDNA sensing using ClyA-RR nanopores. (a) DOP imaging of a ClyA-RR nanopore and the corresponding fluorescence trace. No ssDNA was added in the droplet. (b) DOP imaging of a ClyA-RR nanopore and the corresponding fluorescence trace when ssDNA-a (78 nt) was added in the droplet with a 2 μM final concentration. Successive deep and long residing fluorescence blockades were clearly observed. Scale bar in image insets: 5 μm. (c) DOP imaging of a ClyA-RR nanopore and the corresponding fluorescence trace when ploy $A_{78}$ was added in the droplet with a 50 μM final concentration. Successive shallow and short residing fluorescence blockades were clearly observed. Scale bar: 5 μm. (d) Representative histogram of the blockade level (% $F_b$) when ssDNA-a interacted with a ClyA-RR nanopore. The mean value of % F is 0.583±0.014 (center value±FWHM). (e) Representative histogram of the blockade level (% $F_b$) when poly $A_{78}$ interacted with a ClyA-RR nanopore. The mean value of % F is 0.780±0.006 (center value±FWHM). The DOP recordings were performed with 2.25 M KCl, 400 μM EDTA, 40 μM Fluo-8, 10 mM HEPES, pH 7.0 in cis and 1.5 M CaCl$_2$, 10 mM HEPES, pH 7.0 in trans.

Figure 19:
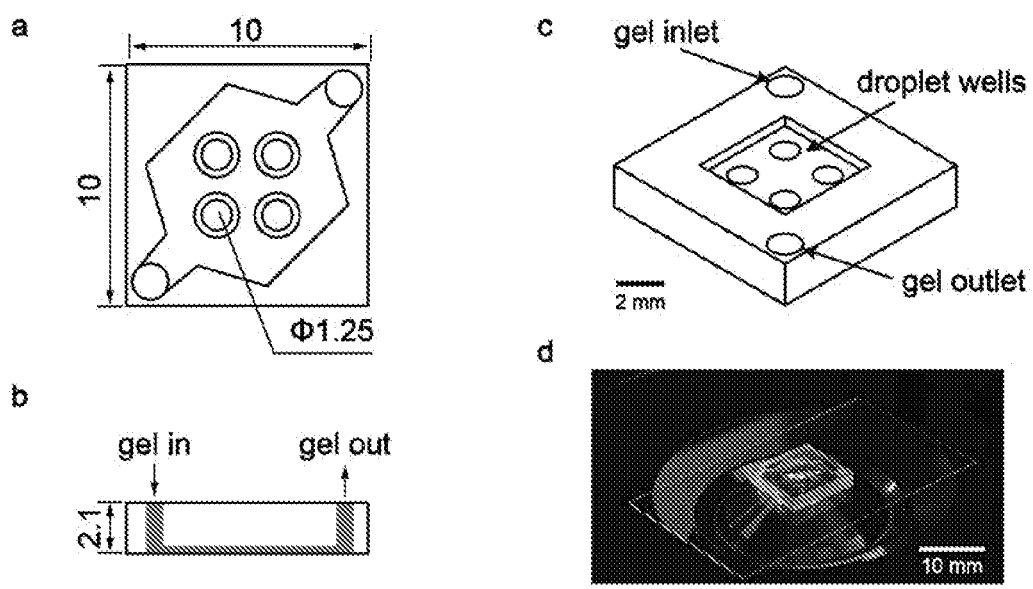

FIG. 19 show the PMMA measurement device. The PMMA device is fabricated as reported before [ref]. (A) Bottom view of the DIB device used in the experiment. Scale unit: mm. (B) Front view of the DIB device used in the experiment. Scale unit: mm. The molten gel can be infused into the device along the route marked in green. (C) 3D model of the DIB device. The gel inlet and outlet holes for molten agarose are shown. The extra hole on the outlet side helps air bubbles to escape during the filling. 4 independent droplet wells are design for parallel measurements. Scale bar: 2 mm. (D) Photograph of a prepared device. The DIB in the setup was excited using a 473 nm laser and imaged using total internal reflection fluorescence (TIRF). Scale bar: 10 mm.

DETAILED DESCRIPTION

The invention is based on DiffusiOptoPhysiology (DOP), which was simplified from oSCR by omitting all electrical connections, optically monitors fluorescence emission resulted from diffusive binding of $Ca^{2+}$ with its indicator dye Fluo-8 through a nanopore sensor (FIG. 1d). Direct sensing of small molecules, macromolecules and biomacromolecules were subsequently demonstrated from direct fluorescence readout. By omitting the need of electrode arrangement, DOP enables parallel measurements from thousands of nanopores with highly accessible and biocompatible materials, which costs <$1 for a single use. New concepts of clinical diagnosis may thus be developed using disposable chips equipped with nanotechnology sensors. The reduced technical barriers from the cost, facilities and skills enable easy carrying out of a nanopore measurement by any researcher with negligible training. Diverse research areas such as high-throughput drug screening or fundamental investigations of ion channels may thus be benefited.

The invention provides a system without electrodes for identifying analytes based on optical measurement of ion flux through pores which is driven by a chemical gradient. The invention also provides a method of using such systems for identifying the analytes, including the methods of identifying a small molecule or a DNA such as dsDNA or ssDNA.

The system without electrodes includes two compartments separated by a membrane: a first compartment holds a first aqueous solution containing a fluorescent reporter molecule, and a second compartment holds a second aqueous solution containing an ionic species which is free. When binding to the ionic species, the fluorescent reporter molecule produces a specific fluorescence emission that can be distinguished by a light sensor. The membrane between the first compartment and the second compartment has at least one nanopore such that the first compartment and the second compartment are connected by the nanopore. The ionic species passes through the nanopore in the membrane from the second compartment to the first compartment driven by a chemical gradient, and binds to the fluorescent reporter molecule in the first compartment, resulting in a fluorescence emission from the reporter molecule. Because passage of the ionic species is limited to the nanopore, this results in a fluorescence in the region proximal to the nanopore. The intensity of the fluorescent signal in the region proximal to the pore is dependent on the rate of flux of the ionic species into the first compartment. Then, the fluorescence emission of the fluorescent reporter molecule can be detected. When the nanopore is blocked or partially blocked by the analyte that are passing through the nanopore, transit of the ionic species through the nanopore is impeded, which is measured as a decrease in fluorescence in the vicinity of the nanopore as compared to the fluorescence resulting from unimpeded flow of the ionic species through the pore. Different analytes impede transit of the ionic species across the nanopore to a different extent, depending on the size, shape, etc., of the analyte, resulting in a decrease in fluorescence of different extent. The decrease in fluorescence due to blockage or partial blockage of the pore correlates with degree to which ionic transit through pore is impeded, which, in turn, reflects information about the properties of the analyte. The magnitude of the decrease in fluorescence in the region proximal to the nanopore can be used to identify the blocking analyte that are passing through the nanopore. The magnitude of the decrease in fluorescence can be characterized by the event dwell time and the percentage blockage depth.

The analyte can be added to the first compartment or the second compartment. The analyte passes through the nanopore, e.g. driven by by a chemical gradient, from the first compartment to the second compartment or from the second compartment to the first compartment and blocks or partially blocks the nanopore, resulting in a decrease in fluorescence.

The method of identifying an analyte comprising:
(a) providing the system of the invention which comprises an analyte in the first compartment or the second compartment;
(b) applying a light capable of exciting the fluorescent reporter molecule to a region in the first compartment proximal to the nanopore;
(c) measuring the fluorescence signal from the fluorescent reporter molecule to identify the analyte.

The ionic species is selected in conjunction with the fluorescent reporter molecule and may be any ionic species that causes a specific fluorescence emission of another molecule. Such ionic species is well known to thos skilled in the art. In some embodiments, the ionic species includes, but does not limit to, $Ag^+$, $Ag^{2+}$, $Al^{3+}$, $As^{3+}$, $Au^+$, $Ba^{2+}$, $Bi^{3+}$, $Ca^{2+}$, $Cd^{2+}$, $Ce^{3+}$, $Ce^{4+}$, $Cl^-$, $Co^{2+}$, $Cr^{3+}$, $Cu^+$, $Cu^{2+}$, $D_y^{3+}$, $Eu^{3+}$, $Fe^{2+}$, $Fe^{3+}$, $Ga^{3+}$, $H^+$, $Hg^+$, $Hg^{2+}$, $In^{3+}$, $K^+$, $La^{3+}$, $Mg^{2+}$, $Mn^{2+}$, $Mo^{3+}$, $Na^+$, $Ni^{2+}$, $OH^-$, $Pb^{2+}$, $Pd^{2+}$, $Pt^{2+}$, $Pt^{4+}$, $Ru^{3+}$, $Sb^{3+}$, $Sc^{3+}$, $Sn^{2+}$, $Sr^{2+}$, $Tb^{3+}$, $Tl^+$, and/or $Zn^{2+}$. The ionic species may be one ionic species or combination of two of more ionic species.

The term "fluorescent reporter molecule" may be any molecule that produces a specific fluorescence emission that can be distinguished by a light sensor when binding to the ionic species, such as listed above. Such fluorescent reporter molecule is well known to those skilled in the art. In some embodiments, the fluorescent reporter molecule may be calcium fluorescent probe, sodium fluorescence probe or zinc fluorescence probe which is a molecule, such as a small molecule, that can chelate calcium ions, sodium ions, or zinc fluorescence respectively. In some embodiments, the fluorescent reporter molecule includes, but does not limit to, Fura-2, Indo-1, Fluo-2, Fluo-3, Fluo-4, Fluo-8, Calcium Green-1, DCFH, DHR, SNARF, Cal-520, calcium-specific aminopolycarboxylic acid or BAPTA (1,2-bis(o-aminophenoxy)ethane-N,N,N',N'-tetraacetic acid). In some embodiments, the fluorescent reporter molecule includes, but does not limit to, SBFI, Asante NaTRIUM Green-1, Asante NaTRIUM Green-2, Thallos Potassium Ion Channel Reagent, Asante Potassium Green-1, Asante Potassium Green-2, Asante Potassium Green-3, PBFI, Fluo-2 Mg, Fura-2 Mg, Indo-1 Mg, Asante Magnesium Green, SPQ, MQAE, TSQ, TFL-Zn, ZINQUIN, etc. The ionic species may be one type of fluorescent reporter molecule or combination of two of more types of fluorescent reporter molecules. The fluorescent reporter molecule may be membrane-impermeant, such as bilayer-impermeant.

In the systems and methods of the invention, the ionic species used should be able to bind to the fluorescent reporter molecule used such that the fluorescent reporter molecule can produce a specific fluorescence emission. In some embodiments, the ionic species is $Ca^{2+}$ and the fluorescent reporter molecule is calcium fluorescent probe, e.g. Fluo-8 or Cal-520.

The first compartment may have the first aqueous solution in it. The second compartment may have the second aqueous solution in it. The first compartment may be completely filled with the first aqueous solution. The first compartment may be not completely filled with the first aqueous solution and there may be some space or other substrate in addition to the first aqueous solution in the first compartment. At least the part in the first compartment that is in close proximity to the membrane is filled with the first aqueous solution. The second compartment may be completely filled with the second aqueous solution. The second compartment may be not completely filled with the second aqueous solution and there may be some space or other substrate in addition to the second aqueous solution in the first compartment. At least the part in the second compartment that is in close proximity to the membrane is filled with the second aqueous solution. The first compartment and the second compartment may be independently in any form or any shape. The form or the shape of the first compartment and the second compartment may be the same or different. In some embodiments, the first compartment and/or the second compartment may or may not have a boundary layer. Each of the boundary layer of the first compartment and the second compartment may be fixed of variable. In some embodiments, the first compartment may be provided by an aqueous droplet. In some embodiments, the second compartment may be provided by a hydrogel layer.

The first aqueous solution comprises the fluorescent reporter molecule. The second aqueous solution comprises the ionic species. The second aqueous solution may comprise salts to provide the ionic species, such as calcium salts. The first aqueous solution and the second aqueous may independently comprise other ingredients or not. The first aqueous solution may not comprise the ionic species that can bind the fluorescent reporter molecule to cause a fluorescence emission. The second aqueous solution may not comprise the fluorescent reporter molecule that can bind to the ionic species and emit fluorescence.

The first aqueous solution may comprise salts that may be different to the salts in the second aqueous solution. The ion in the first aqueous should not bind to the fluorescent reporter molecule to cause it emit fluorescence. The salts in the first aqueous may be any salts that do not bind to the fluorescent reporter molecule to cause it emit fluorescence. In some embodiments, the first aqueous solution comprises sodium chloride. In some embodiments, the first aqueous solution comprises potassium chloride. In some embodiments, the second aqueous solution comprises calcium chloride. The concentration of potassium chloride in the first aqueous solution may be about 0-3.4 M. In some embodiments, the concentration of potassium chloride is less than or equal to 3 M. In some embodiments, the concentration of potassium chloride is less than or equal to 0.75 M, less than or equal to 1.0 M, less than or equal to 1.5 M, less than or equal to 2.25 M, or less than or equal to 2.5 M. The concentration of calcium chloride in the second aqueous solution may be about 0.01-6.76 M. In some embodiments, the concentration of calcium chloride is greater than or equal to 0.15 M, greater than or equal to 0.5 M, greater than or equal to 0.75 M, great than or equal to 1 M, or greater than or equal to 1.5 M, greater than or equal to 2 M, greater than or equal to 3 M, greater than or equal to 4 M, greater than or equal to 5 M, greater than or equal to 6 M. In some embodiments, the concentration of calcium chloride is less than or equal to 6 M, The inventors find that increased concentration of the ionic species could improve the sensing signal by raising the chemical gradient of the ionic species across the membrane and thereby resulting in more ionic species flux through the nanopore. However, the salt concentration is limited by the maximum solubility of electrolytes in water as well (e.g., $CaCl_2$: 6.767 M, at 20° C.). In some embodiments, the first aqueous solution may further comprise a chelating agent for competitive binding of the ion, such as $Ca^{2\pm}$, whereby fluorescence diminishes when away from the center of the nanopore due to the competitive binding. Examples of the chelating agent include, but not limit to, EDTA, BAPTA, EGTA, CyDTA, DTPA, EDDP, HIDA, IDA, NTA, NTPO, TTHA, CA, TA, GA, HEDTA or DEG. In some embodiments, the first aqueous solution or the second aqueous solution may comprise a buffering agent to control pH, for example, Bis-tris, Tris, Hepes, sodium phosphate and/or potassium phosphat. In some embodiments, the first aqueous solution may comprise a potassium chloride buffer (for example 10 mM HEPES, pH 7.0 and KCL) and the second aqueous solution may comprise a calcium chloride buffer (for example, 10 mM HEPES, pH 7.0 and $CaCl_2$). In some embodiments, the first aqueous solution may comprise 1.0 M KCl, 400 μM EDTA, 10 mM HEPES, pH 7.0; 1.5 M KCl, 400 μM EDTA, 10 mM HEPES, pH 7.0; 2.25 M KCl, 400 μM EDTA, 10 mM HEPES, pH 7.0; or 2.5 M KCl, 400 μM EDTA, 10 mM HEPES, pH 7.0. In some embodiments, the second aqueous solution may comprise 0.5 M $CaCl_2$, 10 mM HEPES, pH 7.0; 0.75 M $CaCl_2$, 10 mM HEPES, pH 7.0; 1 M $CaCl_2$, 10 mM HEPES, pH 7.0; or 1.5 M $CaCl_2$, 10 mM HEPES, pH 7.0. Salts may also be included in the first aqueous solution or the second aqueous solution for other reasons, for example, to stabilize proteins, to control binding components, to control the osmolarity/osmolality and/or to activate fluorescent probes.

The first aqueous solution may comprise the analyte. The analyte passes through the nanopore in the membrane from the first compartment to the second compartment driven by chemical gradient, and blocks or partially blocks the nanopore resulting in a decrease in the fluorescence from the fluorescent reported molecule. The analyte may also be comprised in the second aqueous solution, wherein the analyte passes through the nanopore in the membrane from the second compartment to the first compartment driven by chemical gradient, and blocks or partially blocks the nanopore resulting in a decrease in the fluorescence from the fluorescent reported molecule.

In some cases, the first compartment may be provided by an aqueous droplet. The aqueous droplet may comprise or be consisted of the first aqueous solution. In some cases, the second compartment may be provided by a hydrogel layer, such as a hydrogel layer comprising agarose substrate. The hydrogel may comprise the second aqueous solution. When brought together in a hydrophobic medium comprising amphipathic molecules which is selectively permeable to water molecules, the aqueous droplet and the hydrogel layer may spontaneously form a droplet interface bilayer (DIB) consisting of the amphipathic molecules. A protein nanopore may be provided in the aqueous droplet or the hydrogel so that the protein nanopore can spontaneously insert into the DIB while the DIB is forming. The aqueous droplet may also comprise the analyte.

The substrate of the hydrogel layer may comprise or consist of hydrophilic polymer. The substrate of the hydrogel layer may comprise or consist of substantially transparent hydrophilic polymer. The substrate of the hydrogel layer may comprise or consist of agarose. Other hydrogel materials may be suitable, such as polyacrylamide, cross linked polyethylene glycol, or nitro-cellulose. The hydrogel layer may comprises 0.1-20% (w/v) agarose. In some embodiments, the hydrogel layer may comprise less than 5% (w/v) agarose, less than 4% (w/v) agarose or about 3% (w/v) agarose. The hydrogel may comprise greater than 1% (w/v) agarose, greater than 2% (w/v) agarose. The hydrogel may comprise between about 2% and about 4% agarose. The hydrogel may comprise between about 2.5% (w/v) and about 3.5% (w/v) agarose. The hydrogel layer may comprise the analyte.

The membrane separating the first compartment and the second compartment may be any material capable of supporting a nanopore. The membrane may be natural membrane, synthetic membrane or artificial membrane. The membrane may be a solid membrane. The membrane may comprise or consist of a solid substrate, such as SiNx, glass, silicon dioxide, molybdenum disulfide, graphene, aluminium oxide, or CNT (carbon nano tube).

The membrane may be a semipermeable membrane. The semipermeable membrane is selectively permeable to water molecules. The ionic species, the fluorescent reporter molecules, the analytes, etc. are impermeable to the semipermeable membrane, as a result, passage of them is limited to the nanopore. Such semipermeable membrane and its manufacture method are well known to those skilled in the art. The semipermeable membrane may comprise or consist of amphipathic molecules which are selectively permeable to water molecules.

The semipermeable membrane may comprise of consist of amphipathic molecules. The amphipathic molecule may be a lipid or a polymer, such as a block-copolymer. The membrane may be a monolayer or a bilayer, e.g., which may comprise or consist of amphipathic molecules. Examples include a monolayer comprising or consisting of polymers, such as block-copolymers, and a bilayer comprising or consisting of lipids. The bilayer may be a lipid-bilayer. The bilayer may be artificial, for example non-natural. The bilayer may not be a cell bilayer. The bilayer may not be a patch clamp bilayer of a cell. The skilled person will understand that there are multiple methods for providing a bilayer. The bilayer may be provided by a droplet hydrogel bilayer (DHB) method, for example as provided in WO2009024775, the contents of which is incorporated herein by reference.

In some embodiments, the semipermeable membrane may be provided by a first compartment-second compartment interaction in a hydrophobic medium containing amphipathic molecules, such as lipids or block copolymers. In some embodiments, the semipermeable membrane may be provided by immersing the first compartment and the second compartment in a hydrophobic medium containing amphipathic molecules, and bringing the first compartment and the second compartment together such that the amphipathic molecules form a semipermeable membrane. As a result, a semipermeable membrane consisting of the amphipathic molecules will spontaneously form between the first compartment and the second compartment. In some embodiments, a protein nanopore may be provided in the first compartment or the second compartment, when the membrane consisting of the amphipathic molecules spontaneously form, the protein nanopore may spontaneously insert into the bilayer. In some embodiments, the semipermeable membrane may be provided by immersing the first compartment and the second compartment with a protein nanopore in either of them in a hydrophobic medium containing amphipathic molecules, As a result, a semipermeable membrane consisting of the amphipathic molecules will spontaneously form between the first compartment and the second compartment, and the protein nanopore may spontaneously insert into the bilayer.

In some embodiments, the bilayer may be provided by bringing a first compartment having a monolayer of amphipathic molecules into contact with a second compartment having a monolayer of amphipathic molecules to spontaneously form a bilayer. In some embodiments, the bilayer may be provided by immersing the first compartment and the second compartment with a protein nanopore in either of them in a hydrophobic medium containing amphipathic molecules, thereby forming a monolayer of amphipathic molecules on the surfaces of the first compartment and the second compartment, then bringing the first compartment and the second compartment together such that the monolayers of amphipathic molecules form a bilayer. As a result, a bilayer consisting of the amphipathic molecules will spontaneously form between the first compartment and the second compartment, and the protein nanopore may spontaneously insert into the bilayer.

Therefore, in one aspect of the invention, a method of manufacturing above system is provided, comprising:
    providing a first compartment having a first aqueous solution in it, wherein the first aqueous solution comprises a fluorescent reporter molecule capable of emitting fluorescence when bound to an ionic species;
    providing a second compartment having a second aqueous solution in it, wherein the second aqueous solution comprises the ionic species which specifically bound to said fluorescence reporter molecule;
    bringing the first compartment and the second compartment together in a hydrophobic medium containing amphipathic molecules such that a semipermeable membrane with an inserted nanopore is formed between the first compartment and the second compartment;
    wherein a protein nanopore is provide in the first aqueous solution or the second aqueous solution
    wherein a semipermeable membrane consisting of the amphipathic molecules will spontaneously form between the first compartment and the second compartment and the protein nanopore may spontaneously insert into the semipermeable membrane;

The first compartment, the second compartment, the fluorescent reporter molecules, the ionic species, the protein nanopore, the semipermeable membrane, the bilayer, the hydrophobic medium, the amphipathic molecules, the analyte and other features mentioned here are as described in the context of this description.

In the present invention, the analyte may be provided in the first aqueous solution or the second aqueous solution before the semipermeable membrane forms. The analyte may also be added in the first aqueous solution or the second aqueous solution after the semipermeable membrane forms and before the detection initiates.

In some embodiments, the amphipathic molecules may be selectively permeable to water molecules. The amphipathic molecules used in any method of the invention may be polymers or lipid molecules, in particular, surfactant molecules may be used. The lipid molecule may be selected from the group comprising fatty acyls, glycerolipids, glycerophospholipids, sphingolipids, sterol lipids, prenollipids, saccharolipids, polyketides, phospholipids, glycolipids and cholesterol. The lipid may include any of the group comprising monoolein; 1,2-dioleoyl-sn glycero-S-phosphocholine (DOPC); 1,2-diphytanoyl-sn-glycero-3-phosphatidylcholine (DPhPC); palmitoyl oleoyl phosphatidylcholine (POPC); 1-palmitoyl-2-oleoyl phosphatidylethanolamine (POPE); 1-palmitoyl-2-oleoyl-phosphatidylethanolamine; and 1-palmitoyl-2-oleoylphosphatidylglycerol (POPE/POPG) mixtures; or mixtures thereof.

The polymer may be a block-copolymer capable of forming a semipermeable membrane, e.g. a triblock copolymer, for example as provided in Discher, D. E. & Ahmed, F. Polymersomes. Annu. Rev. Biomed. Eng. 8, 323-341 (2006); Nardin. C., Winterhalter, M. & Meier. W. Giant free-standing ABA triblock copolymer membranes. *Langmuir* 16, 7708-7712 (2000); Meier, W, Nardin, C. &. Winterhalter, M. Reconstitution of channel proteins in (polymerized) ABA triblock copolymer membranes. *Angew. Chem. Inn Ed.* 39, 4599-4602 (2000) or CN104936682B; incorporated herein by reference. In one embodiments, the triblock copolymer is poly(2-methyloxazolin)-block-poly(dimethysiloxane)-block-poly(2-methyloxazoline) (PMOXA-PDMS-PMOXA) or poly(2-methyloxazolin)-block-poly(ethylene)-block-poly(2-methyloxazoline) (PMOXA-PE-PMOXA).

The hydrophobic medium may comprise oil. In some embodiments, the hydrophobic medium may be an oil. The hydrophobic medium comprising amphipathic molecules may comprise or consist of lipid-in-oil. The oil may be a hydrocarbon, which may be branched or unbranched, and may be substituted or unsubstituted. For example, the hydrocarbon may have from 5 to 20 carbon atoms, more preferably from 10 to 17 carbon atoms. Suitable oils include alkanes or alkenes, such as hexadecane, decane, pentane or squalene, or fluorinated oils, or silicone based oils, or carbon tetrachloride; or mixtures thereof. In some embodiments, the oil is an n alkane, such as a C10 to C17 n-alkane, e.g. n-hexadecane (C16). In some embodiments, the hydrophobic medium may be an oil, e.g., a mixture a hexadecane and silicone oil. In some embodiments, the oil may comprise a 1:1 (v:v) mixture of hexadecane and silicone oil AR20 (Sigma-Aldrich).

Alternatively, other bilayer forming methods are available. For example, the bilayer may be provided by any one of the following techniques known to the skilled person comprising: patch clamping, for example optical patch clamping; black lipid membrane (BLM); otherwise known as painted BLM; Supported lipid bilayers (SLB); and tethered bilayer lipid membranes (t-BLM). The bilayer may be formed across an aperture in accordance with WO2008102121, the content of which is incorporated herein by reference. The bilayer may be formed at droplet to droplet interfaces in accordance with WO2014064444, the content of which is incorporated herein by reference.

In the invention, the term "nanopore" refers to a channel having an opening at its narrowest point having a diameter, which permits the analyte pass through the opening. The nanopore is narrow enough that the blockage of the channel by the analyte can be detected by a change in a particular signal, for example, fluorescence signal.

The nanopore in the membrane can vary in size depending on the intended application of the system but must be large enough to allow passage of ions of the ionic species used in the invention. Preferably, the nanopore is also small enough to prevent passage of the fluorescent reporter molecule. The nanopore may be large enough to allow passage of the analyte.

The nanopore may be a solid nanopore, a protein nanopore of a DNA nanopore whether the membrane is a solid membrane or a semipermeable membrane. The nanopore may be natural, for example derived from a biological organism, or the nanopore may be synthetic. The nanopore may be recombinantly produced. The nanopore may be a biological molecule, such as a protein nanopore (also can be called a nanopore-forming protein). In some cases, the nanopore may be formed by protein which may be referred to as a protein nanopore or a nanopore-forming protein. The protein nanopore used in this invention preferably has no spontaneous gating activities and/or preferably keeps open when the analyte is absent. The protein nanopore used in this invention may be any. Examples of protein nanopore or nanopore-forming protein include α-HL, ClyA, Phi29 connector protein, aerolysine, MspA, OmpF, OmpG, FraC, HlyA, SheA, sp1 or variants thereof. In some embodiments, one or more nanopores are ClyA-RR[42]. ClyA-RR is a mutant of ClyA (D64R/C87A/L99Q/E103G/S110R/F166Y/I203V/C285S/K294R/H307Y). Other examples of biological molecule nanopores include nanopores formed by DNA self-assembly. The nanopore that can be used in the invention may also be ion channel, such as potassium channel or sodium channel and the like.

In the invention, the term "α-HL" may also referred to as α-hemolysin, may be selected from the group consisting of a wild-type α-hemolysin, a mutant α-hemolysin, a wild-type α-hemolysin paralog or homolog hemolysin, and a mutant α-hemolysin paralog or homolog hemolysin. In some embodiments, α-hemolysin may be the wild-type α-hemolysin. The α-hemolysin that may be used in the invention should be capable of forming nanopore. In some embodiments, α-HL is heptameric.

In the invention, the term "ClyA" may be selected from the group consisting of a wild-type ClyA, a mutant ClyA, a wild-type ClyA paralog or homolog ClyA, and a mutant ClyA paralog or homolog ClyA. In some embodiments, ClyA may be the wild-type α-hemolysin. In some embodiments, ClyA may be a mutant ClyA. A preferred mutant ClyA is ClyA-RR. The ClyA that may be used in the invention should be capable of forming nanopore. In some embodiments, ClyA or ClyA-RR is dodecameric.

Sequences of protein nanopores, e.g., α-HL and ClyA or their mutants, are known by the person skilled in the art. The preparation method of protein nanopores, e.g., α-HL or ClyA or their mutants is known by the person skilled in the art, for example, it could be prepared by prokaryote expression and easily purified by gel-electrophoresis or chromatography. Protein nanopore can be formed by self-assembly of several protein monomers, e.g., dodecameric ClyA, dodecameric ClyA-RR or heptameric α-HL. In some cases, the protein nanopore can self-assemble into the semipermeable membrane.

The nanopore may be a solid-state nanopore, for example comprising synthetic materials such as silicon nitride or graphene. A solid-state nanopore is typically a nanometer-sized hole formed in a synthetic membrane (such as SiNx or $SiO_2$). The solid-state nanopore can be fabricated by focused ion or electron beams, allowing the size of the pore to be tuned. The nanopore may be a hybrid nanopore comprising a pore-forming protein set in synthetic material.

Methods of forming nanopores in a membrane are well known to those skilled in the art, e.g., by adding nanopore molecules to the semipermeable membrane after the semipermeable membrane is formed or during formation of the semipermeable membrane. In some embodiments, a protein nanopore may be provided in the first compartment or the second compartment, when the membrane consisting of the amphipathic molecules spontaneously form, the protein nanopore may spontaneously insert into the semipermeable membrane.

The analyte is not limited to a specific molecule and may be any molecule capable of blocking or partially blocking the nanopore when passing through the nanopore. The analyte may include, but be not limited to, a small molecule, a macromolecule or a bio-macromolecule. A small molecule means a molecule or an ion with low molecular weight and small size, which is much smaller than the pore size of the nanopore and easily pass through the nanopore. A small molecule may include, but be not limited to, a compound, a drug, a sugar, an ion, a neurotransmitter, an amino acid or a nucleotide. A macromolecule means a very large molecule and is typically composed of thousands of atoms or more. A macromolecule may include, but be not limited to, a biopolymer such as nucleic acid, protein, carbohydrate or lipid; a large non-polymeric molecule such as lipid or macrocycle; or synthetic macromolecule. An example of the macromolecule is a bio-macromolecule which includes, but be not limited to, a polypeptide, a polysaccharide, or a polynucleotide, e.g., a DNA (including ssDNA or dsDNA) or RNA (including miRNA, siRNA or tRNA). The length of the DNA such as ssDNA or dsDNA may be 10-1000nt. The length of the DNA such as ssDNA or dsDNA may be greater than 15 nt, greater than 20 nt, greater than 30 nt, greater than 40 nt, greater than 50 nt, greater than 60 nt, greater than 70 nt, greater than 80 nt, greater than 90 nt, or greater than 100 nt. The length of the DNA such as ssDNA or dsDNA may be less than 500 nt, less than 4000 nt, less than 300 nt, less than 200 nt. The length of the RNA such as miRNA, siRNA or tRNA may be greater than 15 nt, greater than 20 nt, greater than 30 nt, greater than 40 nt, greater than 50 nt, greater than 60 nt, greater than 70 nt, greater than 80 nt, greater than 90 nt, or greater than 100 nt. The length of the RNA such as miRNA, siRNA or tRNA may be less than 500 nt, less than 4000 nt, less than 300 nt, less than 200 nt.

The analyte may be placed in the first aqueous solution or in the second aqueous solution. The analyte may be comprised in the first aqueous solution or the second aqueous solution at the time the first aqueous solution or the second aqueous solution is formulated, that is, the analyte may be formulated into the first aqueous solution or the second aqueous solution together with other desired ingredients. The analyte may be added to the first aqueous solution or the second aqueous solution after the system is ready and when the test is to be initiated.

In this invention, the term "identifying" includes detecting or analyzing the identity, e.g., the type of the analyte or obtaining the structure information of the analyte, e.g., the structure of the polymer, or the structure of the polynucleotide or polypeptide, such as the primary structure or the secondary structure of the polynucleotide.

The blocking analyte that are passing through the nanopore can be identified by the magnitude of the decrease in fluorescence in the region proximal to the nanopore. Upon the disclosure of the invention, it is known to those skilled in the art how to identify the analyte based on the magnitude of the decrease in fluorescence, which, for example, can be characterized by the event dwell time and the percentage blockage depth. Event dwell time is the residual time that an analyte is occupying the nanopore. Percentage blockage depth is defined as $I_b/I_o$ where $I_b$ and $I°$ stands for the absolute blockage current and the open pore current respectively. For example, a fluorescence emission resulting from impeded flow of the ionic can be measured and compared with the fluorescence emission of reference substance under the same testing conditions to determine whether the analyte and the reference are identical. The event dwell time and/or the percentage blockage depth of the fluorescence emission can be the items that are compared.

Fluorescence detection may comprise microscopy or spectroscopy of the membrane and membrane region. Fluorescence detection may comprise the use of Total Internal Reflection Fluorescence (TIRF), wide field fluorescence microscopy or confocal microscopy. Fluorescence detection may comprise the use of HiLo microscopy, for example as provided by Tokunaga et al (2008. Highly inclined thin illumination enables clear single-molecule imaging in cells. Nat Meth 5, 159-161). Fluorescence detection may comprise the use of other glancing-incidence illumination techniques. Any suitable Fluorescence detection means may be used to detect fluorescence signals/emission in the membrane region immediately surrounding the membrane and nanopores in the membrane. Fluorescence detection may comprise the use of surface plasmon resonance. Fluorescence detection may comprise the use of super-resolution microscopy, such as deterministic super-resolution, including STED, GSD, RESOLFT or SSIM; or stochastically super-resolution, including SOFI, or single-molecule localization methods (SMLM) such as SPDM, SPDMphymod, PALM, FPALM, STORM or dSTORM. Fluorescence detection may comprise the use of epifluorescence microscopy, confocal laser scanning microscopy (LSM), or total internal reflection fluorescence (TIRF) microscopy. Fluorescence detection may comprise the use of fluorescence correlation spectroscopy (FCS). Image correlation spectroscopy (ICS) may be used to calculate the spatial correlation function of the fluctuations in fluorescence intensity of an image, which can be acquired by confocal or two-photon LSM or with TIRF microscopy. Fluorescence detection techniques may be described in Ana J. Garcia-Saez, Petra Schwille. Surface analysis of membrane dynamics Biochimica et Biophysica Acta 1798 (2010) 766-776, the content of which is incorporated by reference.

Detection of fluorescence emission from the fluorescent reporter molecule may require a light source and light sensor. The light source and light sensor may be contained in the same device or in separate devices. The light source should be capable of providing light of a wavelength or range of wavelengths capable of exciting the fluorescent reporter molecule in the presence of the ionic species, and the light sensor should be capable of detecting light of a wavelength or range of wavelengths emitted by the fluorescent reporter molecule in the presence of the ionic species.

Therefore, in some embodiments, the system includes a light source capable of illuminating a region of the membrane proximal to the nanopores. In some embodiments, the light source provides light within a specified range of wavelengths. In some embodiments, the light source may be a laser, a LED, a halogen light or a xenon light. It is known to those skilled in the art how to illuminate a fluorescent reporter molecule with a light source.

In some embodiments, the system includes a light sensor capable of detecting an optical signal in a region of the membrane proximal to the nanopores. The light sensor may be a photosensitive device which is sensitive to low light (i.e. fluorescence), such as a charge-coupled device (CCD), an electron multiplying CCD (EMCCD), a sCMOS sensor or a photodiode, such as Avalanche Photodiode (APD). A fast photosensitive device is preferred. Preferably, the light sensor is a EMCCD or Avalanche Photodiode (APD).

The light sensor may also be a microscopic imaging system, a photomultiplier, or a light sensor that can detect the fluorescence using the above fluorescence detection technology. In some embodiments, a total internal reflection fluorescence (TIRF) imaging system, such as a total internal reflection fluorescence microscope (TIRFM) may be used to detect and/or recording the optical signal in the region of the membrane proximal to the nanopores. In some embodiments, a wide field fluorescence imaging system or confocal imaging system may be used to detect and/or recording the optical signal in the region of the membrane proximal to the nanopores. It is known to those skilled in the art how to detect the fluorescence emission from the fluorescent reporter molecule with a light sensor.

In some embodiments, the light sensor and the light sensor may be a single device. Some fluorescence detection device may also be used for illumination. For example, TIRFM could used both for illumination and imaging.

The inventors find that the osmotic flow between the first compartment and the second compartment is advantageous for further improving the fluorescence detection of the analyte by the nanopore. The osmolarity/osmolality difference between the first compartment and the second compartment may drive an oriented flow of water carrying ions and analytes through a biological nanopore which is inserted in the membrane. As a result, an enhanced translocation efficiency for analyte should be achieved with this introduced asymmetry. Additionally, the fluorescence signal can be amplified by the osmotic flow between the first compartment and the second compartment. When the osmolarity (or osmolality) of the second aqueous solution is higher than the osmolarity (or osmolality) of the first aqueous solution, due to the fact that the fluorescent reporter molecule, which is impermeable to the semipermeable membrane, osmotic flow of water across the membrane results in the enrichment of the fluorescent reporter molecule around the membrane in the first compartment and consequently the fluorescence intensity is enhanced.

Therefore, although in some embodiments, the method of the invention can be implemented in an environment where the the first aqueous solution and the second aqueous solution are kept isotonic or where the osmolarity (or osmolality) of the second aqueous solution is lower than the osmolarity (or osmolality) of the first aqueous solution, in some embodiments, the osmolarity (or osmolality) of the second aqueous solution may be higher or lower than the osmolarity (or osmolality) of the first aqueous solution.

Both osmolarity and osmolality are defined in terms of osmoles osmole is a unit of measurement that describes the number of moles of a compound that contribute to the osmotic pressure of a chemical solution, i.e., the hydrostatic pressure resulting from a concentration gradient across two sides of a surface, such as across a semi-permeable membrane. Osmolarity is defined as the number of osmoles of solute per volume of solution. It is commonly expressed. in terms of osmol/L. Osmolality is very similar, but it is defined as the number of osmoles of solute per kilogram of pure solvent and is commonly expressed in terms of osmol/kg. For example, a solution of 1 mol/L, NaCl corresponds to an osmolarity of 2 osmol/L. The NaCl salt particle dissociates fully in water to become two separate particles: a $Na^+$ ion and a $Cl^-$ ion. Therefore, each mole of NaCl becomes two osmoles in solution, one mole of $Na^+$ ion and one mole of $Cl^-$. Similarly, a solution of 1 mol/L. $CaCl_2$), gives a solution of 3 osmol/L ($Ca^{2+}$ and 2 $Cl^-$), It is well known to those skilled in the art how to determine the osmolarity or the osmolality of a solution.

The osmolarity/osmolality of the second aqueous solution may be increased by increasing the concentration of the ionic species or by additionally adding other solute which can increase the osmolarity/osmolality in the first aqueous solution. Preferably, the osmolarity/osmolality the second aqueous solution is increased by increasing the concentration uf the ionic species because increased concentration of the ionic species could improve the sensing signal. The osmolarity/osmolality of the first aqueous solution may be decreased by decreasing the concentration of the solute that can contribute to the osmotic pressure or even no salts in the first aqueous solution. In some embodiments, the osmolarity of the second aqueous solution is at least 0.01 osmol/L, at least 0.05 osmol/L, at least 0.1 osmol/L, at least 0.2 osmol/L, at least 0.3 osmol/L, at least 0.4 osmol/L, at least 0.5 osmol/L, at least 0.6 osmol/L, at least 0.7 osmol/L, at least 0.8 osmol/L, at least 0.9 osmol/L, at least 1.0 osmol/L, at least 1.5 osmol/L, at least 2.0 osmol/L. at least 2.5 osmol/L, at least 3.0 osmol/L, at least 3.5 osmoL/L. at least 4.0 osmol/L, at least 4.5 osmol/L, at least 5.0 osmol/L, at least 5.5 osmol/L, at least 6.0 osmol/L, at least 6.5 osmol/L, at least 7.0 osmol/L, at least 7.5 osmol/L, at least 8.0 osmol/L, at least 8.5 osmol/L, at least 9.0 osmol/L, at least 9.5 osmol/L, at least 10 osmol/L. at least 11 osmol/L. at least 12 osmol/L, at least 13 osmol/L, at least 14 osmol/L, at least 15 osmol/L, at least 16 osmol/L, at least 17 osmol/L, at least 18 osmol/L, at least 19 osmol/L or at least 20 osmol/L higher than that of the first aqueous solution. In some embodiments, the osmolality of the second aqueous solution is at least 0.01 osmol/kg, at least 0.05 osmol/kg, at least 0.1 osmol/kg, at least 0.2 osmol/kg, at least 0.3 osmol/kg, at least 0.4 osmol/kg, at least 0.5 osmol/kg, at least 0.6 osmol/kg, at least 0.7 osmol/kg, at least 0.8 osmol/kg, at least 0.9 osmol/kg, at least 1.0 osmol/kg, at least 1.5 osmol/kg, at least 2.0 osmol/kg, at least 2.5 osmol/kg, at least 3.0 osmol/kg, at least 3.5 osmol/kg, at least 4.0 osmol/kg, at least 4.5 osmol/kg, at least 5.0 osmol/kg, at least 5.5 osmol/kg, at least 6.0 osmol/kg, at least 6.5 osmol/kg, at least 7.0 osmol/kg, at least 7.5 osmol/kg, at least 8.0 osmol/kg, at least 8.5 osmol/kg, at least 9.0 osmol/kg, at least 9.5 osmol/kg, at least 10 osmol/kg, at least 11 osmol/kg, at least 12 osmol/kg, at least 13 osmol/kg, at least 14 osmol/kg, at least 15 osmol/kg, at least 16 osmol/kg, at least 17 osmol/kg, at least 18 osmol/kg, at least 19 osmol/kg or at least 20 osmol/kg higher than that of the first aqueous solution.

By measuring the fluorescence emitted from the fluorescent reporter molecule, the present invention enables record of the flux through many nanopores in parallel without the need for expensive arrays of electrodes. The measured fluorescence can be separated into multiple fluorescent traces for each nanopore and can be applied to the situation that require high throughput screening such as a nanopore array.

In another aspect of the invention, a nanopore array without electrodes is provided. The nanopore array include multiple systems of the invention in parallel, each system are as described above. The nanopore array can be used to identify multiple analytes in parallel. The nanopore array of the invention can be used without electrodes, thereby reducing the size of the device and saving costs.

The multiple systems are arranged such that the measured fluorescence can be distinguished for each system. At least parts of these multiple systems are separated from each other such that each system can be used independently to detect the analyte in it and the measured fluorescence can be distinguished for each system. In some embodiments, at least the first compartments of the multiple systems are separated from each other. In some embodiments, the second compartments of the multiple systems are separated or not separated from each other. The multiple systems may be the same of different.

The density of the systems in the nanopore array may be up to 10 per $mm^2$, up to 50 per $mm^2$, up to 100 per $mm^2$, up to 200 per $mm^2$, up to 300 per $mm^2$, up to 400 per $mm^2$, up to 500 per $mm^2$, up to 600 per $mm^2$, up to 700 per $mm^2$, up to 800 per $mm^2$, up to 900 per $mm^2$, up to 1000 per $mm^2$ or more.

The total area provided by the multiple systems may be up to 1 $mm^2$, up to 2 $mm^2$, up to 5 $mm^2$, up to 10 $mm^2$, up to 15 $mm^2$, up to 20 $mm^2$, up to 25 $mm^2$, up to 30 $mm^2$, up to 35 $mm^2$, $mm^2$, up to 40 $mm^2$, up to 45 $mm^2$, up to 50 $mm^2$, up to 55 $mm^2$, up to 60 $mm^2$, up to 65 $mm^2$, up to 70 $mm^2$, up to 75 $mm^2$, up to 80 $mm^2$, up to 85 $mm^2$, up to 90 $mm^2$, up to 95 $mm^2$, or up to 100 $mm^2$ or more.

Multiple analytes can be provided in two or more, or each, system of the array such that the multiple analytes are physically separated into various systems. The multiple analytes may be the same or different, or may be partially identical or partially different. In some embodiments, at least two of the multiple analytes may be different. In some embodiments, the same analytes may be provided in two or more, or each, system of the array. In some embodiments, different analytes may be provided in two or more, or each, system of the array. In some embodiments different analytes may be provides in different systems respectively. The multiple analytes pass through different nanopores in parallel, resulting in decrease in fluorescence in the region proximal to each nanopore which can be separated into multiple fluorescent traces for each nanopore, thereby determining the identity of each analyte.

Such a nanopore array can be used in a multiplex method of identifying multiple analytes, the method comprises:
(a) providing the nanopore array of the invention which comprises multiple analytes, wherein two or more analytes are provided in various systems of the nanopore array;
(b) applying a light capable of exciting the fluorescent reporter molecules contained in each of the first compartments to a region in the multiple first compartment proximal to the nanopores;
(c) measuring multiple fluorescence signals from the fluorescent reporter molecules contained in each of the first compartments to identify the multiple analytes.

The first compartment, the second compartment, the fluorescent reporter molecules, the ionic species, the protein nanopore, the membrane, the bilayer, the hydrophobic medium, the amphipathic molecules, the analyte and other features mentioned here are as described in the context of this description.

In the nanopore array, different systems may comprise the same or different fluorescent reporter molecules and different ionic species. For the convenience of detection, preferably, different systems comprise the same fluorescent reporter molecules and different ionic species.

In the nanopore array, different systems may comprise the same or different nanopores. For the convenience of detection, preferably, different systems comprise the same nanopores.

In some embodiments, the first compartments of different systems are separated from each other and the second compartments of different systems are not separated from each other. In some embodiments, the nanopore array may be provided by bringing multiple first compartments and the second compartment together in a hydrophobic medium comprising amphipathic molecules which is selectively permeable to water molecules, wherein each first compartment comprises at least a protein nanopore in it. A semipermeable membrane consisting of the amphipathic molecules will spontaneously form between each of the first compartments and the second compartment, and the protein nanopore may spontaneously insert into the semipermeable membrane. In some embodiments, each first compartment comprises a protein nanopore, a fluorescent reported molecule and optionally an analyte in it, wherein different analytes could be physically separated into various water in oil compartments.

In some embodiments, the first compartment of each system is provided by aqueous droplet, the second compartment of each system is provided by a hydrogel layer, such as a hydrogel layer comprising agarose substrate. In some embodiments, the second compartments of the multiple systems may be provided by a single hydrogel layer. In some embodiments, the nanopore array may be provided by bringing multiple aqueous droplets and a hydrogel layer together in a hydrophobic medium comprising amphipathic molecules which is selectively permeable to water molecules, wherein each aqueous droplet comprises a protein nanopore, a fluorescent reported molecule and an analyte, wherein different analytes could be physically separated into various water in oil droplets. A semipermeable membrane consisting of the amphipathic molecules will spontaneously form between each of the aqueous droplets and the hydrogel layer, and the protein nanopore may spontaneously insert into the semipermeable membrane.

According to another aspect of the present invention, a method of manufacturing a nanopore array is provided, comprising:
providing multiple aqueous droplets, wherein each of the aqueous droplets comprises a protein nanopore, an analyte and a fluorescent reporter molecule capable of emitting fluorescence when bound to an ionic species;
providing a hydrogel layer, wherein the hydrogel layer comprises the ionic species;
bringing the multiple aqueous droplets and the hydrogel layer together in a hydrophobic medium containing amphipathic molecules such that a semipermeable membrane is formed between each of the aqueous droplets and the hydrogel layer.

The volumn of each aqueous droplet may be less than 100 pL, less than 90 pL, less than 80 pL, less than 70 pL, less than 60 pL, less than 50 pL, less than 40 pL, for example, about 30 pL. The density of a droplet-hydrogel array may be at least 10 droplets per $mm^2$, at least 50 droplets per $mm^2$, at least 100 droplets per $mm^2$, at least 200 droplets per $mm^2$, at least 300 droplets per $mm^2$, at least 400 droplets per $mm^2$, at least 500 droplets per $mm^2$, at least 600 droplets per $mm^2$, at least 700 droplets per $mm^2$, at least 800 droplets per $mm^2$, at least 900 droplets per $mm^2$, at least 1000 droplets per $mm^2$, such as a highly ordered droplet-hydrogel array that could be formed with the assistance from microfluidics.

In one nanopore array of the present invention, the number of the aqueous droplets may be 4-1,000,000. In some embodiments, the number of the aqueous droplets is greater than 10, greater than 100, or greater than 1000. In some embodiments, the number of the aqueous droplets is less than 100,000, less than 10,000, or greater than 1000.

The light source, the light sensor, and the recording device described for the above single system or method can be used in the nanopore array of the invention. As known by those skilled in the art, up to, and over, 2500 pores may be recorded simultaneously with an Electron Multiplying CCD camera (ixon3, Andor).

The amplification of fluorescence signal by the osmolarity/osmolality difference is also applicable to the cases of multiplex system and multiplex method of the invention.

According to another aspect of the present invention, a kit for forming a nanopore array is provided, the kit containing:
filling hydrogel comprising agarose, a buffering agent and an ionic species which is able to specifically bind to a fluorescence reporter molecule to cause it emit fluorescence;
aqueous solution comprising a chelating agent, said fluorescent reporter molecule capable of emitting fluorescence when bound to the ionic species, and a buffering agent; wherein the chelating agent is able to bind to said ionic species;
hydrophobic medium containing amphipathic molecules;
a solid support.

Figure 3:
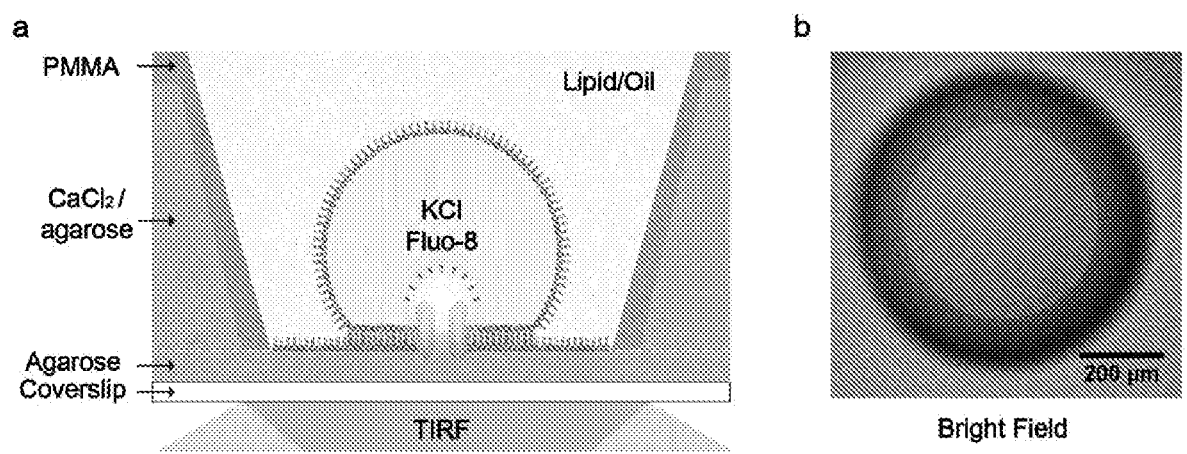
FIG. 3 shows the schematic diagram of the setup. a, A cross-sectional view of an electrode-free oSCR setup. When immersed in the lipid/oil environment (2.5 mg/ml DPHPC in the mixture of hexadecane/silicone oil with a 1:1 volume ratio), the aqueous droplet and the agarose substrate spontaneously forms a droplet interface bilayer (DIB) when brought together[21]. The aqueous droplet is composed of 1 M-2.5 M KCl, 400 μM EDTA, 40 μM Fluo-8, 10 mM HEPES, pH 7.0 with biological nanopores. The agarose substrate is composed of 0.5-1.5 M $CaCl_2$, 10 mM HEPES, pH 7.0 with 2.5% (v/w) low melt agarose. Biological nanopores, which were previously dissolved in the droplet, spontaneously insert into the DIB and permits thermodynamic diffusion of $Ca^{2+}$ into the droplet. The transported $Ca^{2+}$, which immediately bind with Fluo-8 in the droplet, results in fluorescence emission around the pore vicinity when imaged by total internal reflection fluorescence (TIRF) microscopy. b, A bright-field image of a DIB. The boundary of the DIB is visually resolvable from the bright-field image.

The solid support may have any structure suitable for bringing the hydrogel and the droplets of aqueous solution together in the hydrophobic medium containing the amphipathic molecules and thereby forming a semipermeable membrane consisting of the amphipathic molecules between the hydrogel and the droplets of aqueous solution. The solid support may be made of PMMA or glass. The solid support may be a PMMA measurement device that have a structure as shown in FIG. 19. As shown by FIG. 3 and FIG. 19, the PMMA measurement device may has four independent droplet wells in the central recessed area, a gel inlet for filling the filling hydrogel, a outlet for exhausting and a coverslip for supporting the hydrogel. The coverslip may be a oxygen plasma-treated coverslip. PMMA is known as poly methyl methacrylatemethacrylic acid.

The kit may also contain a coating hydrogel, which comprises agarose in water. To form the nanopore array, the coverslip may be spin-coated with molten coating hydrogel and stuck to the PMMA measurement device by filling with molten filling hydrogel through the gel inlet. Then the coverslip may be immersed in the hydrophobic medium containing the amphipathic molecules. Aqueous droplets with protein nanopores and analytes may be pipetted into the hydrophobic medium for incubation. The droplet and the agarose hydrogel may be brought together in the hydrophobic medium, a nanopor array in the form of DIB could spontaneously form.

In some embodiments, the osmolarity of the filling hydrogel is higher than the osmolarity of the aqueous solution or the osmolality of the filling hydrogel is higher than the osmolality of the aqueous solution; or the osmolarity of the filling hydrogel is equal to the osmolarity of the aqueous solution or the osmolality of the filling hydrogel is equal to the osmolality of the aqueous solution; or the osmolarity of the filling hydrogel is lower than the osmolarity of the aqueous solution or the osmolality of the filling hydrogel is lower than the osmolality of the aqueous solution.

In some embodiments, the fluorescent reporter molecule may be fluo-8 and the ionic species may be $Ca^{2+}$.

The filling hydrogel or the aqueous solution may also comprise a protein nanopore.

The aqueous solution may also comprise a salt such as KCl or NaCl.

The fluorescent reporter molecules, the ionic species, the protein nanopore, the hydrophobic medium, the amphipathic molecules, the chelating agent, the analyte and other features mentioned here are as described in the context of this description.

In some embodiments, the coating hydrogel may comprise 0.75% (w/v) agarose in water.

In some embodiments, the filling hydrogel may comprise 2.5% agarose, 1.5 M $CaCl_2$, and 10 mM HEPES, pH 7.0.

In some embodiments, the aqueous solution may comprise 1.5 M KCl, 400 µM EDTA, 40 µM Fluo-8, 10 mM HEPES, pH 7.0.

In some embodiments, the hydrophobic medium containing amphipathic molecules may be a Lipid oil which comprises 5 mg dried film of DPHPC lipids dissolved in a 2 mL mixture of hexadecane and silicone oil with a 1:1 volume ratio. In another aspect, the present invention provides a nanopore array formed by the above manufacture method.

In another aspect, the present invention provides use of the above system or the above nanopore array for optical analyte analysis.

Unless otherwise indicated, most of the features of the system and the method are common across different system and different method, such as the characteristics of the first and the second compartment, the first and the second aqueous solution, the membrane, the nanopore, the fluorescent reporter molecule, and/or the ionic species, and how they are formed, how to use them, etc. For example, the characteristics of the first and the second compartment, the first and the second aqueous solution, the membrane, the nanopore, the fluorescent reporter molecule, and/or the ionic species, and how they are formed, how to use them, etc. in the nanopore array may be as described in the single system above, unless otherwise indicated or impossible.

In the present invention, when referring to components in a solution, "in the first aqueous solution" and "in the first compartment" may be interchangeably used and "in the second aqueous solution" and "in the second compartment" may be interchangeably used.

The embodiments described herein can be understood more readily by reference to the following detailed description, examples, and claims, and their previous and following description. It is to be understood that the embodiments described herein are not limited to the specific uses, methods, and/or products. It is also to be understood that the terminology used herein is for the purpose of describing particular aspects only and is not intended to be limiting.

Further, the following description is provided as an enabling teaching of the various embodiments in their best, currently known aspect. Those skilled in the relevant art will recognize that many changes can be made to the aspects described, while still obtaining the beneficial results of this disclosure. It will also be apparent that some of the desired benefits of the present invention can be obtained by selecting some of the features of the various embodiments without utilizing other features. Accordingly, those who work in the art will recognize that many modifications and adaptations to the various embodiments described herein are possible and can even be desirable in certain circumstances and are a part of the present disclosure. Thus, the following description is provided as illustrative of the principles of the embodiments described herein and not in limitation thereof.

Throughout this application, the term "about" is used to indicate that a value includes the standard deviation of error for the system or method being employed to determine the value. In any embodiment discussed in the context of a numerical value used in conjunction with the term "about," it is specifically contemplated that the term "about" can be omitted.

It should be understood throughout the present specification that expression of a singular form includes the concept of their plurality unless otherwise mentioned. Accordingly, for example, it should be understood that a singular article (for example, "a", "an", "the" in English) comprises the concepts of plural form unless otherwise mentioned.

It should be also understood that the terms as used herein have definitions typically used in the art unless otherwise mentioned. Thus, unless otherwise defined, all scientific and technical terms have the same meanings as those generally used by those skilled in the art to which the present invention pertains. If there is contradiction, the present specification (including the definition) precedes.

All patents and publications, including all sequences disclosed within such patents and publications, referred to herein are expressly incorporated by reference.

EXAMPLES

Example 1

Single Molecule Sensing of Trimethyl-β-Cyclodextrin by DOP: A Proof of Concept Demonstration According to FIG. 1d, the basic configuration of DOP recording includes asymmetric electrolyte buffers separated by a semi-permeable membrane with inserted nanopores. The compartment which is filled with KCl, Fluo-8 and EDTA is defined to be the cis side. Whereas, the compartment which is filled with $CaCl_2$, is defined to be the trans side. A biological nanopore, which forms the only conducting path between cis and trans, promotes binding of $Ca^{2+}$ and Fluo-8 via thermodynamic diffusion through channel transport, which is driven by the chemical gradient. FluoCa, which is the bound form of $Ca^{2+}$ and Fluo-8, emits fluorescence around each nanopore to report the opening state of the sensor.

Figure 2:
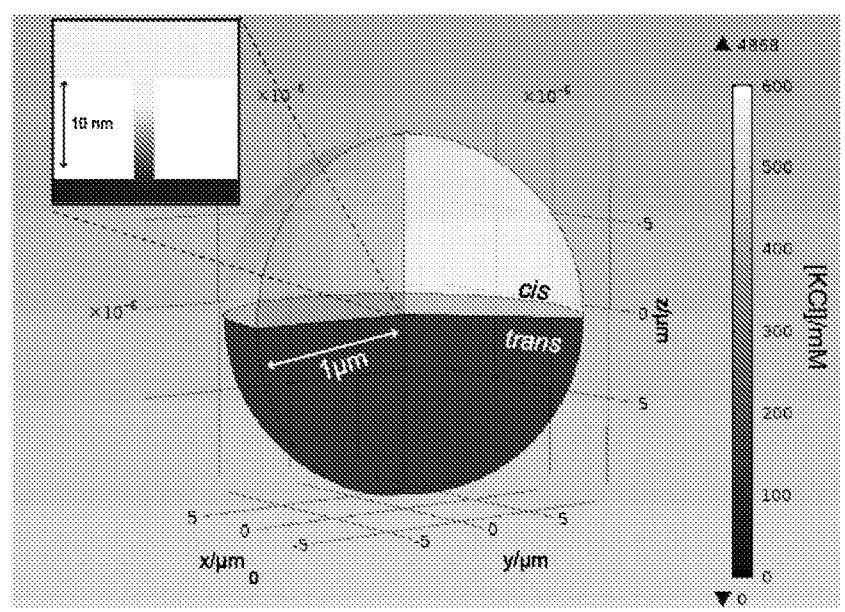
FIG. 2 shows FEM model geometry. A sphere of 10 μm radius filled with electrolyte solution is separated into two chambers (cis: top, trans: bottom) by a 10 nm-thick semipermeable membrane. Only the passages of liquid instead of ions are permitted across the membrane. In the center of the membrane, a single nano-scaled, cylindrical shaped aperture with varying diameter (2 nm-8 nm) is placed, which acts as the only passage for liquid and ion transport between the two chambers. The boundary condition on the cis side was set with varying KCl concentrations (1 M to 2.5 M), whereas the boundary condition on the trans side was set with varying $CaCl_2$ concentration (0.5 M to 1.5 M). All FEM simulations in this paper were performed using this geometry.

Theoretically, a finite element method (FEM) simulation was established, which was adapted from the Poisson-Nernst-Planck-Stokes (PNPS) model[26] (Methods, FIG. 2). To mimic experimental operations, simulation parameters such as different combinations of reagent concentrations could be adjusted by setting different boundary conditions. Tentatively, the simulation was performed by setting the boundary condition in cis as 1.5 M KCl, 40 µM Fluo-8, 400 µM EDTA, the boundary condition in trans as 0.75 M $CaCl_2$, along with a cylindrical channel geometry of 2 nm in diameter. From the result, a concentration gradient of FluoCa was established right above the nanopore (FIG. 1e). Resulted from simultaneous emission from FluoCa, a strong fluorescence intensity contrast are expected on top of the nanopore. The intensity profile, which is generated as a mimic of TIRF imaging (Methods), follows a Gaussian distribution with a full width at half maximum (FWHM) of 2.670 µm (FIG. 1f top).

Experimentally, a droplet interface bilayer (DIB) was established between an aqueous droplet and a 100 nm thick hydrogel sheet (FIG. 3). The aqueous droplet was composed of 1.5 M KCl, 400 µM EDTA, 40 µM Fluo-8, 10 mM HEPES, pH 7.0. The hydrogel sheet was composed of 0.75 M $CaCl_2$, 10 mM HEPES, pH 7.0 with 2.5% (v/w) low melt agarose. WT α-HL (α-HL), which was placed in the aqueous droplet, spontaneously inserts into the DIB and appeared as a bright fluorescence spot during TIRF imaging (Figure if bottom). The fluorescence intensity profile of a representative frame from TIRF imaging follows an approximate Gaussian distribution with a FWHM of 2.583 µm (Figure if bottom), resembles that from the simulation.

Figure 4:
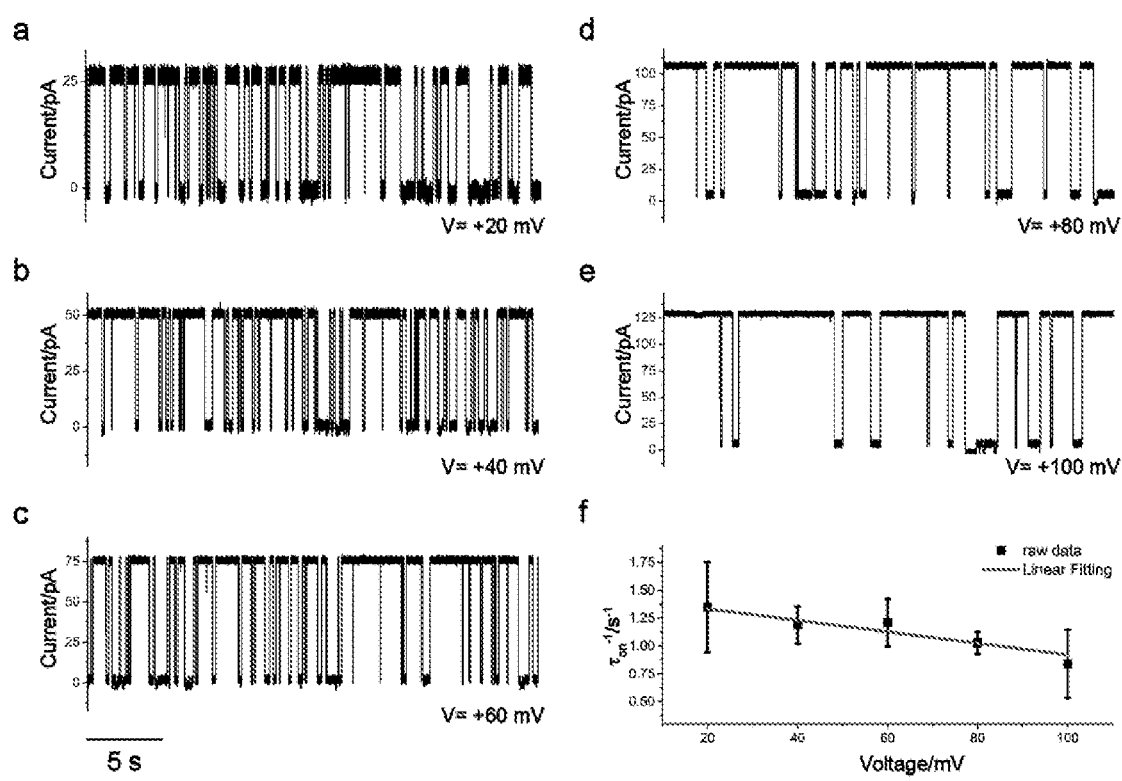
FIG. 4 shows cyclodextrin binding kinetics. a-e, Representative current traces with an +20, +40, +60, +80 and +100 mV applied potential, respectively. Trimethyl-β-cyclodextrin (TriM-β-CD) was added in cis, with a final concentration of 4 mM. The event detection frequency systematically decreases when the applied potential increases. This indicates that an opposing electroosmotic flow in the nanopore may exist which has reduced the probability of TriM-β-CD binding with the pore. f, Plots of $1/\tau_{on}$ as a function of the applied voltages. The statistics of $1/\tau_{on}$ was based on three independent sets of electrophysiology recording (N=3) with 90 s duration for each condition. The electrophysiology recording was performed with 1.5 M KCl, 10 mM HEPES, pH 7.0 in both sides of the membrane. WT α-HL nanopores were added in cis.

Trimethyl-β-cyclodextrin (TriM-β-CD), which interacts with the restriction of a WT α-HL nanopore, generates long residing and deep pore blockade events during electrophysiology recordings[27-29]. Such ease of observation enables TriM-β-CD as a representative small molecule analyte for a proof of concept demonstration of single molecule sensing using DOP. To maintain a stable analyte concentration during DOP recording, TriM-β-CD was added in cis with a 75 mM final concentration. TriM-β-CD binding from cis was also verified by corresponding electrophysiology measurements (FIG. 4). During DOP recording, stochastic binding of TriM-β-CD with α-HL, which results in a restricted $Ca^{2+}$ flux through the channel, generates a highly distinguishable image contrast between the open (Fo) and the blocked state (Fb) of an α-HL nanopore (FIG. 1g). Successive pore-blockades were observed from the corresponding fluorescence traces (FIG. 1g), which were extracted from continuously recorded image series (Methods, FIG. 5). To perform quantitative comparisons between different trials, all fluorescence traces were calibrated and normalized before the analysis (FIG. 6).

From a normalized fluorescence trace, single molecule sensing events were characterized by the event dwell time ($t_{off}$), the inter-event duration ($t_{on}$) and the percentage blockade depth (% $F_b$). The histogram of $t_{off}$ and $t_{on}$ displays an exponential distribution, which could be fit and characterized by their mean time constant $\tau_{off}$ and $\tau_{on}$, respectively (FIG. 7). By varying the TriM-β-CD concentration in cis, the reciprocal of dwell time ($1/\tau_{off}$) remains constant, whereas the reciprocal of inter-event interval ($1/\tau_{on}$) correlates linearly with the TriM-β-CD concentration in cis (FIG. 1h, Table 1).

TABLE 1

$1/\tau_{on}$ and $1/\tau_{off}$ of TriM-β-CD with different [TriM-β-CD].

| Concentration (µM) | $1/\tau_{on}$ ($s^{-1}$) | $1/\tau_{off}$ ($s^{-1}$) |
|---|---|---|
| 15 | 0.027 ± 0.007 | 2.515 ± 0.440 |
| 45 | 0.047 ± 0.011 | 2.437 ± 0.449 |
| 75 | 0.086 ± 0.023 | 2.953 ± 0.616 |
| 105 | 0.127 ± 0.031 | 3.640 ± 0.330 |

DIB was established with 1.5 M KCl, 400 µM EDTA, 40 µM Fluo-8, 10 mM HEPES, pH 7.0 in cis and 0.75 M $CaCl_2$, 10 mM HEPES, pH 7.0 in trans. TriM-β-CD was added to cis. Three independent measurements were performed to form the statistics.

From DOP recording, a mean $\tau_{off}$ value of 0.347±0.067 s and a mean $F_p$ value of 0.078±0.010 was recorded. Here, $F_p$ is defined to be the mean blockage depth, which was derived from % $F_b$ values from each trial of DOP recording (FIG. 7). Whereas, corresponding electrophysiology results as acquired with a +20 mV potential bias generated a $\tau_{off}$ value of 0.386±0.392 s and an $I_p$ value of 0.065±0.002. Here, $I_p$ is defined to be the mean blockage depth from each trial of electrophysiology recording. Three independent trials were performed for each measurement conditions to form the statistics. This resemblance of results thus confirmed the feasibility of single molecule sensing by DOP (FIG. 1i).

Though not demonstrated, single molecule sensing of other small molecules, such as sugar[30, 31], ions[32], nucleotides[33], neurotransmitters[34], amino acids[35] etc., could be similarly performed by DOP recording in principle with an added advantage from the throughput. Since the analyte capturing is driven by a chemical gradient instead of an electrochemical gradient, the charge of the analyte is not critical for DOP recording. However, the strength of fluorescence emission and the analyte binding efficiency could be further improved to match that of electrophysiology.

Example 2

Enhanced DOP Sensing by Directional Osmosis

During routine electrophysiology recording, the applied electrochemical gradient is critical for driving a sustained flow of charged particles, such as ions and analytes. Intuitively, to drive a directed flow of analtyes into the nanopore sensor without using electrodes, an asymmetry of other forms has to be introduced.

The DIB, which is a self-assembled membrane composed of 1,2-diphytanoyl-sn-glycero-3-phosphocholine (DphPC) lipid, is selectively permeable to water molecules instead of ions[36, 37]. When a difference of osmolarity concentration ($C_{solute}=iM_{solute}$) exists across the DIB, an osmotic pressure is established according to $\Delta \pi=(C_{solute,cis}-C_{solute,trans})RT$, where i is the dimensionless van't Hoff index that addresses the number of dissociated ions from each solute molecule, $M_{solute}$ is the molar concentration of the solute, R is the ideal gas constant, and T is the temperature in kelvins. Here, the positive direction of the osmotic pressure is defined to be from cis to trans (this is a definition for easy understanding, although it may be that the osmotic pressure on cis is higher than trans). This osmotic pressure subsequently drives an oriented flow of water, ions and analytes through a biological nanopore which is inserted in the membrane[22]. As a result, an enhanced translocation efficiency for analyte should be achieved with this introduced asymmetry.

To verify this hypothesis experimentally, a series of DOP recordings were carried out in DIBs (FIG. 3) with varying KCl concentrations in cis (1.0-2.5 M), while the $CaCl_2$ concentration in trans was kept constant (0.75 M). Tentatively, α-HL and TriM-β-CD were selected again as the model sensor and analyte, respectively, where the concentration of TriM-β-CD in cis was fixed at 15 mM in cis. From representative DOP recordings, an enhanced capture rate of TriM-β-CD was observed from time extended fluorescence traces, when the KCl concentration in cis was decreased from 2.5 M to 1.0 M (FIG. 3). By evaluating the $1/\tau_{on}$ values for events from independent measurements, a systematically decrease of $1/\tau_{on}$ was observed in accordance with the decrease of osmotic pressure (FIG. 8, Table 2), which means that a higher rate of event detection was observed with the assistance from a directed osmotic flow.

TABLE 2

$1/\tau_{on}$ of TriM-β-CD with different [KCl] in cis.

| KCl concentration (M) | $1/\tau_{on}$ (s$^{-1}$) |
|---|---|
| 1.0 | 0.056 ± 0.019 |
| 1.5 | 0.028 ± 0.014 |
| 2.0 | 0.023 ± 0.007 |
| 2.5 | 0.022 ± 0.009 |

A DIB was established with 1-2.5 M KCl, 400 µM EDTA, 40 µM Fluo-8, 10 mM HEPES, pH 7.0 in cis and 0.75 M $CaCl_2$, 10 mM HEPES, pH 7.0 in trans. 15 mM TriM-β-CD was added to cis. Three independent measurements were performed to form the statistics.

It was also discovered that a significantly improved fluorescence image contrast was observed from DOP recordings when an osmotic flow from cis to trans exists. This phenomenon could be noticed from the reduced thermal noises in the fluorescence traces with measurement conditions of lower KCl concentrations (FIG. 8a, FIG. 9). Here, the high thermal noises observed from the fluorescence trace is a consequence of reduced photon counts during imaging.

To further investigate why the fluorescence intensity from DOP recording could be modulated by osmosis (FIG. 8c, Table 3), a different set of experiment was carried out with 1-2.5 M KCl, 400 µM EDTA, 40 µM Fluo-8, 10 mM HEPES, pH 7.0 in cis and 0.75 M $CaCl_2$, 10 mM HEPES, pH 7.0 in trans. To avoid interference from analyte binding, TriM-β-CD was omitted. To avoid interference from uneven TIRF illumination or laser power fluctuations when evaluating the brightness of the fluorescence, a Signal to Background Ratio (SBR) value was introduced to quantitatively compare different trials of DOP recordings (Methods). From representative image frames and the corresponding SBR values, the brightness of the fluorescence spot was clearly enhanced when a larger osmotic pressure from cis to trans was introduced. Five independent measurements were included for each condition to form the statistics (FIG. 8c).

TABLE 3

FWHM and SBR with different [KCl]

| KCl concentration (M) | FWHM (µm) | SBR |
|---|---|---|
| 1.0 | 2.863 ± 0.156 | 14.108 ± 3.660 |
| 1.5 | 2.822 ± 0.197 | 12.957 ± 2.809 |
| 2.0 | 2.77 ± 0.200 | 11.228 ± 2.579 |
| 2.5 | 2.65 ± 0.270 | 6.151 ± 2.295 |

A DIB was established with 1-2.5 M KCl, 400 µM EDTA, 40 µM Fluo-8, 10 mM HEPES, pH 7.0 in cis and 0.75 M $CaCl_2$, 10 mM HEPES, pH 7.0 in trans. Five independent measurements were performed to form the statistics.

This phenomenon could also be observed from corresponding FEM simulations, which were carried out by setting the boundary condition in cis as 1-2.5 M KCl, 40 µM Fluo-8, 400 µM EDTA and the boundary condition in trans as 0.75 M $CaCl_2$ (FIG. 8d). By plotting the Fluo-8 distribution within the simulation space, it is clearly noticed that a concentrated Fluo-8 distribution was established near the cis side of the membrane when a directed osmotic flow exist from cis to trans. This is happening due to the fact that Fluo-8, which is impermeable to the lipid membrane, is enriched via the osmotic flow and consequently the fluorescence intensity was enhanced (FIG. 10).

Example 3

Further SBR Optimization with Enlarged $Ca^{2+}$ Flux

However, Fluo-8 enrichment by osmosis should not happen in a solid state nanopore device where the membrane doesn't possess a semi-permeability feature. Alternatively, the SBR from DOP recording could be improved by the introduction of more $Ca^{2+}$ flux through nanopores. An immediate solution following this strategy is to increase the [$CaCl_2$] in trans, which directly raise the chemical gradient of [$Ca^{2+}$] across the membrane. To approve this hypothesis, a series of DOP recordings were carried out by gradually upregulating the $CaCl_2$ concentration in trans. To avoid the interference from osmosis, the KCl concentration in cis was adjusted accordingly so that the osmolarity concentration in cis and trans were kept isotonic all the time.

Experimentally, a DIB was established with 0.75 M, 1.5 M or 2.25 M KCl, 400 µM EDTA, 40 µM Fluo-8, 10 mM HEPES, pH 7.0 in cis and 0.5M, 1 M or 1.5 M $CaCl_2$, 10 mM HEPES, pH 7.0 in trans. Representative image frames show a systematically enlargement of the fluorescence spot size when acquired with a combination of electrolyte buffer where the [$CaCl_2$] in trans was higher (FIG. 11a). Corresponding 2D Gaussian fittings (FIG. 11a), which were color coded according to the fitting amplitude, give a more straight forward comparison of the fluorescence intensity acquired with these conditions. A quantitative measure of the SBR and the FWHM from DOP recordings acquired with these electrolyte combinations was demonstrated in FIG. 11b, from which both the FWHM and the SBR (Table 4) increases when the osmolarity concentration in both sides of the membrane were upregulated. 12 independent measurements were included for each condition to form the statistics.

TABLE 4

FWHM and SBR with different [CaCl$_2$]

| CaCl$_2$ concentration (M) | FWHM (μm) | SBR |
|---|---|---|
| 0.5 | 2.381 ± 0.376 | 6.135 ± 3.150 |
| 1.0 | 3.003 ± 0.319 | 18.482 ± 6.545 |
| 1.5 | 3.888 ± 0.329 | 24.024 ± 8.304 |

DIB was established with KCl (0.75 M, 1.5 M and 2.25 M), 400 μM EDTA, 40 μM Fluo-8, 10 mM HEPES, pH 7.0 in cis and CaCl$_2$ (0.5M, 1 M and 1.5 M), 10 mM HEPES, pH 7.0 in trans. Twelve independent measurements were performed to form the statistics.

PEGs, which is a macromolecule that is electric neutral when dissolved in a buffer of neutral pH, has been demonstrated to translocate through α-HL nanopores during electrophysiology recordings[38]. It was reported that the capture rate was enhanced and the event residing time were extended when measured with an electrolyte buffer of higher salt concentrations[39]. As a demonstration, PEG 1500 was selected as the model analyte for single molecule sensing of macromolecules by DOP.

Experimentally, the DIB was established with 2.25 M KCl, 10 mM HEPES, 400 μM EDTA, 40 μM Fluo-8, 20 mM PEG 1500, 10 mM HEPES, pH 7.0 in cis and 1.5 M CaCl$_2$, 10 mM HEPES, pH 7.0 in trans. With the addition of 20 mM PEG 1500 in cis, an abundance of spiky translocation events immediately appeared from the extracted fluorescence traces (FIG. 11c). The resemblance of these pore translocation features with reported electrophysiology data confirms that PEG1500 could be sensed by DOP recording, similar to that demonstrated with TriM-β-CD.

However, the solubility of the analyte is normally decreased in an electrolyte buffer of high salt concentrations [39] Furthermore, the salt concentration is limited by the the maximum solubility of electrolytes in water as well (CaCl$_2$: 6.767 M, KCl: 3.408 M, at 20° C.). To bring more Ca$^{2+}$ flux without reaching this limit, a nanopore sensor with a larger aperture could be introduced during DOP recording, which is confirmed by corresponding FEM studies (Methods, FIG. 11d). According to reported crystallography results, the restriction of a ClyA nanopore, which measures 3.8 nm in diameter, is 2.7 times the diameter of an α-HL[40]. Acknowledge to its large channel opening, ClyA and its variants were developed to sense large bio-macromolecules such as dsDNA or small proteins[40-44]. ClyA-RR, which was reported to be a charge optimized mutant and could effectively translocate dsDNA during electrophysiology recording[42], was selected for DOP recording (Methods, FIG. 12). Though not demonstrated, phi29 connector protein [45] or solid state nanopores[24, 25], were great candidates as well.

Tentatively, the DIB was established with 1.5 M KCl, 400 μM EDTA, 40 μM Fluo-8, 10 mM HEPES, pH 7.0 in cis and 1.5 M CaCl$_2$, 10 mM HEPES, pH 7.0 in trans. The electrolyte combination of 1.5 M KCl (cis)/1.5 M CaCl$_2$(trans) was chosen by taking into account of osmotic pressure (FIG. 8), CaCl$_2$ concentration (FIG. 11) and pore mobility[22]. To perform a quantitative comparison with nanopores of different channel openings during DOP recording, dodecameric ClyA-RR nanopores and heptameric α-HL nanopores were both placed in the droplet for simultaneous measurements from the same DIB.

When inserted, a ClyA-RR nanopore appears as a huge and dazzling fluorescence spot, whereas an α-HL nanopore appears small in size along with a dim intensity (FIG. 11e).

The FWHM and SBR as derived from DOP recordings with ClyA-RR clearly outperform that from α-HL with the introduction of more Ca$^{2+}$ flux across the membrane (FIG. 11f, Table 5). Five independent measurements were performed to form the statistics.

TABLE 5

FWHM and SBR of αHL and ClyA-RR nanopores

| Type | FWHM (μm) | SBR |
|---|---|---|
| αHL | 2.688 ± 0.600 | 12.24 ± 1.336 |
| ClyA-RR | 5.098 ± 0.316 | 42.893 ± 11.737 |

DIB was established with 1.5 M KCl, 400 μM EDTA, 40 μM Fluo-8, 10 mM HEPES, pH 7.0 in cis and 1.5 M CaCl$_2$, 10 mM HEPES, pH 7.0 in trans. The pores were added to cis. Five independent measurements were performed to form the statistics.

Apart from the improved SBR, the larger aperture of ClyA also contributes to an enhanced osmotic flow as predicted from the FEM simulation as well, which may serve to provide the driving force for DNA translocation (FIG. 11g and FIG. 13). Though significant efforts have been paid to counteract the electrophoretic force during DNA translocation[46], the electrophoretic force, which efficiently untangles coiled DNA during translocation[9], was still considered indispensable during DNA sensing. However, the long persistence length of dsDNA[47] and the wide opening of ClyA nanopore may reduce the entropic barrier for dsDNA translocation[48]. Furthermore, the huge vestibule of ClyA may also serve to accommodate dsDNA in a form of partial translocation to report the sensing signal of dsDNA during the DOP recording as well.

Example 4 dsDNA and ssDNA Translocation Through ClyA Nanopores

Experimentally, the DIB was established with 1.5 M KCl, 10 mM HEPES, 400 μM EDTA, 40 μM Fluo-8, 2 mM dsDNA (78 bp), 10 mM HEPES, pH 7.0 in cis and 1.5 M CaCl$_2$, 10 mM HEPES, pH 7.0 in trans (FIG. 14a). The osmolarity concentration on both sides of the DIB were designed to establish a sustained osmotic pressure from cis to trans. dsDNA, which is composed of 78 bp (Table 6), was optionally dissolved in the aqueous droplet with a final concentration of 2 μM.

TABLE 6

Nucleic acid abbreviations and sequences

| Abbreviations | Sequences(5'-3') |
|---|---|
| 78 nt ssDNA-a | TTGGCATGTCAGAATGTTAGAATGTTAGAAT GTTAGAATGTTAGAAT GTTAGAATGTTTCAGATCTCACTATCAAAAA (SEQ ID NO: 2) |
| 78 nt ssDNA-b | TTTTTGATAGTGAGATCTGAAACATTCTAAC ATTCTAACATTCTAACATTCT AACATTCTAACATTCTGACATGCCAA (SEQ ID NO: 3) |

Note: To form dsDNA, complementary ssDNAs (78 nt ssDNA-a and b) were dissolved in 1.5 M KCl buffer (1.5 M KCl, 10 mM HEPES, pH 7.0), heated up to 95° C. and gradually cooled down (−5° C./min) to room temperature (25° C.) on a PCR thermal cycler (ABI 2720).

Without any dsDNA added in the droplet, the representative fluorescence trace from a ClyA nanopore appears stably open with no spontaneous gating activities (FIG. 14b). When dsDNA was added in the droplet, successive fluorescence blockades spontaneously appear during DOP recording (FIG. 14c). The observed blockades from DOP recording, showed a mean F, of 0.625±0.014, and a mean $\tau_{off}$ of 2.538±0.849 s (N=3). These results suggest that dsDNA interaction with ClyA-RR was happening without an applied electrochemical gradient. The long residing time may result from the omitted electrophoretic force during the measurements or may due to that the dsDNA was trapped within the huge vestibule structure of ClyA.

To further verify this phenomenon via routine electrophysiology recordings, a planar lipid membrane was established with 1.5 M KCl 10 mM HEPES, pH=7.0 in cis and 1.5 M $CaCl_2$, 10 mM HEPES, pH=7.0 in trans. 78 bp dsDNA were added in cis with a 2 µM final concentration. Extremely low voltages were applied as a mimic of DOP recording, where the transmembrane electric potential were strictly zero. FIG. 14d shows representative electrophysiology traces which were recorded with a +6 mV, +4 mV or +2 mV transmembrane potential, respectively. Similar translocation events as observed from DOP recordings were monitored, which verified our hypothesis that dsDNA could interact with ClyA and generate detectable sensing signals when optically monitored without electrodes. The $l_p$ value, which was 0.611±0.357 at +6 mV, 0.605±0.460 at +4 mV and 0.786±0.224 at +2 mV, was also qualitatively consistent with the blockades observed from DOP recordings (FIG. 15, Table 7). The dwell time was widely distributed from 1 to $10^5$ ms during electrophysiology recordings, whereas due to the limited acquisition bandwidth from DOP recording, fast events below 30 ms can't be detected optically (FIG. 14d).

TABLE 7

| Blockade level of dsDNA translocation. | | |
|---|---|---|
| Individual experiments | $F_P$ | FWHM |
| 1 | 0.628 | 0.114 |
| 2 | 0.638 | 0.057 |
| 3 | 0.610 | 0.138 |

DIB was established with 1.5 M KCl, 400 µM EDTA, 40 µM Fluo-8, 10 mM HEPES, pH 7.0 in cis and 1.5 M $CaCl_2$, 10 mM HEPES, pH 7.0 in trans. 2 µM dsDNA was added to cis. Three independent measurements were performed to form the statistics.

To further verify ssDNA translocation through nanopores, electrode-free 20-nt ssDNA sensing using α-HL nanopores is performed. The results are shown in FIG. 17. A αHL WT nanopore that only allows ssDNA to pass through but not dsDNA is used. Since this nanopore is relatively small, a high concentration of 50 µmol/L ssDNA is used. The percentage blockade depth shows that the 20-nt ssDNA is able to pass through the α-HL nanopore.

Another electrode-free 78-nt ssDNA sensing using ClyA-RR is performed and the results are shown in FIG. 18. ClyA-RR has a larger aperture and allow both ssDNA and dsDNA to pass through. For ssDNA, the characteristics of fluorescenc emission is significantly affected by the sequence and the secondary structure the of the ssDNA because the ssDNA may not be completely straight when passing through the nanopore. The 78-nt ssDNA-a and the poly $A_{78}$ exhibited very different fluorescenc emission characteristics. The poly $A_{78}$ has uniform and shallow percentage blockade depths. The 78-nt ssDNA-a has different percentage blockade depths and long event dwell time. It is evidenced that ssDNA can be sensed by DOP.

Example 5

Multiplex DOP Recording with a Fingertip Sized Device and Future Prospects

By omitting the need of electrode arrangement, DOP enables a much more compact device size while the advantages of low cost (<1 $) and high throughput is still retained. This configuration is suitable for fabricating disposable nanopore chips for clinical diagnosis, where cross contamination should be strictly prohibited. As a proof of concept, a miniaturized device (10 mm by 10 mm by 1 mm) was manufactured from bulk poly methyl methacrylatemethacrylic acid (PMMA) (FIG. 16a, FIG. 2). DOP recording could be carried out by placing the chip directly above a TIRF objective, which is used both for illumination and imaging. As a demonstration, DOP recording from α-HL and ClyA was carried out with this miniaturized device, where α-HL and ClyA could both be visually monitored (FIG. 16c).

However, DOP measurements from a single DIB were restricted with one combination of pore and analytes. By omitting the need from electrode accommodation, DOP enables multiplex recording from different DIBs with an extremely simple configuration and a much reduced measurement volume, where different analytes could be physically separated into various water in oil compartments.

As a proof of concept, micro-droplets (~30 pL) containing ClyA-RR nanopores were generated and pipetted into the measurement reservoir filled with lipid oil solution (FIG. 16d). Though not mono-dispersed in size, many independent DIBs could spontaneously form for subsequent DOP recording with extreme ease (FIG. 16e). In a DIB that was around 40 µm in diameter, a single inserted ClyA nanopore was unambiguously observed as a bright fluorescence spot (FIG. 16f), which lasts for ~10 minutes before the EDTA in the droplet was depleted from $Ca^{2+}$ binding. This corresponds to an effective measurement density of $10^3$ independent DIBs per $mm^2$, such as in a highly ordered DIB array that could be formed with the assistance from microfluidics setups[49]. However, this high measurement density could not be easily achieved by oSCR or electrophysiology due to the complexities from the electronics integration.

Though advantageous of being electrode-free, DiffusiOptoPhysiology is not without limitations. As a fluorescence imaging technique, the temporal resolution of DOP is generally limited to ~10 ms per frame when recorded in the full field of view (135 µm by 135 µm).

Fluorescence readout from a reduced amount of image pixels could immediately boost the speed of acquisition. With the improved addressability from a highly ordered array of nanopores, high speed DOP recording could be potentially carried out by spinning disk confocal imaging [50]. In the absence of an electric field, the limit of detection (LOD) during DOP was generally higher (~µM) than that (down to ~nM) from electrophysiology or oSCR.

However, with the omission of electrodes accomodation, it was compensated that a much smaller volume of measurement (down to ~30 pL) was needed, where the absolute cost of sample is actually reduced.

Conclusions

In summary, we have demonstrated how DiffusiOptoPhysiolgy, which was inspired from natural passive channel transport, could be used as a nanopore sensing platform. Though the fluorescence emission during DOP recording was triggered by passive diffusion and subsequent binding of $Ca^{2+}$ and Fluo-8, the fluorescence intensity is strong enough to serve a wide variety of single molecule sensing applications as demonstrated. Upon combined optimizations from electrolytes and channel sizes, this technique enables high-throughput nanopore measurements while the sensing performance remains comparable with conventional electrophysiology recording or oSCR. Though demonstrated with total internal reflection fluorescence (TIRF) microscopy, DOP is in principle flexible with any fluorescence platforms such as confocal or epi-fluorescence microscopy. Without the need of space to accommodate electrodes, the measurement volume of DOP was further reduced to ~30 pL, which is the lowest record ever been reported and may be suitable for measurements of analytes with an extremely low abundance. DOP recording with an array of micro-droplets also enables multiplex measurements from independent compartments, which were simply established from water in oil separations. Though possessing integrated nanotechnology sensors as a chip, the omission of electronics has significantly reduced the cost and the size of the device. This scheme may thus inspire future clinical applications using disposable nanopore chips in a wide variety of applications.

Methods

Materials

Hexadecane, silicone oil AR20, pentane, ethylenediaminetetraacetic acid (EDTA), Triton X-100, Genapol X-80 and PEG1500 were from Sigma-Aldrich. Potassium chloride, calcium chloride, magnesium chloride and sodium chloride were from Aladdin. Dioxane-free isopropyl-β-D-thiogalactopyranoside (IPTG), Dodecyl β-D-maltopyranoside (DDM), kanamycin sulfate, trimethylamine methane (Tris) and imidazole were from Solarbio. Low melting point agarose and wide-range DNA ladder (20-500 bp) were from Takara. Precision plus protein marker and 4-15% polyacrylamide gels were from Bio-Rad. Ethanol and acetone were from Sinopharm. Fluo-8H sodium salt (Fluo-8) was from AAT Bioquest. 1,2-diphytanoyl-sn-glycero-3-phosphocholine (DPhPC) was from Avanti Polar Lipids. 4-(2-Hydroxyethyl)-1-piperazineethanesulfonic acid (HEPES) was from Shanghai Yuanye Bio-Technology. E. coli strain BL21 (DE3) was from BioMed. Trimethyl-β-cyclodextrin was from Tokyo chemical industry (Shanghai). LB broth and LB agar were from Hopebio. All the items listed above were used as received.

KCl buffer (1-2.5 M KCl, 10 mM HEPES, pH 7.0) and $CaCl_2$ buffer (0.5-1.5 M $CaCl_2$, 10 mM HEPES, pH 7.0) were membrane filtered (0.2 μm cellulose acetate, Nalgene). For simplicity, 1-2.5 M KCl buffer stands for 1-2.5 M KCl, 10 mM HEPES, pH 7.0. 0.5-1.5 M $CaCl_2$ buffer stands for 0.5-1.5 M $CaCl_2$, 10 mM HEPES, pH 7.0, if not otherwise state. The KCl buffer was treated with Chelex 100 resin (Bio-Rad) overnight before use to get rid of contaminating divalent ions.

High-performance liquid chromatography (HPLC)-purified DNA (Table 6) was dissolved in DNase/RNase-free water prior to use. To form dsDNA, complementary ssDNAs were further dissolved in 1.5 M KCl buffer (1.5 M KCl, 10 mM HEPES, pH 7.0), heated up to 95° C. and gradually cooled down (−5° C./min) to room temperature (25° C.) on a PCR thermal cycler (ABI 2720).

The protein nanopores used in this paper were α-HL WT and ClyA-RR (FIG. 7), which were expressed in E. coli and purified based on published protocols[22, 42].

ClyA-RR Preparation

The gene coding for monomeric ClyA-RR (D64R/C87A/L99Q/E103G/S110R/F166Y/I203V/C285S/K294R/H307Y) protein was custom synthesized and constructed in a pET 30a(+) plasmid (Genescript, New Jersey). A hexahistidine tag was introduced at the c-terminus of the protein for later chromatography purifications. The plasmid was transformed into E. coli BL21 (DE3) competent cells and cultured in the LB agar plate with 50 μg/mL kanamycin for 18 hours. A single colony was inoculated into the LB medium containing 50 μg/mL kanamycin and incubated at 37° C. till $OD_{600}$ reaches 4.0. Protein expression was inducted by adding isopropyl β-D-thiogalactoside (IPTG) to the LB medium reaching a final concentration of 1 mM. The culture medium was further shaken (200 rpm) for 16 hours at 15° C. The cells were then harvested by centrifugation (4000 rpm, 4° C., 20 min). The pellets were collected and re-suspended in the lysate buffer (150 mM NaCl, 50 mM Tris-HCl, 10% Glycerol, pH 8.0), lysed by sonication (15 min) and centrifuged (14,000 rpm, 4° C., 40 min) to remove intact cells. After syringe filtration, the supernatant was loaded onto a nickel affinity column (HisTrap™ HP, GE Healthcare). After washing the column with wash buffer A (150 mM NaCl, 50 mM Tris-HCl, 10% Glycerol, 20 mM imidazole, pH 8.0), the target protein was eluted in sequence using three wash buffers (buffer B: 500 mM NaCl, 15 mM Tris-HCl, 10% Glycerol, 300 mM imidazole, pH 8.0; buffer C: 500 mM NaCl, 15 mM Tris-HCl, 10% Glycerol, 50 mM imidazole, pH 8.0; buffer D: 500 mM NaCl, 15 mM Tris-HCl, 10% Glycerol, 20 mM imidazole, pH 8.0). The elution fraction which contains ClyA-RR monomers were determined using SDS-PAGE gel electrophoresis (FIG. 12) and stored in the buffer of 270 mM NaCl, 50 mM Tris-HCl, 10% Glycerol, 0.2% Triton 100, pH 8.0 at −80° C.

According to previous studies[42], 0.25% (w/v) β-dodecylmaltoside (DDM) was added to promote the pore oligomerization. After incubation at 25° C. for 15 min, the result of pore oligomerization were characterized by blue native polyacrylamide gel electrophoresis (BN-PAGE, Bio-Rad) using 4-15% polyacrylamide gels (FIG. 12). The gel showed that the monomers had been self-assembled into oligomers before the addition of DDM. However, to strictly follow previous studies[42], ClyA-RR dodecamers with DDM addition were still used for follow up measurements. Here, the bands which corresponds to dodecameric ClyA-RR was cut from the gel and soaked in 150 mM NaCl, 15 mM Tris-HCl, pH 7.5 supplemented with 0.2% DDM and 10 mM EDTA for 3 hours. The supernatant, which contains dodecameric proteins diffused out of the gel, were collected by centrifugation (20,000 g, 4° C., 20 min). The collected dodecameric ClyA-RR proteins were either immediately used for subsequent experiments or stored at 4° C. for up to 14 days.

DIB Formation

A detailed description about how a droplet/hydrogel bilayer was created was previously reported[10]. Briefly, oxygen plasma-treated coverslips (24 mm×40 mm) were spin-coated (3000 rpm, 30 s) with 200 μL molten agarose (0.75% w/v, in Mili Q water). The coverslip was stuck to a PMMA device by filling the microfluidic channels within the device with molten agarose (2.5% w/v, in $CaCl_2$ buffer)[10]. The lipid/oil solution was prepared by dissolving 5 mg dried film of DPHPC lipids in a 2 mL mixture of hexadecane and silicone oil with a 1:1 volume ratio. A lipid monolayer was formed on the agarose-coated glass coverslip when immersed in the lipid-oil solution. In preparation of aqueous droplets, protein nanopores and other analyte could be added into the aqueous buffer, which is composed of 1 M-2.5 M KCl, 400 μM EDTA, 40 μM Fluo-8, 10 mM HEPES, pH 7.0. Aqueous droplets of various volumes were pipetted into the lipid/oil solution for incubation. After 5 min, a self-assembled lipid monolayer at the water-oil interface could form. When this droplet and the agarose substrate were brought together in the lipid/oil solution, a stable bilayer (DIB) could spontaneously form.

TIRF Imaging and Optical Recordings

The DIB was imaged using an inverted microscope (Eclipse Ti-U, Nikon) equipped with a 60× oil immersion TIRF objective (NA=1.49, Plan Apo, Nikon). The fluorescence was excited with a 473 nm Diode Pumped Solid State (DPSS) laser (100 mW, Changchun New Industries Optoelectronics Technology). The image was acquired with an electron-multiplying CCD camera (iXon3 897, Andor). The exposure time was set to 3-30 ms. The maximum field of view was 135 μm by 135 μm.

Electrical Recordings

Electrophysiology recordings were performed as previously reported[8]. The electrophysiology trace was acquired with 25 kHz sampling rate, low-pass filtered at 1 kHz (Axopatch 200B, Molecular Devices), digitized and recorded using the Digidata 1550A digitizer (Molecular Devices). The subsequent data analysis was performed with Clampfit 10.7 (Molecular Devices).

The Finite Element Modelling (FEM) Simulation $Ca_{2+}$ binding with the calcium indicator dye Fluo-8 results in fluorescence emission near the pore vicinity. The excessive $Ca^{2+}$, which binds with EDTA, results in reduced fluorescence background. These two completive reactions could be described as in equation (1, 2), where α and β stands for the forward and backward binding rate, respectively.

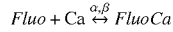

(1)

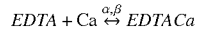

(2)

Optical single channel recording (oSCR) could be simulated with FEM using the Poisson-Nernst-Planck-Stokes (PNPS) model[24, 26], where the Nernst-Planck-Stokes equation is described in equation (3).

$$D_i \nabla^2 [c_i] + \frac{D_i z_i F}{k_b T} \nabla \cdot ([c_i] \nabla V) + R_i - u \cdot \nabla [c_i] = 0 \quad (3)$$

In the scenario of electrode-free oSCR, the electrical potential V is set to be constant within the simulation space. Equation (3) is thus further simplified (equation (4)), where the motion of ions are only driven by passive diffusion, chemical reactions and fluidic flows.

$$D_i \nabla^2 [c_i] + R_i - u \cdot \nabla [c_i] = 0 \quad (4)$$

Here, $[c_i]$ starnds for the concentration of different ionic species. $R_i$ stands for chemical reaction terms, u stands for the fluid velocity. Free $Ca^{2+}$ could bind with either Fluo-8 or EDTA as described in equation (1, 2).

For different ions, equation (4) is further expanded, where the identity of ions are annotated by the corresponding footnote as described in equation (5-10). Here, FluoCa and EDTACa stands for the bound form of Fluo-8 and EDTA with $Ca^{2+}$, respectively.

$$D_{Fluo} \nabla^2 [Fluo] + \beta_F [FluoCa] - \alpha_F [Fluo][Ca^{2+}] - u \cdot \nabla [Fluo] = 0 \quad (5)$$

$$D_{FluoCa} \nabla^2 [FluoCa] - \beta_F [FluoCa] + \alpha_F [Fluo][Ca^{2+}] - u \cdot \nabla [FluoCa] = 0 \quad (6)$$

$$D_{EDTA} \nabla^2 [EDTA] + \beta_E [EDTA] - \alpha_E [EDTA][Ca^{2+}] - u \cdot \nabla [EDTA] = 0 \quad (7)$$

$$D_{EDTACa} \nabla^2 [EDTACa] - \beta_E [EDTACa] + \alpha_E [Ca^{2+}] - u \cdot \nabla [EDTA] = 0 \quad (8)$$

$$D_K \nabla^2 [K^+] + \frac{D_K z_K F}{k_b T} \nabla \cdot ([K^+] \nabla V) - u \cdot \nabla [K^+] = 0 \quad (9)$$

$$D_{Cl} \nabla^2 [Cl^-] + \frac{D_{Cl} z_{Cl} F}{k_b T} \nabla \cdot ([Cl^-] \nabla V) - u \cdot \nabla [Cl^-] = 0 \quad (10)$$

The electrostatic potential in a standard PNPS model is governed by Poisson's equation, which is described in equation (11):

$$\nabla^2 V = -\frac{F}{\varepsilon}(z_{Ca}[Ca^{2+}] + z_k [K^+] + z_{Cl}[Cl^-]) \quad (11)$$

However, during electrode-free oSCR, the electrical potential V is constant within the simulation space, the equation is thus simplified as equation (12):

$$z_{Ca}[Ca^{2+}] + z_k [K^+] + z_{Cl}[Cl^-] = 0 \quad (12)$$

The simulation parameters are primarily taken from literatures[26]. Here D is the diffusion constant ($D_{Fluo}=D_{FluoCa}=15$ μm$^2$ s$^{-1}$, $D_k=D_{cl}=D_{Ca}=D_{EDTA}=D_{EDTACa}=200$ μm$^2$ s$^{-1}$). z is the charge number ($z_{Ca}=+2$, $z_k=+1$, $z_{cl}=-1$). F is the Faraday constant. $k_b$ is the Boltzmann constant. T is the temperature (300 k). V is the electric potential. α is the forward binding rate ($\alpha_E=5$ μM$^{-1}$s$^{-1}$, $\alpha_F=150$ s$^{-1}$). β is the backward binding rate ($\beta_E=0.75$ μM$^{-1}$s$^{-1}$, $\beta_F=450$ s$^{-1}$). The footnote $_E$ and $_F$ stands for EDTA and Fluo-8, respectively. ε is the dielectric constant permittivity of water. The boundary condition on the cis side is set with varying KCl concentration (0.5 M to 2.5 M), whereas the boundary condition on the trans side is set as 0.75 M CaCl$_2$.

Stationary distribution of ions in different simulation conditions are numerically solved by Comsol 5.3a. Briefly, an axis-symmetric simulation geometry is defined as two hemispherical spaces separated by a semi-permeable membrane, where only the passage of liquid instead of ions are permitted (FIG. 2). The two hemispheres, which represents the cis and the trans side respectively, are connected by a cylindrical nanopore on the membrane, where free passage of liquid and ions are both permitted.

When illuminated in TIRF mode, the excitation intensity decays exponentially in z-direction. To simulate the fluorescence intensity in a projected x-y plane, equation (13) is used, where T is the decay constant of the evanescent wave in the z direction:

$$F(x, y) = F_0 \int [FluoCa](x, y, z)\exp\left(-\frac{z}{\gamma}\right)dz \quad (13)$$

While the total fluorescence intensity is estimated according to equation (14):

$$F_{Total} = \int\int F(x, y)dxdy \quad (14)$$

2D Gaussian Fitting

During electrode-free oSCR, the fluorescence intensity profile, which appear as a bright spot, were fit to a 2D Gaussian distribution according to equation (15):

$$f(x, y) = z_0 + A\exp\left(-\left(\frac{(x-x_c)^2}{2\sigma_x^2} + \frac{(y-y_c)^2}{2\sigma_y^2}\right)\right) \quad (15)$$

Here, f(x, y) stands for the fitted fluorescence intensity in the x-y plane. $z_0$ stands for base level, A stands for the fitting amplitude, $x_c$ and $y_c$ stands for the centroid of the fitting. $\sigma_x$ and $\sigma_y$ stands for the standard deviation of the distribution in x and y direction, respectively.

Figure 5:
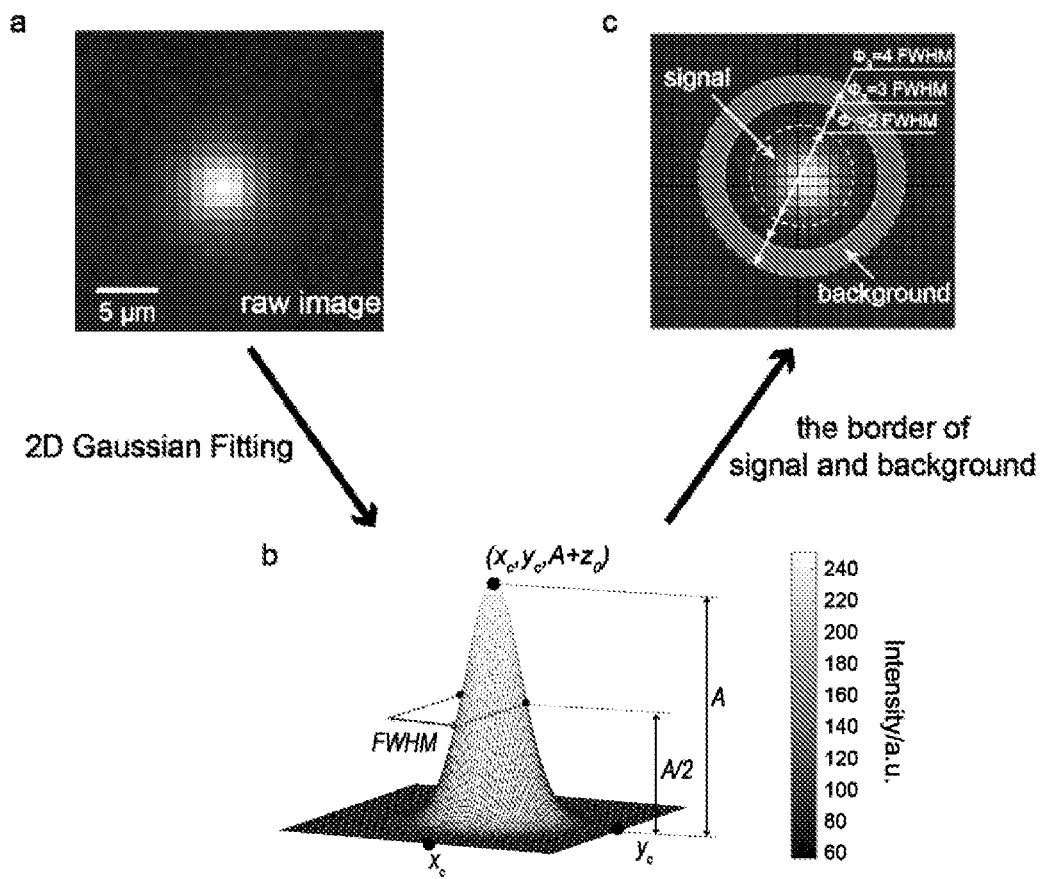
FIG. 5 shows definition of signal and background during oSCR. a, A representative image frame acquired directly from electrode-free oSCR for a nanopore. b, The 2D Gaussian fitting $$f(x, y) = z_0 + A\exp\left(-\frac{(x - x_c)^2}{2\sigma_x^2} - \frac{(y - x_c)^2}{2\sigma_y^2}\right)$$

This function allows for position localization for a tracked spot with sub-pixel resolution. The full width half magnitude (FWHM) of the 2D Gaussian function describes its width at half height and can be used to evaluate the spot size. Here the cftool module in MATLAB is used to perform 2D Gaussian fitting (FIG. 5). The FWHM were derived from equation (16):

$$FWHM = 2\sqrt{2\ln 2}\,\sigma_x \quad (16)$$

We defined the pixels with in the circle with a diameter of 2 FWHM as the signal, the pixels in the circular ring, between the circles with the diameter of 3 FWHM and 4 FWHM, as background (FIG. 5).

Signal to Background Ratio (SBR) Evaluation

The SBR value was introduced to quantitatively evaluate the performance of DOP recording from different trials of DOP recordings. The SBR value is calculated as:

$$SBR = \frac{\text{peak}(sig) - \text{mean}(bkg)}{\text{std}(bkg)} \quad (17)$$

Here, peak(sig) is the peak amplitude $(A+z_0)$ of the signal obtained from 2D Gaussian fitting (FIG. 5). mean(bkg) is the mean pixel intensity of the background $(z_0)$. std(bkg) is the standard deviation of pixel intensity of the background. The definition of the signal and the background is shown in FIG. 5.

REFERENCE

1. André, B. An overview of membrane transport proteins in *Saccharomyces cerevisiae*. Yeast 11, 1575-1611 (1995).
2. Gouaux, E. & MacKinnon, R. Principles of selective ion transport in channels and pumps. Science 310, 1461-1465 (2005).
3. Nielsen, S. et al. Specialized membrane domains for water transport in glial cells: high-resolution immunogold cytochemistry of aquaporin-4 in rat brain. Journal of Neuroscience 17, 171-180 (1997).
4. Wood, I. S. & Trayhurn, P. Glucose transporters (GLUT and SGLT): expanded families of sugar transport proteins. British Journal of Nutrition 89, 3-9 (2003).
5. Choi, K. H. et al. Insight into DNA and protein transport in double-stranded DNA viruses: the structure of bacteriophage N4. Journal of molecular biology 378, 726-736 (2008).
6. Bressloff, P. C. & Newby, J. M. Stochastic models of intracellular transport. Rev Mod Phys 85, 135-196 (2013).
7. Deamer, D., Akeson, M. & Branton, D. Three decades of nanopore sequencing. Nat Biotechnol 34, 518-524 (2016).
8. Huang, S. Nanopore-based sensing devices and applications to genome sequencing: a brief history and the missing pieces. Chin. Sci. Bull. 59, 49184928 (2014).
9. Kasianowicz, J. J., Brandin, E., Branton, D. & Deamer, D. W. Characterization of individual polynucleotide molecules using a membrane channel. P Natl Acad Sci USA 93, 13770-13773 (1996).
10. Bayley, H. et al. Droplet interface bilayers. Mol Biosyst 4, 1191-1208 (2008).
11. Sapra, K. T. & Bayley, H. Lipid-coated hydrogel shapes as components of electrical circuits and mechanical devices. Sci Rep-Uk 2, 848 (2012).
12. Li, J. et al. Ion-beam sculpting at nanometre length scales. Nature 412, 166-169 (2001).
13. Zhang, B. et al. Bench-top method for fabricating glass-sealed nanodisk electrodes, glass nanopore electrodes, and glass nanopore membranes of controlled size. Anal Chem 79, 4778-4787 (2007).
14. Geng, J. et al. Stochastic transport through carbon nanotubes in lipid bilayers and live cell membranes. Nature 514, 612 (2014).
15. Chou, L. Y., Ming, K. & Chan, W. C. Strategies for the intracellular delivery of nanoparticles. Chemical Society Reviews 40, 233-245 (2011).
16. Barry, R. J., Clarke, A. R. & Johnstone, S. J. A review of electrophysiology in attention-deficit/hyperactivity disorder: I. Qualitative and quantitative electroencephalography. Clinical neurophysiology 114, 171-183 (2003).
17. Dunlop, J., Bowlby, M., Peri, R., Vasilyev, D. & Arias, R. High-throughput electrophysiology: an emerging paradigm for ion-channel screening and physiology. Nat Rev Drug Discov 7, 358-368 (2008).
18. Jain, M. et al. Nanopore sequencing and assembly of a human genome with ultra-long reads. Nat Biotechnol 36, 338-+(2018).
19. Letellier, L., Planeon, L., Bonhivers, M. & Boulanger, P. Phage DNA transport across membranes. Research in microbiology 150,499-505 (1999).
20. Song, L. et al. Structure of staphylococcal α-hemolysin, a heptameric transmembrane pore. Science 274, 1859-1865 (1996).
21. Huang, S., Romero-Ruiz, M., Castell, O. K., Bayley, H. & Wallace, M. I. High-throughput optical sensing of nucleic acids in a nanopore array. Nat Nano 10, 986-U996 (2015).
22. Wang, Y. Q. et al. Osmosis-Driven Motion-Type Modulation of Biological Nanopores for Parallel Optical Nucleic Acid Sensing. Acs Appl Mater Inter 10, 7788-7797 (2018).
23. Heron, A. J., Thompson, J. R., Cronin, B., Bayley, H. & Wallace, M. I. Simultaneous measurement of ionic current and fluorescence from single protein pores. J. Am. Chem. Soc 131, 1652-1653 (2009).
24. Anderson, B. N. et al. Probing solid-state nanopores with light for the detection of unlabeled analytes. Acs Nano 8, 11836-11845 (2014).
25. Ivankin, A. et al. Label-Free Optical Detection of Biomolecular Translocation through Nanopore Arrays. Biophys J 108, 331a-331a (2015).
26. Shuai, J. & Parker, I. Optical single-channel recording by imaging Ca2+ flux through individual ion channels: theoretical considerations and limits to resolution. Cell Calcium 37, 283-299 (2005).
27. Gu, L. Q., Braha, O., Conlan, S., Cheley, S. & Bayley, H. Stochastic sensing of organic analytes by a pore-forming protein containing a molecular adapter. Nature 398, 686-690 (1999).
28. Gu, L. Q., Cheley, S. & Bayley, H. Capture of a single molecule in a nanocavity. Science 291, 636-640(2001).
29. Kang, X. F., Cheley, S., Guan, X. Y. & Bayley, H. Stochastic detection of enantiomers. J Am Chem Soc 128, 10684-10685 (2006).
30. Bayley, H. & Cremer, P. S. Stochastic sensors inspired by biology. Nature 413, 226 (2001).
31. Fennouri, A. et al. Kinetics of enzymatic degradation of high molecular weight polysaccharides through a nanopore: experiments and data-modeling. Anal Chem 85, 8488-8492 (2013).
32. Braha, O. et al. Simultaneous stochastic sensing of divalent metal ions. Nat Biotechnol 18, 1005 (2000).
33. Clarke, J. et al. Continuous base identification for single-molecule nanopore DNA sequencing. Nat Nanotechnol 4, 265 (2009).
34. Boersma, A. J., Brain, K. L. & Bayley, H. Real-time stochastic detection of multiple neurotransmitters with a protein nanopore. Acs Nano 6, 5304-5308 (2012).
35. Boersma, A. J. & Bayley, H. Continuous stochastic detection of amino acid enantiomers with a protein nanopore. Angewandte Chemie 124, 9744-9747 (2012).
36. Sacerdote, M. & Szostak, J. Semipermeable lipid bilayers exhibit diastereoselectivity favoring ribose. Proceedings of the National Academy of Sciences 102, 6004-6008 (2005).
37. Raghunathan. A. & Aluru. N. Molecular undcstanding of osmosis in semipermeable membranes. Phys Rev Lett 97.024501 (2006).
38. Robertson. J. W. et al. Single-molecule mass spectrometry in solution using a solitary nanopore. Proceedings of the National Academy of Sciences 104, 8207-8211 (2007).
39. Rodrigues. C. G., Machado. D. C., Chevtchenko. S. F. & Krasilnikov, O. V. Mechanism of KCI enhancement in detection of nonionic polymers by nanopore sensors. Biophys J 95, 5186-5192(2008).
40. Soskine, M. et al. An engineered ClyA nanopore detects folded target proteins by selective external association and pore entry. Nano letters 12.4895-4900 (2012).
41. Biesemans, A., Soskine, M. & Maglia, G. A Protein Rotaxane Controls the Translocation of Proteins Across a ClyA Nanopore. Nano letters 15, 6076-6081 (2015).
42. Franceschini, L., Brouns, T., Willems, K., Carton. E. & Maglia, G. DNA Translocation through Nanopores at Physiological Ionic Strengths Requires Precise Nanoscale Engineering. Acs Nano 10, 8394-8402 (2016).
43. Franceschini. L., Soskine, M., Biesemans. A. & Maglia. G. A nanopore machine promotes the vectorial transport of DNA across membranes. Nature communications 4, 2415 (2013).
44. Soskine, M., Biesemans, A. & Maglia, G. Single-Molecule Analyte Recognition with ClyA Nanopores Equipped with Internal Protein Adaptors. Journal of the American Chemical Society 137, 5793-5797 (2015).
45. Wendell. D. et al. Translocation of double strrnded DNA through membrane-adapted phi29 motor protein nanopores. Nat Nanotechnol 4, 765 (2309).
46. Manrao, E. A. Reading DNA at single-nucleot de resolution with a mutant MspA nanopore and phi29 DNA polymerase. Nature Biotechnol. 30, 349-353 (2012).
47. Tinland, B., Pluen. A., Sturm. J. & Weill. G. Persistence length of single-stranded DNA. Macromolecules 30, 5763-5765 (1997).
48. Nomidis, S. K., Hooyberghs. J., Maglia. G. & Cation. E. DNA capture into the ClyA nanopore: diffusion-limited versus reaction-limited processes. Journal of Physics: Condensed Matter (2018).
49. Chen, Z. T. et al. Centrifugal micro-channel array droplet generation for highly parallel digital PCR. Lab Chip 17, 235-240 (2017).
50. Nakano. A. Spinning-disk confocal microscopy-a cutting-edge tool for imaging of membrane traffic. Cell structure and function 27, 349-355 (2002).

The invention claimed is:

1. A system without electrodes for identifying an analyte, the system comprising:
   (a) a first compartment having a first aqueous solution in it, wherein the first aqueous solution comprises a fluorescent reporter molecule configured to emit fluorescence when bound to an ionic species;
   (b) a second compartment having a distinct second aqueous solution in it, wherein the second aqueous solution comprises the ionic species which are specifically bound to said fluorescence reporter molecule; and
   (c) a membrane separating the first compartment and second compartment; wherein the membrane between the first compartment and the second compartment has at least one inserted nanopore such that the first compartment and the second compartment are connected by the nanopore; wherein there is a chemical gradient of the ionic species between the first compartment and the second compartment, and said chemical gradient is configured to drive the ionic species, in order to diffuse from the second compartment to the first compartment through the nanopore.

2. The system according to claim 1, wherein the membrane is a semipermeable membrane consisting of lipids or triblock copolymers.

3. The system according to claim 2, wherein the osmolarity of the second aqueous solution is higher than the osmolarity of the first aqueous solution or the osmolality of the second aqueous solution is higher than the osmolality of the first aqueous solution; or the osmolarity of the second aqueous solution is equal to the osmolarity of the first aqueous solution or the osmolality of the second aqueous solution is equal to the osmolality of the first aqueous solution; or the osmolarity of the second aqueous solution is lower than the osmolarity of the first aqueous solution or the osmolality of the second aqueous solution is lower than the osmolality of the first aqueous solution.

4. The system according to claim 2, wherein the lipid is one or more selected from the group consisting of monoolein; 1,2-dioleoyl-sn glycero-S-phosphocholine (DOPC); 1,2-diphytanoyl-sn-glycero-3-phosphatidylcholine (DPhPC); palmitoyl oleoyl phosphatidylcholine (POPC); 1-palmitoyl-2-oleoyl phosphatidylethanolamine (POPE); 1-palmitoyl-2-oleoyl-phosphatidylethanolamine; 1-palmitoyl-2-oleoylphosphatidylglycerol (POPE/POPG) mixtures; and mixtures thereof.

5. The system according to claim 1, wherein the first compartment is provided by an aqueous droplet, and the second compartment is provided by a hydrogel layer comprising 0.1-20% (w/v) agarose.

6. The system according to claim 1, wherein the nanopore is selected from the group consisting of protein nanopore, and the protein nanopore is one or more selected from the group consisting of α-HL, ClyA, ClyA-RR, Phi29 connector protein, aerolysine, MspA, OmpF, OmpG, FraC, HlyA, SheA, sp1 and variants thereof and ion channel.

7. The system according to claim 1, wherein the ionic species is one or more selected from the group consisting of $Ag^+$, $Ag^{2+}$, $Al^{3+}$, $As^{3+}$, $Au^+$, $Ba^{2+}$, $Bi^{3+}$, $Ca^{2+}$, $Cd^{2+}$, $Ce^{3+}$, $Ce^{4+}$, $Cl^-$, $Co^{2+}$, $Cr^{3+}$, $Cu^+$, $Cu^{2+}$, $Dy^{3+}$, $Eu^{3+}$, $Fe^{2+}$, $Fe^{3+}$, $Ga^{3+}$, $Hg^+$, $Hg^{2+}$, $In^{3+}$, $K^+$, $La^{3+}$, $Mg^{2+}$, $Mn^{2+}$, $Mo^{3+}$, $Na^+$, $Ni^{2+}$, $OH^-$, $pb^{2+}$, $pd^{2+}$, $Pt^{2+}$, $Pt^{4+}$, $Ru^{3+}$, $Sb^{3+}$, $Sn^{2+}$, $Tb^{3+}$, $Tl^+$, and $Zn^{2+}$.

8. The system according to claim 1, wherein the second aqueous solution comprises calcium chloride.

9. The system according to claim 8, wherein the concentration of calcium chloride in the second aqueous solution is 0.01-6.76 M.

10. The system according to claim 1, wherein the first aqueous solution comprises a chelating agent wherein the chelating agent is able to bind to said ionic species.

11. The system according to claim 1, wherein the system further comprises a light source for illuminating and a light sensor for detecting the fluorescence.

12. The system according to claim 1, wherein the first aqueous solution or the second aqueous solution comprises the analyte.

13. The system according to claim 12, wherein the analyte is selected from the group consisting of a compound, a drug, a sugar, an ion, a neurotransmitter, an amino acid, a nucleotide, a polymer, a polypeptide, a polysaccharide and a polynucleotide.

14. A method of identifying an analyte, the method comprising the steps of:
   (a) providing the system according to claim 1, wherein the analyte is provided in the first compartment or in the second compartment;
   (b) applying a light capable of exciting the fluorescent reporter molecule to a region in the first compartment proximal to the nanopores;
   (c) measuring the fluorescence signal from the fluorescent reporter molecule to identify the analyte.

15. A nanopore array without electrodes for identifying multiple analytes, the nanopore array comprising multiple systems in parallel and each system is a system according to claim 1
   wherein the multiple systems are arranged such that the measured fluorescence can be distinguished for each system.

16. The nanopore array according to claim 15, wherein the first compartments of the multiple systems are separated from each other and the first compartment of each system is provided by an aqueous droplet.

17. The nanopore array according to claim 15, wherein the second compartment of the multiple system is a single compartment, and the second compartment of each system is provided by a hydrogel layer comprising 0.1-20% (w/v) agarose.

18. The nanopore array according to claim 15, wherein different analytes are physically separated into various systems.

19. The nanopore array according to claim 15, wherein the density of the systems in the nanopore array is 10-1000 per $mm^2$, and the total area provided by the multiple systems is 1-100 $mm^2$.

20. A method of manufacturing the nanopore array according to claim 15, comprising:
   (a) providing multiple aqueous droplets, wherein each of the aqueous droplets comprises a first aqueous solution which comprises a protein nanopore, an analyte and a fluorescent reporter molecule capable of emitting fluorescence when bound to an ionic species;
   (b) providing a hydrogel layer, wherein the hydrogel layer comprises the ionic species;
   (c) bringing the multiple aqueous droplets and the hydrogel layer together in a hydrophobic medium comprising amphipathic molecules such that a semipermeable membrane is formed between each of the aqueous droplets and the hydrogel layer.

* * * * *